US008129537B2

(12) United States Patent
Fenton et al.

(10) Patent No.: US 8,129,537 B2
(45) Date of Patent: Mar. 6, 2012

(54) COMPOUNDS AS PDE IV AND TNF INHIBITORS

(75) Inventors: Garry Fenton, Dagenham (GB); Tahir Nadeem Majid, Dagenham (GB); Malcolm Norman Palfreyman, Dagenham (GB)

(73) Assignees: Rhone-Poulenc Rorer Limited, Eastbourne, East Sussex (GB); Aventis Pharma Limited, West Malling, Kent (GB)

( * ) Notice: Subject to any disclaimer, the term of this patent is extended or adjusted under 35 U.S.C. 154(b) by 0 days.

(21) Appl. No.: 12/693,791

(22) Filed: Jan. 26, 2010

(65) Prior Publication Data

US 2010/0240677 A1    Sep. 23, 2010

Related U.S. Application Data

(60) Continuation of application No. 11/764,317, filed on Jun. 18, 2007, now Pat. No. 7,652,144, which is a continuation of application No. 11/290,322, filed on Nov. 30, 2005, now abandoned, which is a division of application No. 10/792,579, filed on Mar. 3, 2004, now Pat. No. 7,045,660, which is a continuation of application No. 10/207,493, filed on Jul. 29, 2002, now abandoned, which is a continuation of application No. 08/592,817, filed on Jan. 26, 1996, now Pat. No. 6,472,412, which is a continuation-in-part of application No. PCT/GB94/01630, filed on Jul. 28, 1994.

(30) Foreign Application Priority Data

Jul. 28, 1993    (GB) .................................... 9315581.0
Jul. 28, 1993    (GB) .................................... 9315632.1

(51) Int. Cl.
*C07D 211/72*    (2006.01)
*A61K 31/44*    (2006.01)
(52) U.S. Cl. .................. 546/309; 514/345; 514/357
(58) Field of Classification Search .............. 546/309; 514/345, 357
See application file for complete search history.

(56) References Cited

U.S. PATENT DOCUMENTS 5,679,696 A * 10/1997 Fenton et al. ................ 514/354

\* cited by examiner

*Primary Examiner* — Shailendra Kumar
(74) *Attorney, Agent, or Firm* — Scully, Scott, Murphy & Presser, P.C.

(57) ABSTRACT

This invention is directed to a [di(ether or thioether)heteroaryl or fluoro substituted aryl] compound or an N-oxide thereof or a pharmaceutically acceptable salt thereof, which is useful for inhibiting the production or physiological effects of TNF in the treatment of a patient suffering from a disease state associated with a physiologically detrimental excess of tumor necrosis factor (TNF).

Compounds within the scope of the present invention also inhibit cyclic AMP phosphodiesterase, and are useful in treating a disease state associated with pathological conditions that are modulated by inhibiting cyclic AMP phosphodiesterase, such disease states including inflammatory and autoimmune diseases, in particular type IV cyclic AMP phosphodiesterase. The present invention is therefore directed to their pharmacological use for inhibiting TNF and/or cyclic AMP phosphodiesterase, pharmacological compositions comprising the compounds and methods for their preparation.

30 Claims, No Drawings

COMPOUNDS AS PDE IV AND TNF INHIBITORS

This application is a CON of Ser. No. 11/764,317 Jun. 18, 2007 U.S. Pat. No. 7,652,144
which is a CON of Ser. No. 11/290,322 Nov. 30, 2005 ABN
which is a DIV of Ser. No. 10/792,579 Mar. 3, 2004 U.S. Pat. No. 7,045,660
which is a CON of Ser. No. 10/207,493 Jul. 29, 2002 ABN
which is a CON of Ser. No. 08/592,817 Jan. 26, 1996 U.S. Pat. No. 6,472,412
which is a CIP of PCT/GB94/01630 Jul. 28, 1994.

FIELD OF THE INVENTION

This invention is directed to [di(ether or thioether)heteroaryl or fluoro substituted aryl] compounds, their preparation, pharmaceutical compositions containing these compounds, and their pharmaceutical use in the treatment of disease states associated with proteins that mediate cellular activity.

Disease states associated with abnormally high physiological levels of cytokines such as TNF are treatable according to the invention. TNF is an important pro-inflammatory cytokine which causes hemorrhagic necrosis of tumors and possesses other important biological activities. TNF is released by activated macrophages, activated T-lymphocytes, natural killer cells, mast cells and basophils, fibroblasts, endothelial cells and brain astrocytes among other cells.

The principal in vivo actions of TNF can be broadly classified as inflammatory and catabolic. It has been implicated as a mediator of endotoxic shock, inflammation of joints and of the airways, immune deficiency states, allograft rejection, and in the cachexia associated with malignant disease and some parasitic infections. In view of the association of high serum levels of TNF with poor prognosis in sepsis, graft versus host disease and acute respiratory distress syndrome, and its role in many other immunological processes, this factor is regarded as an important mediator of general inflammation.

TNF primes or activates neutrophils, eosinophils, fibroblasts and endothelial cells to release tissue damaging mediators. TNF also activates monocytes, macrophages and T-lymphocytes to cause the production of colony stimulating factors and other pro-inflammatory cytokines such $IL_1$, $IL_6$, $IL_8$ and GM-CSF, which in some case mediate the end effects of TNF. The ability of TNF to activate T-lymphocytes, monocytes, macrophages and related cells has been implicated in the progression of Human Immunodeficiency Virus (HIV) infection. In order for these cells to become infected with HIV and for HIV replication to take place the cells must be maintained in an activated state. Cytokines such as TNF have been shown to activate HIV replication in monocytes and macrophages. Features of endotoxic shock such as fever, metabolic acidosis, hypotension and intravascular coagulation are thought to be mediated through the actions of TNF on the hypothalamus and in reducing the anti-coagulant activity of vascular endothelial cells. The cachexia associated with certain disease states is mediated through indirect effects on protein catabolism. TNF also promotes bone resorption and acute phase protein synthesis.

The discussion herein related to disease states associated with TNF include those disease states related to the production of TNF itself, and disease states associated with other cytokines, such as but not limited to IL-1, or IL-6, that are modulated by association with TNF. For example, an IL-1 associated disease state, where IL-1 production or action is exacerbated or secreted in response to TNF, would therefore be considered a disease state associated with TNF. TNF-alpha and TNF-beta are also herein referred to collectively as "TNF" unless specifically delineated otherwise, since there is a close structural homology between TNF-alpha (cachectin) and TNF-beta (lymphotoxin) and each of them has a capacity to induce similar biologic responses and bind to the same cellular receptor.

Disease states associated with pathological conditions that are modulated by inhibiting enzymes, which are associated with secondary cellular messengers, such as cyclic AMP phosphodiesterase, are also treatable according to the invention Cyclic AMP phosphodiesterase is an important enzyme which regulates cyclic AMP levels and in turn thereby regulates other important biological reactions. The ability to regulate cyclic AMP phosphodiesterase, including type IV cyclic AMP phosphodiesterase, therefore, has been implicated as being capable of treating assorted biological conditions.

In particular, inhibitors of type IV cyclic AMP phosphodiesterase have been implicated as being bronchodilators and asthma-prophylactic agents and as agents for inhibiting eosinophil accumulation and of the function of eosinophils, and for treating other diseases and conditions characterized by, or having an etiology involving, morbid eosinophil accumulation. Inhibitors of cyclic AMP phosphodiesterase are also implicated in treating inflammatory diseases, proliferative skin diseases and conditions associated with cerebral metabolic inhibition.

Reported Developments

Chemical Abstracts, 108 (15), Apr. 11, 1988, abstract no. 131583p pertains to an abstract of Japanese Patent Application Publication No. JP-A-62 158,253 which discloses that a substituted phenyl compound of formula

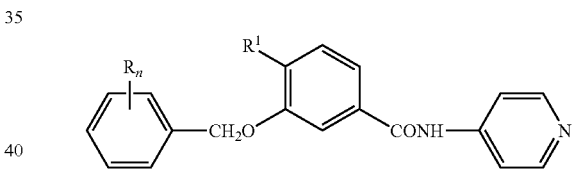

is a cardiotonic, but does not disclose or suggest that the compound inhibits cyclic AMP phosphodiesterase or TNF. JP-A-62 158,253 also does not disclose or suggest that the moiety that is ortho to $R^1$ may be anything other than benzyloxy. JP-A-62 158,253 furthermore does not disclose compounds wherein a methine (=CH—) moiety of the phenyl moiety of the benzamido moiety is substituted by a halomethine (=CX—; wherein X is a halo atom) moiety or an imine (=N—) moiety.

Chemical Abstracts, 99 (6), Aug. 8, 1983, abstract no. 43556z pertains to an abstract of Japanese Patent Application Publication No. JP-A-5 869,812 which discloses that a phenyl compound of formula

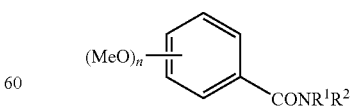

is a hypoglycemic agent, but does not disclose or suggest that the compound inhibits cyclic AMP phosphodiesterase or TNF. JP-A-5 869,812 also does not disclose or suggest that the benzamido moiety may be substituted by anything other than methoxy.

Panos Grammaticakis, *Bull. Soc. Chim. Fr.*, 848-857 (1965) discloses a phenyl compound of the formula

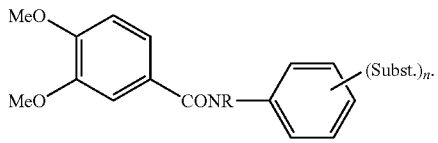

Grammaticakis examines the ultraviolet and visible absorbances of compounds bearing different substituents. Grammaticakis does not disclose or suggest that the compound exhibits any pharmacological activity. JP-A-5 869,812 also does not disclose or suggest that the benzamido moiety may be substituted by anything other than methoxy.

Ian W. Mathison, et al., *J. Med. Chem.*, 16(4), 332-336 (1973), discloses that a phenyl compound of formula

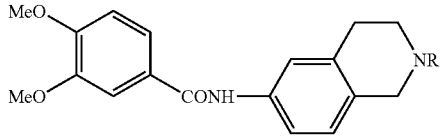

is a hypotensive agent, but do not disclose or suggest that the compound inhibits cyclic AMP phosphodiesterase or TNF. Mathison, et al., also do not disclose or suggest that the benzamido moiety may be substituted by anything other than methoxy.

European Patent Application Publication No. EP 232199 B1 discloses that phenyl compounds of formula

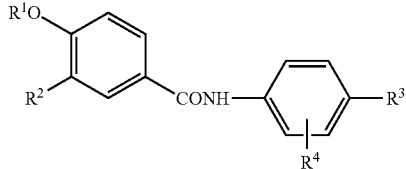

wherein $R^2$ is alkyl or mono- or polycyclic cycloalkyl, exhibit anti-inflammatory and/or anti-allergic activity. EP 232199 B1 does not disclose or suggest compounds wherein the $R^2$ substituent is bonded to the phenyl moiety via an oxygen or sulfur atom. EP 232199 B1 furthermore does not disclose compounds wherein a methine moiety of the phenyl moiety of the benzamido moiety is substituted by a halomethine moiety or an imine moiety.

European Patent Application Publication No. EP 470,805 A1 discloses phenyl compounds of the formula

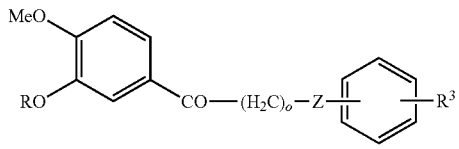

wherein R may be $C_{3-7}$ alkyl, $C_{3-7}$ cycloalkyl or

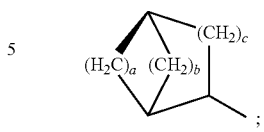

Z may be a bond; o is 1-4; a and b are independently 1-3; and c is 0-2. EP 470,805 A1 discloses that these compounds are useful intermediates for preparing PDE IV inhibitors, but does not disclose or suggest that the compounds have any pharmacological activity. EP 470,805 A1 furthermore does not disclose compounds wherein a methine moiety of the phenyl moiety of the phenylacyl moiety is substituted by a halomethine moiety or an imine moiety.

Japanese Patent Application Publication No. JP-A-0 4360847 discloses compounds of the formula

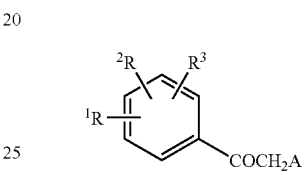

wherein $R^1$, $R^2$ and $R^3$ may be the same or different and may be halo or lower alkoxy or lower alkyl both optionally substituted by halo; and A may be optionally substituted aryl or 5-6 membered heterocyclyl group. JP-A-0 4360847 discloses that the compounds are useful intermediates for preparing antimicrobial agents, but does not disclose or suggest that the compounds have any pharmacological activity. JP-A-0 4360847 also does not disclose that the compounds wherein the phenylacyl moiety is substituted in the 3, 4 positions relative to the acyl moiety by lower alkoxy groups and has a methine moiety of the phenyl moiety substituted by a halomethine moiety or an imine moiety.

WO Patent Application No. 92/12961 discloses that compounds of the formula

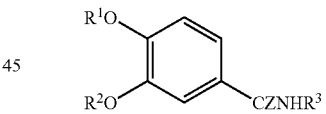

inhibit cyclic AMP phosphodiesterase. WO Patent Application No. 92/12961 does not disclose or suggest that these compound inhibit TNF. WO Patent Application No. 92/12961 also does not disclose compounds wherein a methine moiety of the diether phenyl moiety is substituted by a halomethine moiety or an imine moiety.

WO Patent Application No. 93/25517 discloses that compounds of the following formula inhibit PDE IV. WO Patent Application No. 93/25517 does

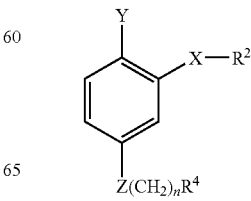

not disclose or suggest that these compound inhibit TNF. WO Patent Application No. 93/25517 also does not disclose compounds wherein a methine moiety of the diether phenyl moiety is substituted by a halomethine moiety or an imine moiety.

WO Patent Application No. 93/10228 discloses that compounds of the following formula inhibit PDE IV and as such are useful in treatment of inflammatory diseases. WO Patent Application No. 93/10228 does not disclose or suggest

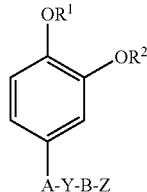

that these compounds inhibit TNF. WO Patent Application No. 93/10228 also does not disclose compounds wherein a methine moiety of the diether phenyl moiety is substituted by a halomethine moiety or an imine moiety.

WO Patent Application No. 93/07111 discloses that compounds of the following formula wherein X may be $YR_2$; Y is O or $S(O)_m$; $X_3$ is halogen or

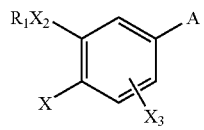

hydrogen; and A is a group of formula

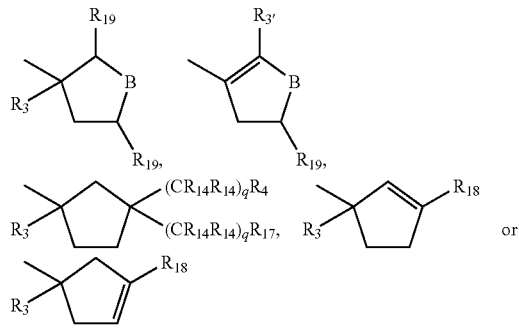

inhibit PDE IV. WO Patent Application No. 93/07111 does not disclose or suggest compounds wherein the A substituent is a [(—CXNH- or —CXCH$_2$-)aryl or heteroaryl] moiety wherein X is O or S.

WO Patent Application No. 91/16303 discloses that compounds of the following formula wherein $R_1$, $R_2$ and $R_3$ may be hydrogen, halogen, lower alkyl,

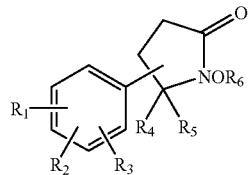

lower alkoxy or cycloalkoxy inhibit PDE IV. WO Patent Application No. 91/16303 does not disclose or suggest compounds wherein the lactam moiety is substituted by a [(—CXNH- or —CXCH$_2$-)aryl or heteroaryl] moiety wherein X is O or S.

WO Patent Application No. 92/19594 discloses that compounds of the following formula wherein X may be $YR_2$; Y is O or $S(O)_m$; and $X_3$ may be

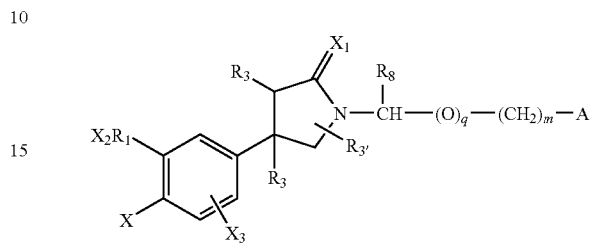

hydrogen or halogen inhibit PDE IV. WO Patent Application No. 92/19594 does not disclose or suggest compounds wherein the lactam moiety is substituted by a [(—CXNH- or —CXCH$_2$-)aryl or heteroaryl] moiety wherein X is O or S.

SUMMARY OF THE INVENTION

This invention is directed to a compound of formula I, which is useful for inhibiting the production or physiological effects of TNF in the treatment of a patient suffering from a disease state associated with a physiologically detrimental excess of tumor necrosis factor (TNF), where formula I is as follows:

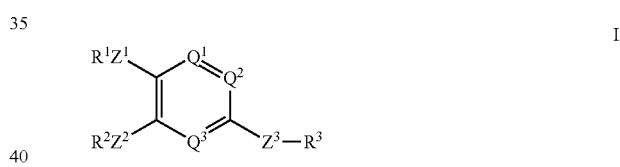

wherein $R^1$ is lower alkyl optionally substituted by one or more of halo, cycloalkyl or cycloalkenyl;

$R^2$ is alkyl, alkenyl or alkynyl each optionally substituted by one or more of halo, cycloalkyl or cycloalkenyl; or cycloalkyl or cycloalkenyl each optionally substituted by one or more of halo, methylidene or alkyl; or optionally substituted cyclothioalkyl consisting of a non-aromatic monocyclic or multicyclic ring system of 3 to about 10 ring atoms wherein at least one of the ring atoms is sulphur and the other ring atoms are carbon and the substituted cyclothioalkyl is substituted by one or more halo, or any ring sulphur atom is optionally oxidised to the corresponding S-oxide or S,S-dioxide; or optionally substituted cyclothioalkenyl consisting of a non-aromatic monocyclic or multicyclic ring system of 3 to about 10 ring atoms wherein at least one of the ring atoms is sulphur, the other ring atoms are carbon and the ring system contains a carbon-carbon double bond and the substituted cyclothioalkenyl is substituted by one or more halo or any ring sulphur atoms is optionally oxidised to the corresponding S-oxide or S,S-dioxide;

$R^3$ is optionally substituted aryl or heteroaryl, wherein the substituted aryl or substituted heteroaryl group is substituted by one or more substituents which may be the same or different and are selected from alkyl, aryl, aralkyl, hydroxy, hydroxyalkyl, alkoxy, aryloxy, aralkyloxy, carboxy, acyl, aroyl, halo, nitro, cyano, carboxy, alkoxycarboxyl, aryloxycarbonyl, aralkyloxycarbonyl, acylamino, aroylamino, alkylsulfonyl, arylsulfonyl, alkylsulfinyl, arylsulfinyl, alkylthio, arylthio, aralkylthio, $Y^1Y^2N-$, $Y^1Y^2NCO-$ or $Y^1Y^2NSO_2-$, where $Y^1$ and $Y^2$ are independently hydrogen, alkyl, aryl, and aralkyl;

$Q^1$, $Q^2$ and $Q^3$ are independently nitrogen, CX or CH, provided that at least one of $Q^1$, $Q^2$ and $Q^3$ is other than CH;

Z, $Z^1$ and $Z^2$ are independently oxygen or sulfur;

$Z^3$ is $-CH=CH-$, $-CZCH_2-$, $-CZ-CZ-$, $-CH_2-NH-$, $-CH_2-O-$, $-CX_2-O-$, $-CH_2-S-$, $-CH_2-SO_2-$ or $-CZNH-$; and X is halo;

or N-oxide thereof or a pharmaceutically acceptable salt thereof; with the proviso that $R^1Z^1$ and $R^2Z^2$ cannot both represent methoxy.

Compounds within the scope of the present invention also inhibit cyclic AMP phosphodiesterase, and are useful in treating a disease state associated with pathological conditions that are modulated by inhibiting cyclic AMP phosphodiesterase, such disease states including inflammatory and autoimmune diseases, in particular type IV cyclic AMP phosphodiesterase. The present invention is therefore directed to their pharmacological use, pharmacological compositions comprising the compounds and methods for their preparation.

DETAILED DESCRIPTION OF THE INVENTION

As used above, and throughout the description of the invention, the following terms, unless otherwise indicated, shall be understood to have the following meanings:

DEFINITIONS

"Patient" includes both human and other mammals.

"Alkyl" means an aliphatic hydrocarbon group which may be straight or branched having about 1 to about 15 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl group is optionally substituted by one or more of halo, cycloalkyl or cycloalkenyl groups. Exemplary alkyl groups include methyl, fluoromethyl, difluoromethyl, trifluoromethyl, cyclopropylmethyl, cyclopentylmethyl, ethyl, n-propyl, i-propyl, n-butyl, t-butyl, n-pentyl, 3-pentyl, heptyl, octyl, nonyl, decyl and dodecyl; preferred are methyl, difluoromethyl and i-propyl.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain which may be straight or branched. The alkenyl group is optionally substituted by one or more halo, cycloalkyl or cycloalkenyl. Exemplary alkenyl groups include ethenyl, propenyl, n-butenyl, i-butenyl, 3-methylbut-2-enyl, n-pentenyl, heptenyl, octenyl and decenyl.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Branched means that one or more lower alkyl groups such as methyl, ethyl or propyl are attached to a linear alkynyl chain. "Lower alkynyl" means about 2 to about 4 carbon atoms in the chain which may be straight or branched. The alkynyl group is optionally substituted by one or more halo, cycloalkyl or cycloalkenyl. Exemplary alkynyl groups include ethynyl, propynyl, n-butynyl, 2-butynyl, 3-methylbutynyl, n-pentynyl, heptynyl, octynyl and decynyl.

"Cycloalkyl" means a non-aromatic mono- or multicyclic ring system of about 3 to about 10 carbon atoms. The cycloalkyl group is optionally substituted by one or more halo, methylidene ($H_2C=$) or alkyl. Exemplary monocyclic cycloalkyl rings include cyclopentyl, fluorocyclopentyl, cyclohexyl and cycloheptyl; more preferred is cyclopentyl. Exemplary multicyclic cycloalkyl rings include 1-decalin, adamant-(1- or 2-)yl, trinorbornyl and tricyclo[$2.2.1.0^{2.6}$]heptyl.

"Cycloalkenyl" means a non-aromatic monocyclic or multicyclic ring system containing a carbon-carbon double bond and having about 3 to about 10 carbon atoms. The cycloalkenyl group is optionally substituted by one or more halo, alkyl and methylidene ($CH_2=$). Preferred monocyclic cycloalkenyl rings include cyclopentenyl, cyclohexenyl or cycloheptenyl; more preferred is cyclopentenyl. A preferred multicyclic cycloalkenyl ring is a norbornylenyl.

"Cyclothioalkyl" means a non-aromatic monocyclic or multicyclic ring system of about 3 to about 10 ring atoms wherein at least one of the ring atoms is sulfur and the other ring atoms are carbon. Preferred rings include about 5 to about 6 ring atoms. Also preferred are rings in which one or two of the ring atoms is/are sulfur. The cyclothioalkyl is optionally substituted by one or more halo. The thio moiety of the cyclothioalkyl ring may also be optionally oxidized to the corresponding S-oxide or S,S-dioxide. Preferred monocyclic cyclothioalkyl rings include tetrahydrothiophenyl and tetrahydrothiopyranyl; more preferred is tetrahydrothiophenyl.

"Cyclothioalkenyl" means a non-aromatic monocyclic or multicyclic ring system having about 3 to about 10 ring atoms wherein at least one of the ring atoms is sulfur and the other ring atoms are carbon and the ring system contains a carbon-carbon double bond. Preferred rings include about 5 to about 6 ring atoms. Also preferred are rings in which one or two of the ring atoms is/are sulfur. The cyclothioalkenyl is optionally substituted by one or more halo. The thio moiety of the cyclothioalkenyl may also be optionally oxidized to the corresponding S-oxide or S,S-dioxide. Preferred monocyclic cyclothioalkyl rings include dihydrothiophenyl and dihydrothiopyranyl; more preferred is dihydrothiophenyl.

"Aromatic" means aryl or heteroaryl as defined below. Preferred aromatic groups include phenyl, halo substituted phenyl and azaheteroaryl.

"Aryl" means aromatic carbocyclic radical containing about 6 to about 10 carbon atoms. Exemplary aryl include phenyl or naphthyl, or phenyl or naphthyl substituted with one or more aryl group substituents which may be the same or different, where "aryl group substituent" includes hydrogen, alkyl, aryl, aralkyl, hydroxy, hydroxyalkyl, alkoxy, aryloxy, aralkyloxy, carboxy, acyl, aroyl, halo, nitro, cyano, carboxy, alkoxycarbonyl, aryloxycarbonyl, aralkyloxycarbonyl, acylamino, aroylamino, alkylsulfonyl, arylsulfonyl, alkylsulfinyl, arylsulfinyl, alkylthio, arylthio, aralkylthio, $Y^1Y^2N-$, $Y^1Y^2NCO-$ or $Y^1Y^2NSO_2-$, where $Y^1$ and $Y^2$ are independently hydrogen, alkyl, aryl, and aralkyl. Preferred aryl group substituents include hydrogen, alkyl, hydroxy, acyl, aroyl, halo, nitro, cyano, alkoxycarbonyl, acylamino, alkylthio, $Y^3Y^4N$—, $Y^3Y^4NCO$— and $Y^3Y^4NSO_2$—, where $Y^3$ and $Y^4$ are independently hydrogen and alkyl.

"Heteroaryl" means about a 5- to about a 10-membered aromatic monocyclic or multicyclic hydrocarbon ring system in which one or more of the carbon atoms in the ring system is/are element(s) other than carbon, for example nitrogen, oxygen or sulfur. The heteroaryl may also be substituted by one or more aryl group substituents. "Azaheteroaryl" means a subclass of heteroaryl wherein one or more of the atoms in the ring system is/are replaced by nitrogen. Imine nitrogen moieties of an azaheteroaryl group may also be in an oxidized state such as the corresponding N-oxide. Exemplary heteroaryl groups include pyrazinyl, furanyl, thienyl, pyridyl, pyrimidinyl, isoxazolyl, isothiazolyl, pyridazinyl, 1,2,4-triazinyl, quinolinyl, and isoquinolinyl. Preferred heteroaryl groups include pyrazinyl, thienyl, pyridyl, pyrimidinyl, isoxazolyl and isothiazolyl. Preferred azaheteroaryl groups include pyridyl, pyrimidinyl, pyridazinyl, pyrazinyl or 1,2,4-triazinyl.

"Aralkyl" means an aryl-alkyl- group in which the aryl and alkyl are as previously described. Preferred aralkyls contain a lower alkyl moiety. Exemplary aralkyl groups include benzyl, 2-phenethyl and naphthlenemethyl.

"Hydroxyalkyl" means a HO-alkyl- group in which alkyl is as previously defined. Preferred hydroxyalkyls contain lower alkyl. Exemplary hydroxyalkyl groups include hydroxymethyl and 2-hydroxyethyl.

"Acyl" means an H—CO— or alkyl-CO— group in which the alkyl group is as previously described. Preferred acyls contain a lower alkyl. Exemplary acyl groups include formyl, acetyl, propanoyl, 2-methylpropanoyl, butanoyl and palmitoyl.

"Aroyl" means an aryl-CO— group in which the aryl group is as previously described. Exemplary groups include benzoyl and 1- and 2-naphthoyl.

"Alkoxy" means an alkyl-O— group in which the alkyl group is as previously described. Exemplary alkoxy groups include methoxy, ethoxy, n-propoxy, i-propoxy, n-butoxy and heptoxy.

"Aryloxy" means an aryl-O— group in which the aryl group is as previously described. Exemplary aryloxy groups include phenoxy and naphthoxy.

"Aralkyloxy" means an aralkyl-O— group in which the aralkyl groups is as previously described. Exemplary aralkyloxy groups include benzyloxy and 1- or 2-naphthalenemethoxy.

"Alkylthio" means an alkyl-S— group in which the alkyl group is as previously described. Exemplary alkylthio groups include methylthio, ethylthio, i-propylthio and heptylthio.

"Arylthio" means an aryl-S— group in which the aryl group is as previously described. Exemplary arylthio groups include phenylthio and naphthylthio.

"Aralkylthio" means an aralkyl-S— group in which the aralkyl group is as previously described. An exemplary aralkylthio group is benzylthio.

"$Y^3Y^4N$—" means a substituted or unsubstituted amino group, wherein $Y^3$ and $Y^4$ are as previously described. Exemplary groups include amino ($H_2N$—), methylamino, ethylmethylamino, dimethylamino and diethylamino.

"Alkoxycarbonyl" means an alkyl-O—CO— group. Exemplary alkoxycarbonyl groups include methoxy- and ethoxycarbonyl.

"Aryloxycarbonyl" means an aryl-O—CO— group. Exemplary aryloxycarbonyl groups include phenoxy- and naphthoxycarbonyl.

"Aralkyloxycarbonyl" means an aralkyl-O—CO— group. An exemplary aralkyloxycarbonyl group is benzyloxycarbonyl.

"$Y^1Y^2NCO$—" means a substituted or unsubstituted carbamoyl group, wherein $Y^1$ and $Y^2$ are as previously described. Exemplary groups are carbamoyl ($H_2NCO$—) and dimethylcarbamoyl ($Me_2NCO$—).

"$Y^1Y^2NSO_2$—" means a substituted or unsubstituted sulfamoyl group, wherein $Y^1$ and $Y^2$ are as previously described. Exemplary groups are sulfamoyl ($H_2NSO_2$—) and dimethylsulfamoyl ($Me_2NSO_2$—).

"Acylamino" is an acyl-NH— group wherein acyl is as defined herein.

"Aroylamino" is an aroyl-NH— group wherein aroyl is as defined herein.

"Alkylsulfonyl" means an alkyl-$SO_2$— group. Preferred groups are those in which the alkyl group is lower alkyl.

"Alkylsulfinyl" means an alkyl-SO— group. Preferred groups are those in which the alkyl group is lower alkyl.

"Arylsulfonyl" means an aryl-$SO_2$— group.

"Arylsulfinyl" means an aryl-SO— group.

"Halo" means fluoro, chloro, bromo, or iodo. Preferred are fluoro, chloro or bromo; more preferred are fluoro or chloro, and further preferred is fluoro.

"N-oxide" means a moiety of the following structure

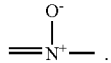

Preferred Embodiments

A compound of formula I is preferred for use in treating a disease state associated with a physiologically detrimental excess of tumor necrosis factor. Disease states associated with pathological conditions that are modulated by inhibiting tumor necrosis factor are treatable with a compound of formula I.

A compound of formula I is also preferred for use in treating a disease state associated with a physiologically detrimental excess of cyclic AMP phosphodiesterase. Disease states associated with pathological conditions that are modulated by inhibiting cyclic AMP phosphodiesterase are treatable with a compound of formula I.

According to a compound aspect of the invention, preferred compounds are described formula I,
wherein
  $R^2$ is alkyl, cycloalkyl, cycloalkenyl or cyclothioalkyl;
  $R^3$ is phenyl, substituted phenyl or azaheteroaryl;
  $Q^1$ and $Q^2$ are independently nitrogen, CX or CH, and at least one of $Q^1$ and $Q^2$ is other than CH;
  $Q^3$ is CH; and
  $Z^3$ is —$CZCH_2$— or —CZNH—.

According to a further compound aspect of the invention, preferred compounds are described formula I,
wherein
  $R^1$ is methyl or difluoromethyl;
  $R^2$ is isopropyl, cyclopropylmethyl, cyclopentyl, trinorbornyl, trinorbornenyl, tricyclo[2.2.1.0$^{2.6}$]heptanyl and tetrahydrothiophenyl;
  $Q^3$ is CH;
  $Z^1$ is oxygen or sulphur;
  $Z^2$ is oxygen; and
  $Z^3$ is —$COCH_2$— or —CONH—.

According to another aspect of the invention, more preferred compounds of formula I are described wherein $Q^1$ and $Q^2$ are independently nitrogen, CX or CH, and at least one of $Q^1$ and $Q^2$ is nitrogen or CX, and $Q^3$ is CH. Also preferred are compounds of the invention wherein $Q^1$ is CX, and $Q^2$ and $Q^3$ are CH; $Q^2$ is CX, and $Q^1$ and $Q^3$ are CH; $Q^1$ is N, and $Q^2$ and $Q^3$ are CH; $Q^2$ is N, and $Q^1$ and $Q^3$ are CH; $Q^1$ and $Q^2$ are CH, and $Q^3$ are N; and $Q^1$ and $Q^2$ are N, and $Q^3$ are CH. CX is preferably CF. Further preferred are compounds wherein $Q^2$ is nitrogen or CF.

According to a further aspect of the invention, preferred are N-oxide compounds of formula I, that is compounds of formula I wherein independently $Q^1$, $Q^2$ or $Q^3$ is N-oxide and/or $R^3$ is azaheterocyclyl having an imine moiety thereof as an N-oxide. Further preferred are compounds of formula I wherein $Q^1$ and $Q^3$ are CH, and $Q^2$ is an N-oxide. Also further preferred are compounds of formula I wherein $R^3$ is 3,5-dihalo-1-oxido-4-pyridinium.

Compounds of the invention wherein $R^1$ is lower alkyl optionally substituted by one or more halo, preferably fluoro, are also preferred. Compounds of the invention wherein $R^2$ is substituted by one or more halo, preferably fluoro, are also preferred. It is further preferred that the halo substitution is on a position of $R^1$ or $R^2$ that is attached respectively to $Z^1$ and $Z^2$. Where $R^2$ is cyclothioalkyl or cyclothioalkenyl substituted by halo, it is also preferred that the halo substitution is on a position adjacent to the thio moiety of the cyclothioalkyl or cyclothioalkenyl.

Among the compounds of the invention wherein $R^3$ is substituted phenyl, the phenyl group is preferably substituted on the 2-position or on both the 2- and 6-positions; more preferably on both the 2- and 6-positions. It is also preferred that the phenyl substituent is halo; preferably chloro or fluoro.

Similarly, among compounds of the invention where $R^3$ is substituted heteroaryl, the heteroaryl group is preferably substituted on one or both, more preferably on both, of the positions adjacent to a position of $R^3$ that is attached to $Z^3$.

Special embodiments of the compounds of the invention include those of formula I wherein $R^3$ is azaheteroaryl substituted on one or both, more preferably on both, of the positions adjacent to a position of $R^3$ that is attached to $Z^3$, or an N-oxide thereof. Further preferred are compounds wherein $R^3$ is a 3,5-dihalopyrid-4-yl moiety, preferably wherein halo is chloro or fluoro, or an N-oxide thereof.

Special embodiments of the compounds of the invention also include those of formula I wherein $Z^3$ is —CZNH— or —CZCH$_2$—, more preferably wherein Z is oxygen.

Special embodiments of the compounds of the present invention include those wherein $R^2$ is isopropyl, cyclopropylmethyl, cyclopentyl, trinorbornyl, trinorbornenyl, tricyclo[2.2.1.0$^{2.6}$]heptanyl and tetrahydrothiophenyl.

Another special embodiment of the compounds of the invention include those of formula I wherein $R^1$ is lower alkyl optionally substituted by halo, preferably fluoro; and $R^2$ is isopropyl, cyclopropylmethyl, cyclopentyl, trinorbornyl, trinorbornenyl, tricyclo[2.2.1.0$^{2.6}$]heptanyl and tetrahydrothiophenyl.

According to a further aspect of the invention, preferred compounds of formula I are described wherein $Z^1$ and $Z^2$ are oxygen, and $Z^1$ is sulfur and $Z^2$ is oxygen are preferred. More preferred are where $Z^1$ and $Z^2$ are oxygen.

Preferred compounds for use according to the invention are selected from the following:

A  N-(3,5-dichloropyrid-4-yl)-3-cyclopentyloxy-6-fluoro-4-methoxybenzamide;
B  N-(2,6-difluorophenyl)-3-cyclopentyloxy-6-fluoro-4-methoxybenzamide;
C  N-(2-chloro-6-fluorophenyl)-3-cyclopentyloxy-6-fluoro-4-methoxybenzamide;
D  N-(2-trifluoromethylphenyl)-3-cyclopentyloxy-6-fluoro-4-methoxybenzamide;
E  N-(2,4,6-trichlorophenyl)-3-cyclopentyloxy-6-fluoro-4-methoxybenzamide;
F  N-(2,6-dibromophenyl)-3-cyclopentyloxy-6-fluoro-4-methoxybenzamide;
G  N-(2-chloro-6-methylphenyl)-3-cyclopentyloxy-6-fluoro-4-methoxybenzamide;
H  N-(2,6-dichlorophenyl)-3-cyclopentyloxy-6-fluoro-4-methoxybenzamide;
I  N-(2-fluorophenyl)-3-cyclopentyloxy-6-fluoro-4-methoxybenzamide;
J  N-phenyl-3-cyclopentyloxy-6-fluoro-4-methoxybenzamide;
K  N-(2-methoxyphenyl)-3-cyclopentyloxy-6-fluoro-4-methoxybenzamide;
L  N-(2-chlorophenyl)-3-cyclopentyloxy-6-fluoro-4-methoxybenzamide;
M  N-(3-chlorophenyl)-3-cyclopentyloxy-6-fluoro-4-methoxybenzamide;
N  N-(4-methoxyphenyl)-3-cyclopentyloxy-6-fluoro-4-methoxybenzamide;
O  N-(2,6-dimethylphenyl)-3-cyclopentyloxy-6-fluoro-4-methoxybenzamide;
P  N-(2-methylthiophenyl)-3-cyclopentyloxy-6-fluoro-4-methoxybenzamide;
Q  N-(2-bromophenyl)-3-cyclopentyloxy-6-fluoro-4-methoxybenzamide;
R  N-(2-methoxycarbonylphenyl)-3-cyclopentyloxy-6-fluoro-4-methoxybenzamide;
S  N-(2-aminosulfonylphenyl)-3-cyclopentyloxy-6-fluoro-4-methoxybenzamide;
T  N-(2-benzoylphenyl)-3-cyclopentyloxy-6-fluoro-4-methoxybenzamide;
U  N-(2-cyanophenyl)-3-cyclopentyloxy-6-fluoro-4-methoxybenzamide;
V  N-(2,5-dichlorophenyl)-3-cyclopentyloxy-6-fluoro-4-methoxybenzamide;
W  N-(3-methylphenyl)-3-cyclopentyloxy-6-fluoro-4-methoxybenzamide;
X  N-(2-nitrophenyl)-3-cyclopentyloxy-6-fluoro-4-methoxybenzamide;
Y  N-(2-dimethylaminophenyl)-3-cyclopentyloxy-6-fluoro-4-methoxybenzamide;
Z  N-(2-acetylphenyl)-3-cyclopentyloxy-6-fluoro-4-methoxybenzamide;
AA  N-(2-hydroxyphenyl)-3-cyclopentyloxy-6-fluoro-4-methoxybenzamide;
AB  N-(4-chloropyrid-3-yl)-3-cyclopentyloxy-6-fluoro-4-methoxybenzamide;
AC  N-pyrid-2-yl-3-cyclopentyloxy-6-fluoro-4-methoxybenzamide;
AD  N-pyrazin-2-yl-3-cyclopentyloxy-6-fluoro-4-methoxybenzamide;
AE  N-pyrimidin-2-yl-3-cyclopentyloxy-6-fluoro-4-methoxybenzamide;
AF  N-(3-methylpyrid-2-yl)-3-cyclopentyloxy-6-fluoro-4-methoxybenzamide;
AG  N-pyrid-3-yl-3-cyclopentyloxy-6-fluoro-4-methoxybenzamide;
AH  N-(3-chloropyrid-2-yl)-3-cyclopentyloxy-6-fluoro-4-methoxybenzamide;
AI  N-(3-chloropyrid-4-yl)-3-cyclopentyloxy-6-fluoro-4-methoxybenzamide;

AJ N-pyrid-4-yl-3-cyclopentyloxy-6-fluoro-4-methoxybenzamide;
AK N-(3,5-dimethylisoxazol-4-yl)-3-cyclopentyloxy-6-fluoro-4-methoxybenzamide;
AL N-(3,5-dibromopyrid-4-yl)-3-cyclopentyloxy-6-fluoro-4-methoxybenzamide;
AM N-(3,5-dimethylpyrid-4-yl)-3-cyclopentyloxy-6-fluoro-4-methoxybenzamide;
AN N-(2,6-dichloro-4-cyanophenyl)-3-cyclopentyloxy-6-fluoro-4-methoxybenzamide;
AO N-(2,6-dichloro-4-methoxycarbonylphenyl)-3-cyclopentyloxy-6-fluoro-4-methoxybenzamide;
AP N-(2,3,5-trifluoropyrid-4-yl)-3-cyclopentyloxy-6-fluoro-4-methoxybenzamide;
AQ N-(2,6-dichloro-4-ethoxycarbonylphenyl)-3-cyclopentyloxy-6-fluoro-4-methoxybenzamide;
AR N-(2,6-dichloro-4-nitrophenyl)-3-cyclopentyloxy-6-fluoro-4-methoxybenzamide;
AS N-(3,5-difluoropyrid-4-yl)-3-cyclopentyloxy-6-fluoro-4-methoxybenzamide;
AT N-(3-bromo-5-chloropyrid-4-yl)-3-cyclopentyloxy-6-fluoro-4-methoxybenzamide;
AU N-(2,4,6-trifluorophenyl)-3-cyclopentyloxy-6-fluoro-4-methoxybenzamide;
AV N-(2,6-dichloro-4-methoxyphenyl)-3-cyclopentyloxy-6-fluoro-4-methoxybenzamide;
AW N-(4,6-dichloropyrimid-5-yl)-3-cyclopentyloxy-6-fluoro-4-methoxybenzamide;
AX N-(2,3,5,6-tetrafluoropyrid-4-yl)-3-cyclopentyloxy-6-fluoro-4-methoxybenzamide;
AY N-(3,5-dichloro-2,6-difluoropyrid-4-yl)-3-cyclopentyloxy-6-fluoro-4-methoxybenzamide;
AZ N-(5-cyano-3-methylisothiazol-4-yl)-3-cyclopentyloxy-6-fluoro-4-methoxybenzamide;
BA N-(2,6-dichloro-4-carbamoylphenyl)-3-cyclopentyloxy-6-fluoro-4-methoxybenzamide;
BB N-(3-chloro-2,5,6-trifluoropyrid-4-yl)-3-cyclopentyloxy-6-fluoro-4-methoxybenzamide;
BC N-(4-nitrophenyl)-3-cyclopentyloxy-6-fluoro-4-methoxybenzamide;
BD N-(3-methyl-5-bromoisothiazol-4-yl)-3-cyclopentyloxy-6-fluoro-4-methoxybenzamide;
BE N-(3,5-dimethylisothiazol-4-yl)-3-cyclopentyloxy-6-fluoro-4-methoxybenzamide;
BF N-(2,6-difluorophenyl)-3-cyclohexyloxy-6-fluoro-4-methoxybenzamide;
BG N-(2,6-difluorophenyl)-3-butoxy-6-fluoro-4-methoxybenzamide;
BH N-(2,6-difluorophenyl)-3-propoxy-6-fluoro-4-methoxybenzamide;
BJ N-(3,5-dichloropyrid-4-yl)-3-cyclopent-2-enyloxy-6-fluoro-4-methoxybenzamide;
BL N-(3,5-dichloropyrid-4-yl)-3-cyclopent-3-enyloxy-6-fluoro-4-methoxybenzamide;
BN N-(2-methylsulfonylphenyl)-3-cyclopentyloxy-6-fluoro-4-methoxybenzamide;
BP N-(2-chlorophenyl)-3-cyclopentyloxy-6-fluoro-4-methoxy(thiobenzamide);
BR N-(3,5-dichloropyrid-4yl)-3-cyclopentyloxy-6-fluoro-4-methoxy(thiobenzamide);
BT N-(3,5-dichloropyrid-4yl)-3-cyclopentyloxy-6-fluoro-4-methoxy(thiobenzamide);
BV N-(2,6-dichloro-4-acetylaminophenyl)-3-cyclopentyloxy-6-fluoro-4-methoxybenzamide;
BX N-(2,6-dichloro-4-hydroxymethylphenyl)-3-cyclopentyloxy-6-fluoro-4-methoxybenzamide;
BZ N-(2,6-dichloro-4-formylphenyl)-3-cyclopentyloxy-6-fluoro-4-methoxybenzamide;
CB sodium salt of N-(3,5-dichloropyrid-4-yl)-3-cyclopentyloxy-6-fluoro-4-methoxybenzamide;
CC (±)N-(3,5-dichloropyrid-4-yl)-3-exonorbornyloxy-6-fluoro-4-methoxybenzamide;
CD N-(3,5-dichloropyrid-4-yl)-2-fluoro-5-isopropyloxy-4-methoxybenzamide;
CE (±)N-(3,5-dichloropyrid-4-yl)-2-fluoro-4-methoxy-5-(tricyclo[2.2.1.0]hept-2-yloxy)benzamide hemihydrate;
CF N-(3,5-dichloropyrid-4-yl)-3-cyclopentyloxy-4-difluoromethoxy-6-fluorobenzamide
CG N-(3,5-dichloropyrid-4-yl)-4-difluoromethoxy-2-fluoro-5-isopropyloxybenzamide;
CH 2-(3,5-dichloropyrid-4-yl)-1-(3-cyclopentyloxy-6-fluoro-4-methoxyphenyl)ethanone;
CI N-(3,5-dichloro-1-oxido-4-pyridinio)-2-fluoro-5-isopropyloxy-4-methoxybenzamide;
CJ (±)N-(3,5-dichloro-1-oxido-4-pyridinio)-3-exo-(8,9,10-trinorbornyloxy)-6-fluoro-4-methoxybenzamide;
CK N-(3,5-dichloro-1-oxido-4-pyridinio)-3-cyclopentyloxy-6-fluoro-4-methoxybenzamide;
CL N-(3,5-dichloro-1-oxido-4-pyridinio)-3-cyclopentyloxy-4-difluoromethoxy-6-fluorobenzamide;
CM N-(3,5-dichloro-1-oxido-4-pyridinio)-4-difluoromethoxy-2-fluoro-5-isopropyloxybenzamide;
CN 2-(3,5-Dichloro-1-oxido-4-pyridinio)-1-(3-cyclopentyloxy-6-fluoro-4-methoxyphenyl)ethanone;
CO 5-cyclopentyloxy-N-(3,5-dichloropyrid-4-yl)-6-methoxynicotinamide;
CP N-(2,6-dichlorophenyl)-5-cyclopentyloxy-6-methoxynicotinamide;
CQ 5-cyclopentyloxy-N-(3,5-dimethylisoxazol-4-yl)-6-methoxynicotinamide
CR 5-cyclopentyloxy-N-(3,5-difluoropyrid-4-yl)-6-methoxynicotinamide
CS 6-cyclopentyloxy-N-(3,5-dichloropyrid-4-yl)-5-methoxypyridine-2-carboxamide;
CT 1-(5-cyclopentyloxy-6-methoxypyridin-3-yl)-2-(3,5-dichloropyrid-4-yl)ethanone;
CU 5-cyclopentyloxy-N-(3,5-dichloro-4-pyridyl)-6-methylthionicotinamide;
CV N-(3,5-dichloro-4-pyridyl)-5-isopropyloxy-6-methylthionicotinamide;
CW 2-(3,5-dichloro-4-pyridyl)-1-(5-isopropyloxy-6-methylthio-3-pyridyl)ethanone;
CX 1-(5-cyclopentyloxy-6-methoxypyrid-3-yl)-2-(3,5-dichloro-1-oxido-4-pyridinio)ethanone hemihydrate;
CY (±)-N-(3,5-dichloropyrid-4-yl)-6-methoxy-5-exo-(8,9,10-trinorborn-5-en-2-yloxy)nicotinamide;
CZ (±)-N-(3,5-dichloropyrid-4-yl)-6-methoxy-5-(tricyclo[2.2.1.0.$^{2.6}$]hept-2-yloxy)nicotinamide monohydrate;
DA N-(3,5-dichloropyrid-4-yl)-4-cyclopentyloxy-5-methoxypyridine-2-carboxamide;
DB N-(2,6-difluorophenyl)-4-cyclopentyloxy-5-methoxypyridine-2-carboxamide;
DC N-(2-chloro-6-fluorophenyl)-4-cyclopentyloxy-5-methoxypyridine-2-carboxamide;
DD N-(2-trifluoromethylphenyl)-4-cyclopentyloxy-5-methoxypyridine-2-carboxamide;
DE N-(2,4,6-trichlorophenyl)-4-cyclopentyloxy-5-methoxypyridine-2-carboxamide;
DF N-(2,6-dibromophenyl)-4-cyclopentyloxy-5-methoxypyridine-2-carboxamide;
DG N-(2-chloro-6-methylphenyl)-4-cyclopentyloxy-5-methoxypyridine-2-carboxamide;

DH N-(2,6-dichlorophenyl)-4-cyclopentyloxy-5-methoxypyridine-2-carboxamide;

DI N-(2-fluorophenyl)-4-cyclopentyloxy-5-methoxypyridine-2-carboxamide;

DJ N-phenyl-4-cyclopentyloxy-5-methoxypyridine-2-carboxamide;

DK N-(2-methoxyphenyl)-4-cyclopentyloxy-5-methoxypyridine-2-carboxamide;

DL N-(2-chlorophenyl)-4-cyclopentyloxy-5-methoxypyridine-2-carboxamide;

DM N-(3-chlorophenyl)-4-cyclopentyloxy-5-methoxypyridine-2-carboxamide;

DN N-(4-methoxyphenyl)-4-cyclopentyloxy-5-methoxypyridine-2-carboxamide;

DO N-(2,6-dimethylphenyl)-4-cyclopentyloxy-5-methoxypyridine-2-carboxamide;

DP N-(2-methylthiophenyl)-4-cyclopentyloxy-5-methoxypyridine-2-carboxamide;

DQ N-(2-bromophenyl)-4-cyclopentyloxy-5-methoxypyridine-2-carboxamide;

DR N-(2-methoxycarbonylphenyl)-4-cyclopentyloxy-5-methoxypyridine-2-carboxamide;

DS N-(2-aminosulfonylphenyl)-4-cyclopentyloxy-5-methoxypyridine-2-carboxamide;

DT N-(2-benzoylphenyl)-4-cyclopentyloxy-5-methoxypyridine-2-carboxamide;

DU N-(2-cyanophenyl)-4-cyclopentyloxy-5-methoxypyridine-2-carboxamide;

DV N-(2,5-dichlorophenyl)-4-cyclopentyloxy-5-methoxypyridine-2-carboxamide;

DW N-(3-methylphenyl)-4-cyclopentyloxy-5-methoxypyridine-2-carboxamide;

DX N-(2-nitrophenyl)-4-cyclopentyloxy-5-methoxypyridine-2-carboxamide;

DY N-(2-dimethylaminophenyl)-4-cyclopentyloxy-5-methoxypyridine-2-carboxamide;

DZ N-(2-acetylphenyl)-4-cyclopentyloxy-5-methoxypyridine-2-carboxamide;

EA N-(2-hydroxyphenyl)-4-cyclopentyloxy-5-methoxypyridine-2-carboxamide;

EB N-(4-chloropyrid-3-yl)-4-cyclopentyloxy-5-methoxypyridine-2-carboxamide;

EC N-pyrid-2-yl-4-cyclopentyloxy-5-methoxypyridine-2-carboxamide;

ED N-pyrazin-2-yl-4-cyclopentyloxy-5-methoxypyridine-2-carboxamide;

EE N-pyrimidin-2-yl-4-cyclopentyloxy-5-methoxypyridine-2-carboxamide;

EF N-(3-methylpyrid-2-yl)-4-cyclopentyloxy-5-methoxypyridine-2-carboxamide;

EG N-pyrid-3-yl-4-cyclopentyloxy-5-methoxypyridine-2-carboxamide;

EH N-(3-chloropyrid-2-yl)-4-cyclopentyloxy-5-methoxypyridine-2-carboxamide;

EI N-(3-chloropyrid-4-yl)-4-cyclopentyloxy-5-methoxypyridine-2-carboxamide;

EJ N-pyrid-4-yl-4-cyclopentyloxy-5-methoxypyridine-2-carboxamide;

EK N-(3,5-dimethylisoxazol-4-yl)-4-cyclopentyloxy-5-methoxypyridine-2-carboxamide;

EL N-(3,5-dibromopyrid-4-yl)-4-cyclopentyloxy-5-methoxypyridine-2-carboxamide;

EM N-(3,5-dimethylpyrid-4-yl)-4-cyclopentyloxy-5-methoxypyridine-2-carboxamide;

EN N-(2,6-dichloro-4-cyanophenyl)-4-cyclopentyloxy-5-methoxypyridine-2-carboxamide;

EO N-(2,6-dichloro-4-methoxycarbonylphenyl)-4-cyclopentyloxy-5-methoxypyridine-2-carboxamide;

EP N-(2,3,5-trifluoropyrid-4-yl)-4-cyclopentyloxy-5-methoxypyridine-2-carboxamide;

EQ N-(2,6-dichloro-4-ethoxycarbonylphenyl)-4-cyclopentyloxy-5-methoxypyridine-2-carboxamide;

ER N-(2,6-dichloro-4-nitrophenyl)-4-cyclopentyloxy-5-methoxypyridine-2-carboxamide;

ES N-(3,5-difluoropyrid-4-yl)-4-cyclopentyloxy-5-methoxypyridine-2-carboxamide;

ET N-(3-bromo-5-chloropyrid-4-yl)-4-cyclopentyloxy-5-methoxypyridine-2-carboxamide;

EU N-(2,4,6-trifluorophenyl)-4-cyclopentyloxy-5-methoxypyridine-2-carboxamide;

EV N-(2,6-dichloro-4-methoxyphenyl)-4-cyclopentyloxy-5-methoxypyridine-2-carboxamide;

EW N-(4,6-dichloropyrimid-5-yl)-4-cyclopentyloxy-5-methoxypyridine-2-carboxamide;

EX N-(2,3,5,6-tetrafluoropyrid-4-yl)-4-cyclopentyloxy-5-methoxypyridine-2-carboxamide;

EY N-(3,5-dichloro-2,6-difluoropyrid-4-yl)-4-cyclopentyloxy-5-methoxypyridine-2-carboxamide;

EZ N-(5-cyano-3-methylisothiazol-4-yl)-4-cyclopentyloxy-5-methoxypyridine-2-carboxamide;

FA N-(2,6-dichloro-4-carbamoylphenyl)-4-cyclopentyloxy-5-methoxypyridine-2-carboxamide;

FB N-(3-chloro-2,5,6-trifluoropyrid-4-yl)-4-cyclopentyloxy-5-methoxypyridine-2-carboxamide;

FC N-(4-nitrophenyl)-4-cyclopentyloxy-5-methoxypyridine-2-carboxamide;

FD N-(3-methyl-5-bromoisothiazol-4-yl)-4-cyclopentyloxy-5-methoxypyridine-2-carboxamide;

FE N-(3,5-dimethylisothiazol-4-yl)-4-cyclopentyloxy-5-methoxypyridine-2-carboxamide;

FF N-(3,5-dichloro-1-oxido-4-pyridinio)-4-cyclopentyloxy-5-methoxypyridine-2-carboxamide;

FG 1-(4-cyclopentyloxy-5-methoxypyridin-2-yl)-2-(3,5-dichloropyridin-4-yl)ethanone;

FH (±)-N-(3,5-difluoropyrid-4-yl)-6-methoxy-5-exo-(8,9,10-trinorborn-2-yloxy)nicotinamide;

FI (±)-N-(3,5-dichloropyridin-4-yl)-6-methoxy-5-exo-(8,9,10-trinorborn-2-yloxy)nicotinamide;

FJ (±)-N-(3,5-dichloropyrid-4-yl)-5-methoxy-4-(tricyclo[2.2.1.0$^{2.6.}$]hept-2-yloxy)pyridine-2-carboxamide;

FK (±)-N-(3,5-difluoropyrid-4-yl)-5-methoxy-4-(tricyclo[2.2.1.0$^{2.6.}$]hept-2-yloxy)pyridine-2-carboxamide hydrate;

FL (±)-N-(3,5-dichloropyridin-4-yl)-5-methoxy-4-(tetrahydrothiophen-3-yloxy)pyridine-2-carboxamide;

FM N-(3,5-dichloropyridin-4-yl)-4-cyclopropylmethoxy-5-methoxypyridine-2-carboxamide;

FN N-(3,5-dichloropyridin-4-yl)-4-isopropyloxy-5-methoxypyridine-2-carboxamide;

FO (±)-N-(3,5-dichloro-1-oxido-4-pyridinio)-5-methoxy-4-(tricyclo[2.2.1.0$^{2.6.}$]-hept-2-yloxy)pyridine-2-carboxamide;

FP (±)-N-(3,5-difluoro-1-oxido-4-pyridinio)-5-methoxy-4-(tricyclo[2.2.1.0$^{2.6.}$]-hept-2-yloxy)pyridine-2-carboxamide;

FQ N-(3,5-dichloro-1-oxido-4-pyridinio)-4-isopropyloxy-5-methoxypyridine-2-carboxamide;

FR N-(3,5-dichloro-1-oxido-4-pyridinio)-4-cyclopropylmethoxy-5-methoxypyridine-2-carboxamide hemihydrate;

FS (±)-N-(3,5-dichloro-1-oxido-4-pyridinio)-5-methoxy-4-(tetrahydrothiophen-3-yloxy)pyridine-2-carboxamide;

FT N-(3,5-dichloro-1-oxido-4-pyridinio)-4-cyclopentyloxy-5-methoxy-1-oxidopyridinium-2-carboxamide;
FU N-(3,5-dichloro-1-oxido-4-pyridinio)-4-cyclopropylmethoxy-5-methoxy-1-oxidopyridinium-2-carboxamide;
FV N-(3,5-dichloro-1-oxido-4-pyridinio)-4-isopropyloxy-5-methoxy-1-oxidopyridinium-2-carboxamide;
FW 1-(5-methoxy-4-(tricyclo[2.2.1.0.$^{2.6}$]hept-2-yloxy)pyridin-2-yl)-2-(3,5-dichloropyridin-4-yl)ethanone;
FX (±)-1-(5-methoxy-4-(tetrahydrothiophen-3-yloxy)pyridin-2-yl)-2-(3,5-dichloropyridin-4-yl)ethanone;
FY 1-(4-(tricyclo[2.2.1.0.$^{2.6}$]hept-2-yloxy)-5-methoxypyridin-2-yl)-2-(3,5-dichloro-1-oxido-4-pyridinio)ethanone;
FZ N-(3,5-dichloropyridin-4-yl)-4-cyclopropylmethoxy-5-methoxy-1-oxidopyridinium-2-carboxamide;
GA N-(3,5-dichloropyridin-4-yl)-4-isopropyloxy-5-methoxy-1-oxidopyridinium-2-carboxamide;
GB N-(3,5-dichloropyridin-4-yl)-4-cyclopentyloxy-5-methoxy-1-oxidopyridinium-2-carboxamide hemihydrate;
GD N-(2-chlorophenyl)-3-cyclopentyloxy-6-fluoro-4-methoxybenzylamine;
GE N-(2-chlorophenyl)-4-cyclopentyloxy-5-methoxy-2-aminomethylpyridine;
GG trans-2-(2,6-dichlorophenyl)-1-(3-cyclopentyloxy-6-fluoro-4-methoxyphenyl)ethene;
GH trans-1-(3-cyclopentyloxy-6-fluoro-4-methoxyphenyl)-2-(2,6-difluorophenyl)ethene;
GI trans-2-(2,6-dichlorophenyl)-1-(4-cyclopentyloxy-5-methoxypyrid-2-yl)ethene;
GJ trans-1-(4-cyclopentyloxy-5-methoxypyrid-2-yl)-2-(2,6-difluorophenyl)ethene;
GL 1-[(3-cyclopentyloxy-6-fluoro-4-methoxy)phenyl]-2-(pyrid-4-yl)ethane-1,2-dione;
GM 1-(4-cyclopentyloxy-5-methoxypyrid-2-yl)-2-(pyrid-4-yl)ethane-1,2-dione;
GN N-(3,5-dichloropyrid-4-yl)-5-cyclopentyloxy-6-methoxypyridazine-3-carboxamide;
GO N-(3,5-dichloropyridin-4-yl)-4-cyclopentyloxy-5-difluoromethoxypyridine-2-carboxamide;
GP N-(3,5-dichloro-1-oxido-4-pyridinio)-4-cyclopentyloxy-5-difluoromethoxypyridine-2-carboxamide;
GQ N-(3,5-dichloropyrid-4-yl)-4-cyclopentyloxy-5-difluoromethoxy-1-oxidopyridium-2-carboxamide;
GR N-(3,5-dichloro-1-oxido-4-pyridinio)-4-cyclopentyloxy-5-difluoromethoxy-1-oxidopyridium-2-carboxamide;
GS 1-(5-difluoromethoxy-4-(cyclopentyloxy)pyridin-2-yl)-2-(3,5-dichloropyridin-4-yl)ethanone;
GT 1-(5-difluoromethoxy-4-(cyclopentyloxy)-1-oxido-2-pyridium)-2-(3,5-dichloropyridin-4-yl)ethanone;
GU 1-(5-difluoromethoxy-4-(cyclopentyloxy)pyridin-2-yl)-2-(3,5-dichloro-1-oxido-4-pyridinio)ethanone;
GV 1-(5-difluoromethoxy-4-(cyclopentyloxy)-1-oxido-2-pyridium)-2-(3,5-dichloro-1-oxido-4-pyridinio)ethanone;
GW N-(3,5-dichloropyrid-4-yl)-5,6-dimethoxypyridazine-3-carboxamide; and
GX 1-(5,6-dimethoxypyridazine-3-pyridium)-2-(3,5-dichloropyridin-4-yl)ethanone.

Preferred compounds include A, CC, CD, CE, CF, CG, CH, CI, CJ, CK, CL, CM, CN, CO, CP, CQ, CR, CS, CT, CU, CV, CW, CX, CY, CZ, DA, DB, FF, FG, FH, FI, FJ, FK, FL, FM, FN, FO, FP, FQ, FR, FS, FT, FU, FV, FW, FX, FY, FZ, GA, GB, GN, GO, GP.

The letters A-GX are allocated to compounds for easy reference in this specification.

Compounds of formula I may be prepared by the application or adaptation of known methods, by which is meant methods used heretofore or described in the literature.

Thus, compounds of formula I wherein $R^1$, $R^2$, $R^3$, $Q^1$, $Q^2$, $Q^3$, $Z^1$ and

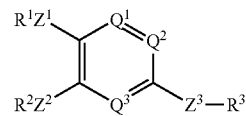

I $Z^2$ are as hereinbefore defined, $Z^3$ represents a —CZNH— linkage, and Z is oxygen, may be prepared by the reaction of compounds of formula II

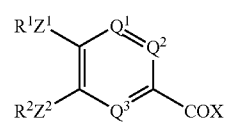

II wherein $R^1$, $R^2$, $Z^1$, $Z^2$, $Q^1$, $Q^2$ and $Q^3$ are as hereinbefore defined and X represents halo, such as bromo or, preferably, chloro, with a compound of the formula III wherein $R^3$ is as hereinbefore defined, preferably in the presence of

III a base such as an alkali metal hydride, such as sodium hydride, or an amine, preferably a tertiary amine, such as triethylamine or pyridine, optionally in an inert solvent, for example dichloromethane, dimethylformamide, or an ether, such as diethyl ether or tetrahydrofuran, preferably at a temperature from about 0° C. to the reflux temperature or at the melting point of the reaction mixture.

Alternatively, compounds of formula I wherein $R^1$, $R^2$, $R^3$, $Q^1$, $Q^2$, $Q^3$, $Z^1$ and $Z^2$ are as hereinbefore defined, $Z^3$ represents a —CZNH— linkage, and Z represents oxygen, may be prepared by the reaction of compounds of formula II as hereinbefore described, with a compound of the formula IV wherein $R^3$

IV is as hereinbefore defined, and $R^4$ represents an alkyl or cycloalkyl group containing up to 5 carbon atoms, preferably a methyl group, preferably in the presence of a base, for example an alkali metal hydride, such as sodium hydride, or an amine, preferably a tertiary amine, such as triethylamine, in an inert solvent, for example toluene, dimethylformamide, or an ether, such as tetrahydrofuran or diethyl ether, at a temperature from about 0° C. to reflux, then a second base, for example an amine, such as piperidine.

Alternatively, compounds of formula I, wherein $R^1$, $R^2$, $R^3$, $Q^1$, $Q^2$ and $Q^3$ are as hereinbefore defined, Z, $Z^1$ and $Z^2$ are oxygen, and $Z^3$ represents a —CZNH— linkage, may be prepared by the reaction of compounds of formula V hereinafter depicted, wherein $R^1$ and $R^2$ are as hereinbefore defined, $Q^1$, $Q^2$

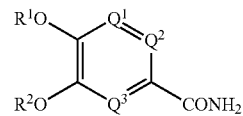

V and $Q^3$ are independently CH or N and at least one of $Q^1$, $Q^2$ and $Q^3$ is N, with compounds of formula VI wherein $R^3$ and X are as hereinbefore defined, $$R^3X \qquad \qquad VI$$

preferably X is chloro, and preferably the preparation takes place in the presence of a base, for example an alkali metal hydride, such as sodium hydride, an alkali metal alkoxide, such as potassium t-butoxide, an alkali metal hydroxide, such as sodium hydroxide or carbonate, or an amine, preferably a tertiary amine, such as triethylamine or pyridine, optionally in an inert solvent, for example dichloromethane, dimethylformamide, or an ether, such as diethyl ether or tetrahydrofuran, preferably at a temperature from about 0° C. to reflux.

Alternatively, compounds of formula I, wherein $R^1$, $R^2$, $R^3$, Z, $Z^1$, $Q^1$, $Q^2$ and $Q^3$ are as hereinbefore defined, $Z^3$ represents a —CZNH— linkage, and Z and $Z^2$ are oxygen, may be prepared by the reaction of compounds of formula VII wherein $R^1$, $R^3$, Z, $Z^1$, $Q^1$, $Q^2$ and $Q^3$ are as hereinbefore defined and

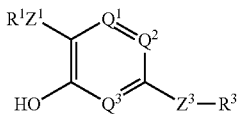

VII $Z^3$ represents a —CZNH— linkage, and Z is oxygen, with compounds of the formula VIII wherein $R^2$ is as hereinbefore defined, preferably, X is as $$R^2X \qquad \qquad VIII$$

hereinbefore defined or p-toluenesulfonate, preferably X is bromo, and preferably the preparation takes place in the presence of a base, for example an alkali metal hydride, such as sodium hydride, an alkali metal hydroxide or carbonate, such as sodium hydroxide or carbonate, or an amine, preferably a tertiary amine, such as. triethylamine or pyridine, optionally in an inert solvent, for example dichloromethane, dimethylformamide, or an ether, such as diethyl ether or tetrahydrofuran, preferably at a temperature from about 0° C. to reflux, or by the reaction of the compound of formula VII above with compounds of the formula XXI, as hereinbelow defined in the presence of, for example, diisopropylazodicarboxylate and triphenylphosphine.

Alternatively, compounds of formula I, wherein $R^1$, $R^2$, $R^3$, $Z^1$, $Z^2$, $Q^1$, $Q^2$ and $Q^3$ are as hereinbefore defined, $Z^3$ represents a —CZCH$_2$— linkage, and Z represents oxygen, are prepared from compounds of formula IX wherein $R^1$,

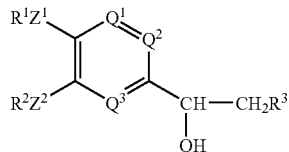

IX $R^2$, $R^3$, $Z^1$, $Z^2$, $Q^1$, $Q^2$ and $Q^3$ are as hereinbefore defined, by oxidation by the application or adaptation of known methods. The oxidation is carried out, for example, by reaction with oxalyl chloride and dimethyl sulfoxide, in the presence of a base, preferably a tertiary amine, preferably triethylamine, in an inert solvent such as dichloromethane, at temperatures from about −60° C. to about room temperature, preferably at a reduced temperature, or by adaptation of known methods for the preparation of ketone from a secondary alcohol, for example the application of pyridinium dichromate. Alternatively, the oxidation is carried out by reaction with chromium trioxide in the presence of 3,5-dimethylpyrazole.

According to a further feature of the present invention, compounds of formula I, wherein $R^1$, $R^2$, $R^3$, Z, $Z^1$, $Z^2$, $Q^1$, $Q^2$ and $Q^3$ are as hereinbefore defined, $Z^3$ represents a —CZCH$_2$— linkage, and preferably those wherein Z represents oxygen, are prepared from compounds of formula X wherein $R^1$,

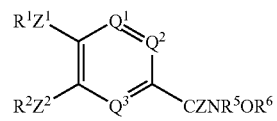

X $R^2$, Z, $Z^1$, $Z^2$, $Q^1$, $Q^2$ and $Q^3$ are as hereinbefore defined and $R^5$ and $R^6$ represent lower alkyl, such as methyl, groups, by coupling with compounds of the formula XI wherein $R^3$ is as hereinbefore defined, in the presence of a $$R^3CH_3 \qquad \qquad XI$$

strong base such as lithium diisopropylamide (usually prepared in situ from n-butyl lithium and diisopropylamine), preferably at a low temperature.

Alternatively, compounds of formula I, wherein $R^1$, $R^2$, $R^3$, $Z^1$, $Z^2$, $Q^1$, $Q^2$ and $Q^3$ are as hereinbefore defined, $Z^3$ represents a —CZCH$_2$— linkage, and Z represents oxygen, are prepared from compounds of formula XII wherein $R^1$,

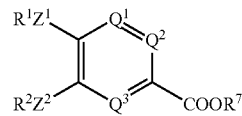

XII $R^2$, $Z^1$, $Z^2$, $Q^1$, $Q^2$ and $Q^3$ are as hereinbefore defined, and $R^7$ is alkyl, cycloalkyl or aralkyl containing up to 8 carbon atoms, by coupling with compounds of the formula XI above, wherein $R^3$ is as hereinbefore defined, in the presence of a strong base, such as an alkali metal amide or alkyl, for example n-butyl lithium or lithium diisopropylamide (usually prepared in situ from butyl lithium and diisopropylamine), in an inert solvent, for example cyclohexane or an ether, such as tetrahydrofuran or diethyl ether, at a temperature from about −78° C. to about room temperature.

According to a further feature of the present invention, compounds of formula I, wherein $R^1$, $R^2$, $R^3$, $Z^1$, $Z^2$, $Q^1$, $Q^2$ and $Q^3$ are as hereinbefore defined and $Z^3$ represents a —CH2-NH— linkage are prepared by the reaction of compounds of formula XIII wherein $R^1$, $R^2$, $Z^1$, $Z^2$, $Q^1$, $Q^2$ and $Q^3$ are as

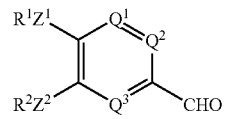

XIII hereinbefore defined, with compounds of formula III above, wherein $R^3$ is as hereinbefore defined, followed by reduction with a compound such as sodium cyanoborohydride. This process is especially suitable for compounds wherein $R^3$ represents an optionally substituted phenyl or naphthyl group.

According to a further feature of the present invention, compounds of formula I, wherein $R^1$, $R^2$, $R^3$, $Z^1$, $Z^2$, $Q^1$, $Q^2$ and $Q^3$ are as hereinbefore defined and $Z^3$ represents a —CH2-NH— linkage are prepared by the reaction of compounds of formula XIV wherein X, $R^1$, $R^2$, $Z^1$, $Z^2$, $Q^1$, $Q^2$ and $Q^3$ are as

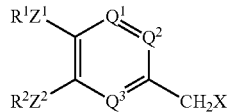
XIV hereinbefore defined, and X is preferably bromo, with compounds of formula III above, wherein $R^3$ is as hereinbefore defined, preferably in the presence of a base such as sodium hydride. This process is especially suitable for compounds wherein $R^3$ represents an optionally substituted heteroaryl group.

According to a further feature of the present invention, compounds of formula I, wherein $R^1$, $R^2$, $R^3$, $Z^1$, $Z^2$, $Q^1$, $Q^2$ and $Q^3$ are as hereinbefore defined and $Z^3$ represents a trans —CH=CH— linkage are prepared by the reaction of compounds of formula XIII above, wherein $R^1$, $R^2$, $Z^1$, $Z^2$, $Q^1$, $Q^2$ and $Q^3$ are as hereinbefore defined, with the reaction product of a compound of the formula XV wherein $R^3$ is as hereinbefore defined, $R^8$ represents $(R^8PCH_2R^3)^+(X)^-$ 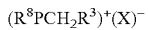 XV an aryl, such as phenyl group, and X represents halo, preferably bromo, with a base such as an alkali metal alkoxide, for example potassium t-butoxide. The reaction is preferably carried out in a solvent such as tetrahydrofuran.

According to a further feature of the present invention, compounds of formula I, wherein $R^1$, $R^2$, $R^3$, $Z^1$, $Z^2$, $Q^1$, $Q^2$ and $Q^3$ are as hereinbefore defined and $Z^3$ represents a —CF$_2$—O— linkage are prepared by the reaction of compounds of formula XVI, wherein $R^1$, $R^2$, $Z^1$, $Z^2$, $Q^1$, $Q^2$ and $Q^3$ are wherein

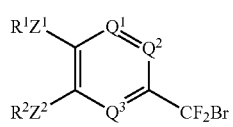
XVI $R^1$, $R^2$, $Z^1$, $Z^2$, $Q^1$, $Q^2$ and $Q^3$ are as hereinbefore defined, with compounds of the formula XVII wherein $R^3$ is as hereinbefore defined, preferably with the aid $R^3OH$  XVII of a base such as sodium hydride, preferably in a solvent such as tetrahydrofuran.

According to a further feature of the present invention, compounds of formula I, wherein $R^1$, $R^2$, $R^3$, $Z^1$, $Z^2$, $Q^1$, $Q^2$ and $Q^3$ are as hereinbefore defined and $Z^3$ represents a —CH$_2$—O— linkage are prepared by the reaction of compounds of formula XVIII wherein $R^1$, $R^2$, $Z^1$, $Z^2$, $Q^1$, $Q^2$ and $Q^3$ are as

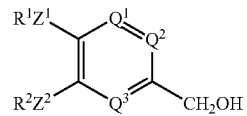
XVIII hereinbefore defined, with compounds of the formula VI hereinbefore, wherein $R^3$ and X are as hereinbefore defined, preferably with the aid of a base such as an alkali metal alkoxide, such as potassium t-butoxide. The reaction is preferably carried out in a solvent such as tetrahydrofuran.

According to a further feature of the present invention, compounds of formula I, wherein $R^1$, $R^2$, $R^3$, $Z^1$, $Z^2$, $Q^1$, $Q^2$ and $Q^3$ are as hereinbefore defined and $Z^3$ represents a —CH$_2$—O— linkage are prepared by the reaction of compounds of formula XIV above, wherein $R^1$, $R^2$, $Z^1$, $Z^2$, $Q^1$, $Q^2$, $Q^3$ and X are as hereinbefore defined, with compounds of formula XVII above, wherein $R^3$ is as hereinbefore defined, preferably with the aid of a base such as an alkali metal alkoxide, such as potassium t-butoxide.

According to a further feature of the present invention, compounds of formula I, wherein $R^1$, $R^2$, $R^3$, $Z^1$, $Z^2$, $Q^1$, $Q^2$ and $Q^3$ are as hereinbefore defined and $Z^3$ represents a —CO—CO— linkage are prepared by the oxidation of compounds of formula IX above, wherein $R^1$, $R^2$, $R^3$, $Z^1$, $Z^2$, $Q^1$, $Q^2$ and $Q^3$ are as hereinbefore defined, for example by reaction with pyridinium dichromate, preferably in a solvent such as dichloromethane. This reaction is particularly suitable for compounds wherein $R^3$ represents a heteroaryl, preferably an optionally substituted pyridyl, group.

According to a further feature of the present invention, compounds of formula I, wherein $R^1$, $R^2$, $R^3$, $Z^1$, $Z^2$, $Q^1$, $Q^2$ and $Q^3$ are as hereinbefore defined and $Z^3$ represents a —CH$_2$—S— linkage are prepared by the reaction of compounds of formula XIV above, wherein X, $R^1$, $R^2$, $Z^1$, $Z^2$, $Q^1$, $Q^2$ and $Q^3$ are as hereinbefore defined, with compounds of the formula XX wherein $R^3$ is $R^3$—SH  XX as hereinbefore defined, preferably with the aid of a base such as an alkali metal carbonate, such as potassium carbonate. Compounds of formula I wherein $Z^3$ is —CH$_2$—S—, preferably wherein Z, $Z^1$ and $Z^2$ each represent oxygen, and $R^2$ is alkyl or cycloalkyl, may then be oxidized to the corresponding sulphinyl or sulphonyl group. For example, the oxidation to —CH$_2$—SO— can be carried out by means of potassium hydrogen peroxomonosulfate in a medium such as aqueous methanol. For example, the oxidation to —CH$_2$—SO$_2$— can be carried out by means of sodium iodate in a medium such as aqueous methanol.

According to another feature of the invention, compounds of formula I wherein $R^1$, $R^2$, $R^3$, $Z^1$, $Z^3$, $Q^1$, $Q^2$ and $Q^3$ are as hereinbefore defined, and $R^2$ represents cyclosulphonylalkyl, cyclosulphinylalkyl, cyclosulphonylalkenyl or cyclosulphinylalkenyl, are prepared by oxidizing the corresponding compounds of formula I wherein $R^2$ represents cyclosulphonylalkyl or cyclosulphinylalkyl. For example, the oxidation to sulphinyl can be carried out by means of potassium hydrogen peroxomonosulfate in a medium such as aqueous methanol. For example, the oxidation to sulphonyl can be carried out by means of sodium iodate in a medium such as aqueous methanol.

As another example, compounds of formula I wherein $R^1$, $R^2$, $R^3$, $Z^1$, $Z^2$, $Q^1$, $Q^2$ and $Q^3$ are as hereinbefore defined, and $Z^3$ represents a cis —C═C— isomer linkage are prepared by the action of ultraviolet radiation upon the trans-isomer.

As another example, compounds of formula I wherein $R^1$, $R^2$, $R^3$, $Z^1$, $Z^1$, $Q^1$, $Q^2$ and $Q^3$ are as hereinbefore defined, and $Z^3$ contains a —CS— moiety, are prepared from compounds of formula I wherein $R^1$, $R^2$, $R^3$, $Z^1$, $Z^2$, $Q^1$, $Q^2$ and $Q^3$ are as hereinbefore defined, and $Z^3$ contains a —CO— moiety, by reaction with phosphorus pentasulfide or 2,4-bis(4-methoxyphenyl)-1,3-dithia-2,4-diphosphetane-2,4-disulfide, preferably in a solvent such as pyridine or toluene, and preferably at a temperature from about 0° C. to reflux.

As another example, compounds of formula I wherein $R^3$ is as hereinbefore defined and contains an alkylsulfonyl, arylsulfonyl, alkylsulfinyl or arylsulfinyl group, $R^1$, $R^2$, $Q^1$, $Q^2$, $Q^3$, Z, $Z^1$, $Z^2$ and $Z^3$ are as hereinbefore defined, are prepared by oxidising the corresponding compounds of formula I wherein $R^3$ is as hereinbefore defined and contains an alkylthio or arylthio group, $R^1$, $R^2$, $Q^1$, $Q^2$, $Q^3$, Z, $Z^1$, $Z^2$ and $Z^3$ are as hereinbefore defined, preferably wherein Z, $Z^1$ and $Z^2$ each represent oxygen, and $R^2$ is alkyl or cycloalkyl, preferably with a peroxyacid, such as 3-chloroperbenzoic acid, preferably in an inert solvent, such as dichloromethane, preferably at about room temperature. Alternatively, the oxidation is carried out by reaction with a peroxomonosulfate, such as potassium peroxomonosulfate, conveniently in a solvent such as methanol, buffered to about pH 5, at temperatures from about 0° C. to about room temperature. This latter method is preferred for compounds containing an acid-labile group, such as those wherein the moiety $R^2$ is unsaturated, such as a cyclopent-2-enyloxy group.

As another example, compounds of formula I wherein $R^3$ is as hereinbefore defined and contains a hydroxymethyl group, and $R^1$, $R^2$, $Q^1$, $Q^2$, $Q^3$, Z, $Z^1$, $Z^2$ and $Z^3$ are as hereinbefore defined, are prepared by the reduction of the corresponding compounds of formula I wherein $R^3$ is as hereinbefore defined and contains an aryloxycarbonyl or, preferably, alkoxycarbonyl group, $R^1$, $R^2$, $Q^1$, $Q^2$, $Q^3$, Z, $Z^1$, $Z^2$ and $Z^3$ are as hereinbefore defined, and Z is preferably oxygen, preferably by means of reacting an alkali metal borohydride, preferably in an inert solvent, such as tetrahydrofuran, preferably at about room temperature.

As another example, compounds of formula I wherein $R^3$ is as hereinbefore defined and contains a formyl group, and $R^1$, $R^2$, $Q^1$, $Q^2$, $Q^3$, Z, $Z^1$, $Z^2$ and $Z^3$ are as hereinbefore defined, are prepared by the oxidising the corresponding compounds of formula I wherein $R^3$ is as hereinbefore defined and contains a hydroxymethyl group, $R^1$, $R^2$, $Q^1$, $Q^2$, $Q^3$, Z, $Z^1$, $Z^2$ and $Z^3$ are as hereinbefore defined, and Z preferably being an oxygen atom, for example with oxalyl chloride and dimethyl sulfoxide, in a solvent such as dichloromethane, and preferably at a temperature lower than about −65° C., or, preferably, by reaction with a complex of sulfur trioxide with an amine such as pyridine, preferably in the presence of an amine such as triethylamine, preferably at about room temperature.

As another example, compounds of formula I wherein $R^3$ is as hereinbefore defined and contains an amino group, and $R^1$, $R^2$, $Q^1$, $Q^2$, $Q^3$, Z, $Z^1$, $Z^2$ and $Z^3$ are as hereinbefore defined, are prepared by the reducing the corresponding compounds of formula I wherein $R^3$ is as hereinbefore defined and contains a nitro group, $R^1$, $R^2$, $Q^1$, $Q^2$, $Q^3$, Z, $Z^1$, $Z^2$ and $Z^3$ are as hereinbefore defined, and Z is preferably oxygen, preferably with iron in acidic conditions, such as in acetic acid, preferably at or above room temperature, more especially at the reflux temperature. Alternatively the reduction are carried out by reaction with hydrazine hydrate in the presence of ferric chloride and activated carbon, conveniently in a solvent such as methanol, at temperatures from about 25° C. to about 80° C. This latter method is preferred for compounds containing an acid-labile group, such as those wherein the moiety $R^2$ is unsaturated, such as a cyclopent-2-enyloxy group.

As another example, compounds of formula I wherein $R^3$ is as hereinbefore defined and contains an alkanoylamino or aroylamino group, and $R^1$, $R^2$, $Q^1$, $Q^2$, $Q^3$, Z, $Z^1$, $Z^2$ and $Z^3$ are as hereinbefore defined, are prepared from compounds of formula I wherein $R^3$ is as hereinbefore defined and contains an amino group, $R^1$, $R^2$, $Q^1$, $Q^2$, $Q^3$, Z, $Z^1$, $Z^2$ and $Z^3$ are as hereinbefore defined, and Z is preferably oxygen, preferably by means of reaction with the appropriate acid halide or acid anhydride in the presence of a tertiary base, such as triethylamine, optionally in an inert solvent, and preferably at a temperature from about 0° C. to reflux.

Compounds of formula I wherein $R^3$ is as hereinbefore described, including an azaheteroaryl group containing one or more nitrogen ring atoms, preferably imine (═N—), and $R^1$, $R^2$, $Q^1$, $Q^2$, $Q^3$, Z, $Z^1$, $Z^2$ and $Z^3$ are as hereinbefore defined, may be converted to the corresponding compounds wherein a nitrogen atom of the azaheteroaryl moiety is oxidised to an N-oxide, $R^1$, $R^2$, $Q^1$, $Q^2$, $Q^3$, Z, $Z^1$, $Z^2$ and $Z^3$ are hereinbefore defined, and preferably Z, $Z^1$ and $Z^2$ each represent oxygen, and $R^2$ is alkyl or cycloalkyl, preferably by reacting a peracid, for example peracetic acid in acetic acid or m-chloroperoxybenzoic acid in an inert solvent such as dichloromethane, at a temperature from about room temperature to reflux, preferably at elevated temperature. Preferably wherein Z, $Z^1$ and $Z^2$ each represent oxygen, and $R^2$ is an oxidised cyclothioalkyl, such as cyclosulphinyl or sulphonyl, the reaction is carried out at a temperature from about room temperature to reflux, preferably at a reduced temperature. Alternatively, the oxidation is carried out by reaction with hydrogen peroxide in the presence of sodium tungstate at temperatures from about room temperature to about 60° C. This latter method is preferred for compounds containing an acid-labile group, such as those wherein the moiety $R^2$ contains a carbon-carbon double bond between its beta- and gamma-carbon atoms, such as a cyclopent-2-enyloxy group.

Compounds of formula I wherein $R^3$ represents an azaheteroaryl group containing a nitrogen ring atom as an N-oxide, and $R^1$, $R^2$, $Q^1$, $Q^2$, $Q^3$, Z, $Z^1$, $Z^2$ and $Z^3$ are as hereinbefore defined, may be converted to the corresponding compounds wherein $Q^1$, $Q^2$ or $Q^3$ as a nitrogen atom is oxidised to an N-oxide moiety, $R^1$, $R^2$, Z, $Z^1$, $Z^2$ and $Z^3$ are hereinbefore defined, and preferably wherein Z, $Z^1$ and $Z^2$ each represent oxygen, and $R^2$ is alkyl or cycloalkyl, by reacting a peracid, for example m-chloroperoxy-benzoic acid in an inert solvent such as dichloromethane, at a temperature from about room temperature to reflux, preferably at elevated temperature.

Compounds of formula I wherein $R^3$ represents a azaheteroaryl group containing one or more nitrogen ring atoms, preferably imine (═N—), and $R^1$, $R^2$, $Q^1$, $Q^2$, $Q^3$, Z, $Z^1$, $Z^2$ and $Z^3$ are as hereinbefore defined, may be converted to the corresponding compounds wherein a nitrogen atom of the azaheteroaryl moiety is oxidised to an N-oxide, wherein $Q^1$, $Q^2$ or $Q^3$ as a nitrogen atom is oxidised to an N-oxide moiety, $R^1$, $R^2$, Z, $Z^1$, $Z^2$ and $Z^3$ are hereinbefore defined, and preferably wherein Z, $Z^1$ and $Z^2$ each represent oxygen, and $R^2$ is alkyl or cycloalkyl, preferably by reacting a peracid, for example m-chloroperoxybenzoic acid in an inert solvent such as dichloromethane, at a temperature from about room temperature to reflux, preferably at elevated temperature.

Compounds of formula I wherein $R^3$ represents an azaheteroaryl group containing a nitrogen ring atom as an N-oxide, $Q^1$, $Q^2$ or $Q^3$ as a nitrogen atom is oxidised to an N-oxide moiety, and $R^1$, $R^2$, Z, $Z^1$, $Z^2$ and $Z^3$ are as hereinbefore defined, may be converted to the corresponding compounds wherein $R^3$ represents an azaheteroaryl group containing one or more nitrogen ring atoms, preferably imine (=N—), $Q^1$, $Q^2$ or $Q^3$ as a nitrogen atom is oxidised to an N-oxide moiety, $R^1$, $R^2$, Z, $Z^1$, $Z^2$ and $Z^3$ are hereinbefore defined, preferably by reacting in a deoxygenating system, for example diphosphorus tetraiodide in an inert solvent, such as dichloromethane, preferably at room temperature, or with a chlorotrialkylsilane, preferably chlorotrimethylsilane, in the presence of an alkali metal iodide, e.g potassium iodide, and zinc, in an inert solvent, for example acetonitrile, at temperatures from about 0° C. to about room temperature, preferably at reduced temperature.

For example, compounds of formula I wherein $R^1$ is as hereinbefore defined and is substituted by fluorine on a carbon atom thereof alpha to the attachment of $R^1$ to $Z^1$ as sulfur, or wherein $R^2$ is as hereinbefore defined and is substituted by fluorine on a carbon atom thereof alpha to the attachment of $R^2$ to $Z^2$ as sulfur, and $Q^1$, $Q^2$, $Q^3$, $R^3$ and $Z^3$ as hereinbefore defined, are prepared by reacting xenon difluoride with corresponding compounds of formula I wherein said alpha-carbon atoms carry hydrogen atoms instead of said fluorine atoms. The reaction is conveniently carried out in a solvent, such as dichloromethane, in the presence of a molecular sieve, and in an inert atmosphere, at a low temperature, such as at about 0° C. Alternatively, compounds of formula I wherein $R^1$ is a difluoromethyl group may be prepared by reacting a compound of formula I or precursor wherein $Z^1$ is hydroxy or thiol with $HCBrF_2$ in the presence of a strong base in an inert solvent.

As another example, compounds of formula I wherein $R^3$ represents a heteroaryl group containing one or more nitrogen ring atoms but carrying no halogen substituents, and $R^1$, $R^2$, $R^3$, $Z^1$, $Z^2$, $Z^3$, $Q^1$, $Q^2$ and $Q^3$ are as hereinbefore defined, are prepared by the reduction of the corresponding compounds of formula I wherein $R^3$ does carry one or more halo, such as chloro, substituents, for example by means of ammonium formate in the presence of a palladium catalyst.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on TNF and PDE inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrohalides, such as hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-beta-hydroxynaphthoates, gentisates, mesylates, isethionates and di-p-toluoyltartratesmethanesulfonate, ethanesulfonate, benzenesulfonate, p-toluenesulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, such as aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on TNF and PDE inherent in the free acid are not vitiated by side effects ascribable to the cations. Pharmaceutically acceptable salts, including for example alkali and alkaline earth metal salts, within the scope of the invention are those derived from the following bases; sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, such as hydrochloric acid.

As will be self-evident to those skilled in the art, some of the compounds of this invention do not form stable salts. However, acid addition salts are most likely to be formed by compounds of this invention wherein $R^3$ represents a nitrogen-containing heteroaryl group and/or wherein $R^3$ contains an amino group as a substituent. Preferable acid addition salts of the compounds of the invention are those wherein $R^2$ is other than an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

It will be apparent to those skilled in the art that certain compounds of formula I can exhibit isomerism, for example geometrical isomerism and optical isomerism. Optical isomers include compounds of the invention having asymmetric centers that may independently be in either the R or S configuration. Geometrical isomers include the cis and trans forms of compounds of the invention having alkenyl moieties. Individual geometrical isomers, stereoisomers and mixtures thereof are within the scope of the present invention.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The starting materials and intermediates are prepared by the application or adaptation of known methods, for example methods as described in the Reference Examples or their obvious chemical equivalents.

For example, compounds of formula II, wherein $R^1$, $R^2$, $Q^1$, $Q^2$, $Q^3$, $Z^1$ and $Z^2$ are as hereinbefore defined, are prepared from compounds of formula XIX wherein $R^1$, $R^2$, $Q^1$, $Q^2$, $Q^3$, $Z^1$ and $Z^2$ are as hereinbefore defined, by the

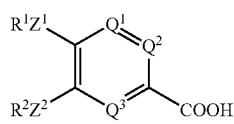

XIX application or adaptation of known methods for the preparation of acid halides from carboxylic acids. For example, when the moiety X in a compound of formula II represents a chloro, the reaction may be carried out by means of thionyl chloride or, preferably, oxalyl chloride in the presence of triethylamine, or as prepared by adaptation of the procedures described by K. R. Reistad et al., Acta. Chemica. Scandanavica B, 28, 667-72 (1974), incorporated herein by reference.

Compounds of formula XIX, wherein $R^1$, $R^2$, $Q^1$, $Q^2$, $Q^3$, $Z^1$ and $Z^2$ are as hereinbefore defined, are prepared by the oxidation of compounds of formula XIII above, wherein $R^1$, $R^2$, $Q^1$, $Q^2$, $Q^3$, $Z^1$ and $Z^2$ are as hereinbefore defined, for example by means of reaction with potassium permanganate, or with a mixture of sulfamic acid and sodium chlorite in acetic acid, or with sodium chlorite in the presence of sodium dihydrogen phosphate.

According to a further feature of the invention, compounds of formula XIX, wherein $R^1$, $R^2$, $Q^1$, $Q^2$, $Q^3$, $Z^1$ and $Z^2$ are as hereinbefore defined, are prepared by the oxidation of compounds of formula XVIII,

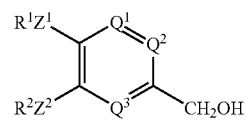

XVIII by adaptation of known methods for the preparation of carboxylic acids from primary alcohols, for example potassium permanganate in water or a mixture of water and inert organic solvent, e.g dichloromethane, in the presence of a phase transfer catalyst, such as aliquat 336, at about room temperature to reflux. Alternatively, the compound of formula XVIII is oxidized as described by H. C. Beyerman, Receueil, 77, 249-57, (1958), incorporated herein by reference.

Compounds of formula XIII, wherein $R^1$, $R^2$, $Q^1$, $Q^2$, $Q^3$, $Z^1$ and $Z^2$ are as hereinbefore defined, are prepared from compounds of formula XX

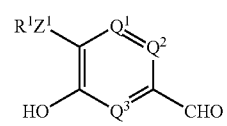

XX wherein $R^1$, $Q^1$, $Q^2$, $Q^3$ and $Z^1$ are as hereinbefore defined, by reaction with compounds of formula VIII wherein $R^2$ and X are as hereinbefore defined, and X is preferably bromo, preferably in the presence of a base, for example an alkali metal hydride, such as sodium hydride, an alkali metal hydroxide or carbonate, such as sodium hydroxide or carbonate, or an amine, preferably a tertiary amine, such as triethylamine or pyridine, optionally in an inert solvent, for example dichloromethane, dimethylformamide, or an ether, such as diethyl ether or tetrahydrofuran, preferably at a temperature from about 0° C. to reflux, or alternatively by reaction with compounds of the formula XXI, wherein $R^2$ is $R^2OH$      XXI as hereinbefore defined, preferably in the presence of a compound such as diisopropyl azodicarboxylate and triphenylphosphine.

Alternatively compounds of formula XIX above, wherein $R^1$, $R^2$, $Q^1$, $Q^2$, $Q^3$, $Z^1$ and $Z^2$ are as hereinbefore defined, are prepared by the hydrolysis of compounds of formula XII above, wherein $R^1$, $R^2$, $R^7$, $Q^1$, $Q^2$, $Q^3$, $Z^1$ and $Z^2$ are as hereinbefore defined, for example by reaction with a base, such as an aqueous alkali metal hydroxide, alkali metal carbonate or bicarbonate, such as potassium hydroxide or potassium carbonate, in an inert co-solvent such as methanol at a temperature from about room temperature to reflux, and then with an aqueous acid such as hydrochloric acid or acetic acid.

Compounds of formula XII above, wherein $R^1$, $R^2$, $R^7$, $Q^1$, $Q^2$, $Q^3$, $Z^1$ and $Z^2$ are as hereinbefore defined, are prepared from compounds of formula XXII

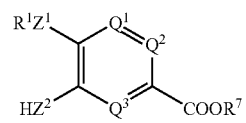

XXII by reaction with compounds of the formula XXI above, wherein $R^2$ is as wherein $R^1$, $R^7$, $Q^1$, $Q^2$, $Q^3$, $Z^1$ and $Z^2$ are as hereinbefore defined, preferably in the presence of diisopropyl azodicarboxylate and triphenylphosphine.

Alternatively, compounds of formula XII above, as hereinbefore defined, can be prepared from compounds of formula XXII above, as hereinbefore defined, by reaction with compounds of the formula VIII above, as hereinbefore defined, in the presence of base, for example an alkali metal hydride, such as sodium hydride, a tertiary amine, such as triethylamine, or preferably an alkali metal carbonate or hydroxide, such as sodium carbonate or hydroxide, or in the presence of a transition metal carbonate, such as silver carbonate, optionally in an inert solvent, such as dimethylformamide or tetrahydrofuran, preferably at a temperature from about 0° C. to about 80° C.

Compounds of formula IX above, wherein $R^1$, $R^2$, $R^3$, $Q^1$, $Q^2$, $Q^3$, $Z^1$, $Z^2$ and $Z^3$ are as hereinbefore defined, are prepared by the reaction of compounds of formula XIII above, wherein $R^1$, $R^2$, $Q^1$, $Q^2$, $Q^3$, $Z^1$ and $Z^1$ are as hereinbefore defined, with compounds of the formula XI above, wherein $R^3$ is as hereinbefore defined, in the presence of a base such as an alkali metal amide or alkyl, for example n-butyllithium or lithium diisopropylamide, in an inert solvent, for example cyclohexane or an ether, such as tetrahydrofuran or diethyl ether, at a temperature from about −78° C. to about room temperature, preferably at a reduced temperature.

Compounds of formula XVI above, wherein $R^1$, $R^2$, $Q^1$, $Q^2$, $Q^3$, $Z^1$ and $Z^2$ are as hereinbefore defined, are prepared by the reaction of bromine in carbon tetrachloride and ultraviolet radiation on the corresponding compounds wherein the bromodifluormethyl moiety is —$CHF_2$, which themselves are prepared by the action of sulfur tetrafluoride and hydrofluoric acid on compounds of formula XIII above, wherein $R^1$, $R^2$, $Q^1$, $Q^2$, $Q^3$, $Z^1$ and $Z^2$ are as hereinbefore defined, in the presence of pyridine.

Compounds of formula XIII above, wherein $R^1$, $R^2$, $Q^1$, $Q^2$, $Q^3$, $Z^1$ and $Z^2$ are as hereinbefore defined, are prepared from compounds of formula XVIII above, $R^1$, $R^2$, $Q^1$, $Q^2$, $Q^3$, $Z^1$ and $Z^2$ are as hereinbefore defined, by a Swern oxidation using a mixture of dimethyl sulphoxide and oxalyl chloride in the presence of a base, preferably a tertiary amine, preferably triethylamine, in an inert solvent e.g dichloromethane, at temperatures from about −60° C. to about room temperature, or preferably using activated manganese dioxide in an inert solvent, for example dichloromethane or diethyl ether, preferably at about room temperature.

Compounds of formula XXII above, wherein $R^1$, $R^7$, $Q^1$, $Q^2$, $Q^3$ and $Z^1$ are as hereinbefore defined, and $Z^2$ represents an oxygen atom are prepared from compounds of formula XXIII, wherein $R^1$, $R^7$, $Q^1$, $Q^2$, $Q^3$ and $Z^1$

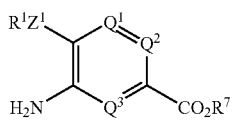

XXIII as hereinbefore described, by diazotisation of the amino group with an alkali metal nitrite, such as sodium nitrite, under aqueous acid conditions, such as aqueous hydrochloric acid, at room temperature or below, preferably at about 0° C. The diazo species is isolated by the addition of an alkali metal salt which stabilizes the diazonium salt, such as sodium tetrafluoroborate, at room temperature or below, preferably at about 0° C. The resulting stabilized diazonium salt is then decomposed under acid conditions, such as trifluoroacetic acid, at elevated temperature, such as boiling point of the acid.

Alternatively, compounds of formula XXII above, wherein $R^1$, $R^7$, $Q^1$, $Q^2$, $Q^3$ and $Z^1$ are as hereinbefore defined, and $Z^2$ represents a sulphur atom are prepared from compounds of formula XXIII above, wherein $R^1$, $R^7$, $Q^1$, $Q^2$, $Q^3$ and $Z^1$ are as hereinbefore defined, by diazotisation of the amino group with an alkali metal nitrite, such as sodium nitrite, under aqueous acid conditions, such as aqueous hydrochloric acid, at room temperature or below, preferably at about 0° C. The diazo species is isolated by the addition of an alkali metal salt which stabilizes the diazonium salt, such as sodium tetrafluoroborate, at room temperature or below, preferably at about 0° C. The resulting stabilized diazonium salt is then reacted with a sulphydryl anion, such as sodium hydrogen sulphide.

Compounds of formula XXIII above, wherein $R^1$, $R^7$, $Q^1$, $Q^2$, $Q^3$ and $Z^1$ are as hereinbefore defined, are prepared from compounds of formula XXIV

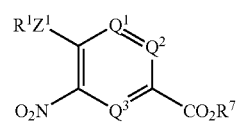

XXIV wherein $R^1$, $R^7$, $Q^1$, $Q^2$, $Q^3$ and $Z^1$ are as hereinbefore defined, by reduction of the nitro group with hydrogen and a metal catalyst, such as 5% palladium supported on carbon, in an inert solvent, such as ethyl acetate, or using a dissolving metal reduction, for example tin or zinc, preferably iron, in aqueous acid, for example hydrochloric acid, or preferably acetic acid, optionally with an inert co-solvent, for example ethanol, at a temperature from about room temperature to reflux, preferably at elevated temperature.

Compounds of formula XXIV above, wherein $R^1$, $R^7$, $Q^1$, $Q^2$, $Q^3$ and $Z^1$ are as hereinbefore defined, are prepared from compounds of formula XXV

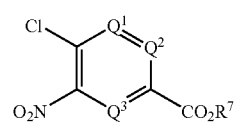

XXV wherein $R^7$, $Q^1$, $Q^2$ and $Q^3$ are as hereinbefore defined (prepared by the method of Berrie et al. J. Chem. Soc. 2590-4 (1951), Ger. Offen. 2,130,311 and U.S. Pat. No. 3,903,146, incorporated herein by reference), by reaction with compounds of formula XXVI, wherein $Z^1$ and $R^1$ are as hereinbefore defined, $R^1Z^1M$  XXVI and M represents an alkaline metal, such as sodium, in an alcohol, such as methanol where $Z^1$ is oxygen, or inert solvent, for example where $Z^1$ is sulphur, at room temperature or up to 80° C., preferably at room temperature.

Alternatively, compounds of formula XII above, wherein $Z^1$, $R^1$, and $R^7$ are as hereinbefore defined, and $Q^1$ and $Q^2$ are CH, and $Q^3$ is nitrogen are prepared by reaction of compounds of formula XXVII, wherein X, $Z^1$, $R^1$ and $R^7$

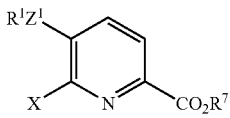

XXVII are as hereinbefore defined, with compounds of formula XXVI above, wherein $Z^2$, $R^2$ and M are as hereinbefore defined, preferably in the presence of a base, for example alkali metal or alkali metal hydride, such as sodium or sodium hydride, without co-solvent or in the presence of an inert solvent, such as tetrahydrofuran, from about room temperature to reflux, preferably at about room temperature.

Compounds of formula XXVII above, wherein $Z^1$, $R^1$ and $R^7$ are as defined hereinbefore, are prepared by the reaction of compounds of formula XXVIII, wherein X, $Z^1$ and $R^1$ are as hereinbefore defined, with compounds

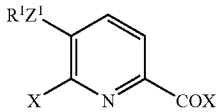

XXVIII of formula XXIX, wherein $R^7$ is as hereinbefore defined, preferably using the $R^7OH$     XXIX compound of XXIX as the solvent, from about room temperature to reflux.

Compounds of formula XXVIII above, wherein X, $R^1$ and $Z^1$ are as hereinbefore defined, are prepared from compounds of formula XXX, wherein

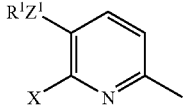

XXX

X, $R^1$ and $Z^1$ are as hereinbefore defined, a by adaptation of procedures described by K. R. Reistad et al., Acta. Chemica. Scandanavica B, 28, 667-72 (1974), incorporated herein by reference.

Compounds of formula XXX above, wherein X, $R^1$ and $Z^1$ are as hereinbefore defined, are prepared by the reaction of compounds of formula XXXI, wherein X and $Z^1$ is as hereinbefore defined, with compounds of

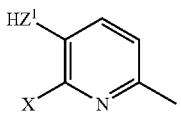

XXXI formula XXXII, wherein $R^1$ is as hereinbefore defined, by adaptation of $(R^1)_2SO_4$     XXXII procedures described by K. R. Reistad et al., Acta. Chemica. Scandanavica B, 28, 667-72 (1974), incorporated herein by reference.

Alternatively, compounds of formula XVIII above, wherein $Z^1$ represents oxygen, $Z^2$ represent oxygen or sulphur atoms, $Q^1$ and $Q^3$ represent CH, and $Q^2$ represents a nitrogen atom, and $R^1$ and $R^2$ are as hereinbefore defined are prepared from compounds of formula XXXIII, wherein $R^1$, $R^2$ and $Z^2$ are as

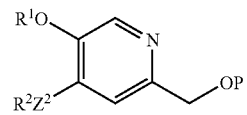

XXXIII hereinbefore defined, and P represents a protecting group, such as a silyl group, for example t-butyldimethylsilyl, or a trityl group, by reaction with an excess or a catalytic quantity of aqueous acid, for example formic acid, trifluoroacetic acid or acetic acid, neat or in the presence of a co-solvent, for example ethyl acetate, at a temperature from about room temperature to about 100° C.

Compounds of formula XXXIII above, $R^1$, $R^2$, $Z^2$ and P are as hereinbefore defined, are prepared by the reaction of compounds of formula XXXIV, wherein Y represents $P^1$ or $R^1$, $P^1$ represents a protecting group, such

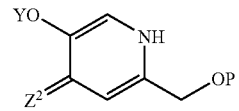

XXXIV as benzyl, and $R^1$, $Z^2$ and P are as hereinbefore defined, (1) where Y and $Z^2$ of XXXIV represent respectively $R^1$ and an oxygen atom, with compounds of formula XXI, wherein $R^2$ is as hereinbefore defined, in the presence of a dialkyl diazodicarboxylate, for example diisopropyldiazodicarboxylate, and a phosphine, preferably triarylphosphine, such as triphenylphosphine, in an inert solvent, for example toluene or an ether, such as tetrahydrofuran or diethyl ether, at a temperature from about −20° C. to reflux, or (2) where Y and $Z^2$ of XXXIV represent respectively $R^1$ and a sulphur atom, with compounds of formula VIII above, wherein $R^2$ and X are as hereinbefore defined, and X is preferably bromo, preferably in the presence of a base, for example an alkali metal hydride, such as sodium hydride, an alkali metal hydroxide or carbonate, such as sodium hydroxide or carbonate, or an amine, preferably a tertiary amine, such as triethylamine or pyridine, optionally in an inert solvent, for example dichloromethane, dimethylformamide, or an ether, such as diethyl ether or tetrahydrofuran, preferably at a temperature from about 0° C. to reflux, or (3) where Y of XXXIV represents $P^1$, a protecting group as hereinbefore defined, and $Z^2$ of XXXIV represents an oxygen or sulphur atom, then XXXIV is treated as in procedure (1) or (2) herein to prepare compounds of formula XXXV, wherein Y is $P^1$, and P, $P^1$, $Z^2$ and $R^2$ are as herein beforefore defined,

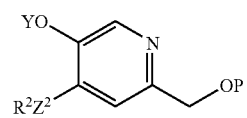

XXXV that are then selectively deprotected to remove $P^1$ as a benzyl group, for example by hydrogenolysis in the presence of a supported metal catalyst, such as 5% palladium on charcoal, in an inert solvent, for example ethyl acetate, or preferably ethanol to yield compounds of formula XXXVI, wherein P, $Z^2$ and $R^2$

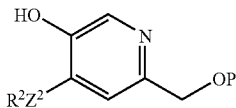

XXXVI are as hereinbefore defined, that are then alkylated with compounds of formula XXXVII, wherein $R^1$ and X are hereinbefore defined, in the presence of a base, $R^1X$  XXXVII for example an amine, such as 1,8-diazabicyclo[5.4.0]undec-7-ene, or preferably an alkali metal carbonate, such as potassium carbonate, in an inert solvent, for example dimethylformamide, at a temperature from about 0° C. to about 120° C.

Compounds of formula XXXIV above, wherein Y, $Z^2$ and P are as hereinbefore defined, are prepared by the reaction of compounds of formula XXXVIII, wherein Y is as hereinbefore defined, and $Z^2$ represents an oxygen

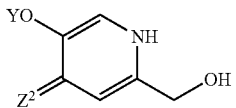

XXXVIII atom, with compounds of formula XXXIX, wherein P and X are as

PX  XXXIX hereinbefore defined, preferably in the presence of base, for example an amine, preferably a tertiary amine, for example triethylamine or preferably 4-dimethylaminopyridine, in an inert solvent, for example dimethylformamide or tetrahydrofuran, at from about room temperature to about 120° C., preferably from about 60° C. to about 100° C., and the protected product is optionally converted to the corresponding protected product wherein $Z^2$ is sulphur, with phosphorus pentasulfide or 2,4-bis(4-methoxyphenyl)-1,3-dithia-2,4-diphosphetane-2,4-disulfide, preferably in a solvent such as pyridine or toluene, and preferably at a temperature from about 0° C. to reflux.

Compounds of formula XXXVIII above, wherein $Z^2$ represents an oxygen atom, and Y is as hereinbefore defined, are prepared from compounds of formula XXXX, wherein Y is as hereinbefore defined, by adaptation of the

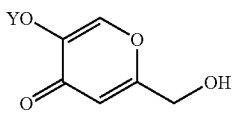

XXXX procedures described by H. C. Beyerman, Receueil, 77, 249-57, (1958) and European Patent 204207 (20 May 1986), incorporated herein by reference.

Compounds of formula XXXX wherein Y is as hereinbefore defined, are prepared by the reaction of compounds of formula XXXXI, with compounds

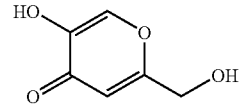

XXXXI of formula XXXII above, wherein $R^1$ is as hereinbefore defined, by adaptation of the alkylation procedure described by H. C. Beyerman, Receueil, 77, 249-57, (1958) and European Patent 204207 (20 May 1986), incorporated herein by reference.

Compounds of formula XII above, wherein $Z^1$ and $Z^2$ represent an oxygen atoms, $Q^1$ and $Q^3$ represent CH, $Q^2$ represents N, and $R^1$, $R^2$ and $R^7$ are as hereinbefore defined are prepared by the reaction of compounds of formula XXXXII, wherein $Z^2$ represents an oxygen atom, and $R^1$ and $R^7$ are as

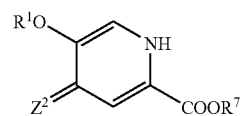

XXXXII hereinbefore defined, with compounds of formula XXI above, wherein $R^2$ is as hereinbefore defined, in the presence of a dialkyl diazodiarboxylate, for example diisopropyldiazodicarboxylate, and a phosphine, preferably triarylphosphine, such as triphenylphosphine, in an inert solvent, for example toluene or an ether, such as tetrahydrofuran or diethyl ether, at a temperature from about −20° C. to reflux.

Compounds of formula XXXXII above, wherein $Z^2$ represents an oxygen atom, and $R^1$ and $R^7$ are as hereinbefore defined, are prepared by the reaction of compounds of formula XXXXIII, wherein $R^1$ and $Z^2$ are as

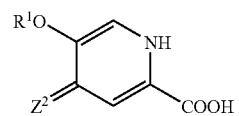

XXXXIII hereinbefore defined, with compounds of formula XXIX, wherein $R^7$ is as hereinbefore defined, in the presence of an acid, preferably a mineral acid, for example sulphuric acid, or preferably hydrogen chloride, at a temperature from about 0° C. to reflux, preferably at an elevated temperature.

Compounds of formula XXXXIII above, wherein $R^1$ and $Z^2$ are as hereinbefore defined, are prepared from compounds of formula XXXVIII above, wherein Y is $R^1$, $Z^2$ represents an oxygen atom, and $R^1$ is as hereinbefore defined, by adaptation of the procedure described by H. C. Beyerman, Receueil, 77, 249-57, (1958), incorporated herein by reference.

Alternatively, compounds of formula XVIII above, wherein $Q^1$ and $Q^2$ are N, $Q^3$ is CH, $R^1R^2$ are as hereinbefore defined, and $Z^1$ and $Z^2$ represent oxygen atoms, are prepared from compounds of formula XXXXIV, wherein $R^1$,

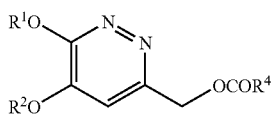

$R^2$, and $R^4$ are as hereinbefore defined, by reaction with aqueous alkali metal hydroxide or carbonate, such as potassium hydroxide or preferably potassium carbonate, in an inert co-solvent, such as methanol, at a temperature from about room temperature to reflux.

Compounds of formula XXXXIV above, wherein $R^1$, $R^2$, and $R^4$ are as hereinbefore defined, are prepared from compounds of formula XXXXV,

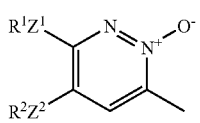

wherein $R^1$ and $R^2$ are as hereinbefore defined (prepared by adaptation of the method of M. Ogata and H. Kano, J. Heterocyclic Chem., 11, 29-35, (1963), incorporated herein by reference), by reaction with compounds of the formula XXXXVI, wherein $R^4$ is as hereinbefore defined, preferably a $$(R^4CO)_2O \quad\quad\quad XXXXVI$$

methyl group, using compound XXXXVI as solvent at about room temperature to reflux, preferably at elevated temperature.

The present invention is further exemplified but not limited by the following illustrative examples which illustrate the preparation of the compounds according to the invention. The Reference Examples illustrate the preparation of the intermediates.

In the nuclear magnetic resonance spectra (NMR) the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad.

Example 1

Compounds A-BH

A suspension of 3-cyclopentyloxy-6-fluoro-4-methoxybenzoic acid (0.88 g) in dry toluene (10 mL) is treated with thionyl chloride (2 mL) and the mixture is refluxed for 90 minutes. The mixture is cooled and concentrated in vacuo, to give "yellow oil A".

A suspension of sodium hydride (0.4 g of a 60% dispersion in mineral oil) in dimethylformamide (5 mL) is treated with a solution of 4-amino-3,5-dichloropyridine (0.82 g) in dimethylformamide (5 mL) and the reaction mixture is stirred at room temperature for 30 minutes. It is then treated with a solution of the "yellow oil A" in dimethylformamide (5 mL) and stirred at 45° C. for 16 hours. It is then cooled, poured into water (50 mL) and extracted with chloroform (3×500 mL). The combined extracts are dried over magnesium sulphate and concentrated. The residual yellow oil is subjected to flash chromatography [a 3:1 mixture of petroleum ether (b.p. 60-80° C.) and ethyl acetate is used as eluent in a silica gel column] to give N-(3,5-dichloropyrid-4-yl)-3-cyclopentyloxy-6-fluoro-4-methoxybenzamide (0.77 g), in the form of a white solid, m.p. 143-144° C. [Elemental analysis: C, 53.75; H, 4.28; N, 7.29%; calculated: C, 54.15; H, 4.29; N, 7.02%. NMR (CDCl$_3$): 8.56 (s, 1H), 8.37 (d, 1H, J=18 Hz), 7.62 (d, 1H, J=8 Hz), 6.71 (d, 1H, J=14 Hz), 4.87-4.82 (m, 1H), 3.93 (s, 3H), 2.03-1.57 (m, 8H)].

By proceeding in a similar manner, but replacing 4-amino-3,5-dichloropyridine by the appropriate quantities of the corresponding aniline or aminopyridine derivatives and acid chlorides there are prepared:

N-(2,6-difluorophenyl)-3-cyclopentyloxy-6-fluoro-4-methoxybenzamide;
N-(2-chloro-6-fluorophenyl)-3-cyclopentyloxy-6-fluoro-4-methoxybenzamide;
N-(2-trifluoromethylphenyl)-3-cyclopentyloxy-6-fluoro-4-methoxybenzamide;
N-(2,4,6-trichlorophenyl)-3-cyclopentyloxy-6-fluoro-4-methoxybenzamide;
N-(2,6-dibromophenyl)-3-cyclopentyloxy-6-fluoro-4-methoxybenzamide;
N-(2-chloro-6-methylphenyl)-3-cyclopentyloxy-6-fluoro-4-methoxybenzamide;
N-(2,6-dichlorophenyl)-3-cyclopentyloxy-6-fluoro-4-methoxybenzamide;
N-(2-fluorophenyl)-3-cyclopentyloxy-6-fluoro-4-methoxybenzamide;
N-phenyl-3-cyclopentyloxy-6-fluoro-4-methoxybenzamide;
N-(2-methoxyphenyl)-3-cyclopentyloxy-6-fluoro-4-methoxybenzamide;
N-(2-chlorophenyl)-3-cyclopentyloxy-6-fluoro-4-methoxybenzamide;
N-(3-chlorophenyl)-3-cyclopentyloxy-6-fluoro-4-methoxybenzamide;
N-(4-methoxyphenyl)-3-cyclopentyloxy-6-fluoro-4-methoxybenzamide;
N-(2,6-dimethylphenyl)-3-cyclopentyloxy-6-fluoro-4-methoxybenzamide;
N-(2-methylthiophenyl)-3-cyclopentyloxy-6-fluoro-4-methoxybenzamide;
N-(2-bromophenyl)-3-cyclopentyloxy-6-fluoro-4-methoxybenzamide;
N-(2-methoxycarbonylphenyl)-3-cyclopentyloxy-6-fluoro-4-methoxybenzamide;
N-(2-aminosulfonylphenyl)-3-cyclopentyloxy-6-fluoro-4-methoxybenzamide;
N-(2-benzoylphenyl)-3-cyclopentyloxy-6-fluoro-4-methoxybenzamide;
N-(2-cyanophenyl)-3-cyclopentyloxy-6-fluoro-4-methoxybenzamide;
N-(2,5-dichlorophenyl)-3-cyclopentyloxy-6-fluoro-4-methoxybenzamide;
N-(3-methylphenyl)-3-cyclopentyloxy-6-fluoro-4-methoxybenzamide;
N-(2-nitrophenyl)-3-cyclopentyloxy-6-fluoro-4-methoxybenzamide;
N-(2-dimethylaminophenyl)-3-cyclopentyloxy-6-fluoro-4-methoxybenzamide;
N-(2-acetylphenyl)-3-cyclopentyloxy-6-fluoro-4-methoxybenzamide;
N-(2-hydroxyphenyl)-3-cyclopentyloxy-6-fluoro-4-methoxybenzamide;
N-(4-chloropyrid-3-yl)-3-cyclopentyloxy-6-fluoro-4-methoxybenzamide;
N-pyrid-2-yl-3-cyclopentyloxy-6-fluoro-4-methoxybenzamide;

N-pyrazin-2-yl-3-cyclopentyloxy-6-fluoro-4-methoxybenzamide;
N-pyrimidin-2-yl-3-cyclopentyloxy-6-fluoro-4-methoxybenzamide;
N-(3-methylpyrid-2-yl)-3-cyclopentyloxy-6-fluoro-4-methoxybenzamide;
N-pyrid-3-yl-3-cyclopentyloxy-6-fluoro-4-methoxybenzamide;
N-(3-chloropyrid-2-yl)-3-cyclopentyloxy-6-fluoro-4-methoxybenzamide;
N-(3-chloropyrid-4-yl)-3-cyclopentyloxy-6-fluoro-4-methoxybenzamide;
N-pyrid-4-yl-3-cyclopentyloxy-6-fluoro-4-methoxybenzamide;
N-(3,5-dimethylisoxazol-4-yl)-3-cyclopentyloxy-6-fluoro-4-methoxybenzamide;
N-(3,5-dibromopyrid-4-yl)-3-cyclopentyloxy-6-fluoro-4-methoxybenzamide;
N-(3,5-dimethylpyrid-4-yl)-3-cyclopentyloxy-6-fluoro-4-methoxybenzamide;
N-(2,6-dichloro-4-cyanophenyl)-3-cyclopentyloxy-6-fluoro-4-methoxybenzamide;
N-(2,6-dichloro-4-methoxycarbonylphenyl)-3-cyclopentyloxy-6-fluoro-4-methoxybenzamide;
N-(2,3,5-trifluoropyrid-4-yl)-3-cyclopentyloxy-6-fluoro-4-methoxybenzamide;
N-(2,6-dichloro-4-ethoxycarbonylphenyl)-3-cyclopentyloxy-6-fluoro-4-methoxybenzamide;
N-(2,6-dichloro-4-nitrophenyl)-3-cyclopentyloxy-6-fluoro-4-methoxybenzamide;
N-(3,5-difluoropyrid-4-yl)-3-cyclopentyloxy-6-fluoro-4-methoxybenzamide;
N-(3-bromo-5-chloropyrid-4-yl)-3-cyclopentyloxy-6-fluoro-4-methoxybenzamide;
N-(2,4,6-trifluorophenyl)-3-cyclopentyloxy-6-fluoro-4-methoxybenzamide;
N-(2,6-dichloro-4-methoxyphenyl)-3-cyclopentyloxy-6-fluoro-4-methoxybenzamide;
N-(4,6-dichloropyrimid-5-yl)-3-cyclopentyloxy-6-fluoro-4-methoxybenzamide;
N-(2,3,5,6-tetrafluoropyrid-4-yl)-3-cyclopentyloxy-6-fluoro-4-methoxybenzamide;
N-(3,5-dichloro-2,6-difluoropyrid-4-yl)-3-cyclopentyloxy-6-fluoro-4-methoxybenzamide;
N-(5-cyano-3-methylisothiazol-4-yl)-3-cyclopentyloxy-6-fluoro-4-methoxybenzamide;
N-(2,6-dichloro-4-carbamoylphenyl)-3-cyclopentyloxy-6-fluoro-4-methoxybenzamide;
N-(3-chloro-2,5,6-trifluoropyrid-4-yl)-3-cyclopentyloxy-6-fluoro-4-methoxybenzamide;
N-(4-nitrophenyl)-3-cyclopentyloxy-6-fluoro-4-methoxybenzamide;
N-(3-methyl-5-bromoisothiazol-4-yl)-3-cyclopentyloxy-6-fluoro-4-methoxybenzamide;
N-(3,5-dimethylisothiazol-4-yl)-3-cyclopentyloxy-6-fluoro-4-methoxybenzamide;
N-(2,6-difluorophenyl)-3-cyclohexyloxy-6-fluoro-4-methoxybenzamide;
N-(2,6-difluorophenyl)-3-butoxy-6-fluoro-4-methoxybenzamide; and
N-(2,6-difluorophenyl)-3-propoxy-6-fluoro-4-methoxybenzamide.

Example 2

Compounds BI-BJ

A solution of 4-amino-3,5-dichloropyridine (3.73 g) in dry tetrahydrofuran (50 mL) under nitrogen at 5-10° C. is treated portionwise with sodium hydride (60% dispersion in oil; 1.87 g). After 30 minutes it is treated dropwise with a solution of 3-cyclopent-2-enyloxy-4-methoxybenzoyl chloride in dry tetrahydrofuran (50 mL; that is prepared, as described in Reference Example 6, from 5.89 g 3-cyclopent-2-enyloxy-4-methoxybenzoic acid). The resulting mixture is allowed to warm to room temperature and left to stand overnight. Most of the solvent is then removed under reduced pressure and the residue is partitioned between water (250 mL) and dichloromethane (250 mL) and the aqueous layer is further extracted with dichloromethane (2×250 mL). The combined organic layers are dried over sodium sulfate, the solvent is removed under reduced pressure, and the resulting residue is subjected to flash chromatography on silica gel, eluting with mixtures of ethyl acetate and pentane (3:7 to 1:1 v/v), to give a cream solid (1.25 g), which is recrystallized from a mixture of ethyl acetate and pentane, to give (±)-N-(3,5-dichloropyrid-4-yl)-3-cyclopent-2-enyloxy-4-methoxybenzamide (0.80 g), as a white solid, m.p. 177-178° C. [Elemental analysis: C, 56.9; H, 4.2; N, 7.4; Cl, 18.6%; calculated: C, 57.0; H, 4.3; N, 7.4; Cl, 18.7%].

By proceeding in a similar manner, but using 3-cyclopent-2-enyloxy-6-fluoro-4-methoxybenzoyl chloride (that is prepared, as described in Reference Example 6) there is prepared N-(3,5-dichloropyrid-4-yl)-3-cyclopent-2-enyloxy-6-fluoro-4-methoxybenzamide.

Example 3

Compounds BK-BL

A solution of 4-amino-3,5-dichloropyridine (0.93 g) in dry tetrahydrofuran (56 mL) under nitrogen at 5-10° C. is treated portionwise with sodium hydride (60% dispersion in oil, 0.57 g). After 1 hour it is treated dropwise with a solution of 3-cyclopent-3-enyloxy-4-methoxybenzoyl chloride in dry tetrahydrofuran (30 mL) that is prepared as described in Reference Example 7 from 1.33 g 3-cyclopent-3-enyloxy-4-methoxybenzoic acid. The resulting mixture is allowed to warm to room temperature, stirred for a further 3 hours and then poured into 5% aqueous potassium carbonate (430 mL). The resulting emulsion is extracted with ethyl acetate (3×150 mL), the combined organic extracts washed with water (2×20 mL), followed by ice-cold 1 M aqueous hydrochloric acid (2×20 mL) and dried over sodium sulfate. The solvent is removed under reduced pressure and the resulting residue subject to flash chromatography on silica gel, eluting with mixtures of t-butyl methyl ether and cyclohexane (2:3 to 7:3 v/v), to give a cream solid, which is recrystallized from acetonitrile to give N-(3,5-dichloropyrid-4-yl)-3-cyclopent-3-enyloxy-4-methoxybenzamide (0.54 g), as a white solid, m.p. 193-195° C. [Elemental analysis: C, 56.7; H, 4.2; N, 7.3%; calculated: C, 57.0; H, 4.3; N, 7.4%].

By proceeding in a similar manner, but using 3-cyclopent-3-enyloxy-6-fluoro-4-methoxybenzoyl chloride (that is prepared, as described in Reference Example 7) there is prepared N-(3,5-dichloropyrid-4-yl)-3-cyclopent-3-enyloxy-6-fluoro-4-methoxybenzamide.

Example 4

Compounds BM-BN

A stirred solution of N-(2-methylthiophenyl)-3-cyclopentyloxy-4-methoxybenzamide (1.80 g; that is prepared as described hereinbefore in Example 5) is treated with a solution of 3-chloroperbenzoic acid (3.60 g; 85% pure) in dichloromethane (72 mL), dropwise, and then it is stirred at room temperature for 5 hours. The reaction mixture is washed with saturated aqueous sodium bicarbonate solution and then with water, and then it is dried over magnesium sulfate. The mixture is concentrated to give N-(2-methylsulfonylphenyl)-3-cyclopentyloxy-4-methoxybenzamide, (1.12 g), in the form of a white solid, m.p. 119-121° C. [NMR(CDCl$_3$): 1.52-2.16 (m, 8H), 3.1 (s, 3H), 3.94 (s, 3H), 4.9 (m, 1H), 6.96 (d, 1H), 7.46 (m, 1H), 7.6 (m, 2H), 7.7 (t, 1H), 7.95 (d, 1H), 8.68 (d, 1H); Elemental analysis: C, 61.6; H, 6.0; N, 3.5; S, 8.5%; Calculated: C, 61.7; H, 5.95; N, 3.6; S, 8.5%].

By proceeding in a similar manner, but replacing N-(2-methylthiophenyl)-3-cyclopentyloxy-4-methoxybenzamide by N-(2-methylthiophenyl)-3-cyclopentyloxy-6-fluoro-4-methoxybenzamide, that is prepared as described above in Example 1), there is prepared N-(2-methylsulfonylphenyl)-3-cyclopentyloxy-6-fluoro-4-methoxybenzamide.

Example 5

Compounds BO-BP

3-Cyclopentyloxy-4-methoxybenzoyl chloride (13.3 g) and 2-chloroaniline (6.6 g) are dissolved in pyridine (50 mL) and the solution is allowed to stand at room temperature for 1 hour. Phosphorus pentasulfide (13 g) is added and the stirred mixture is heated at 110° C. for 1.5 hours. After cooling to room temperature the mixture is poured into an ice-cold solution of concentrated hydrochloric acid (100 mL) in water (400 mL). The mixture is stirred for 1 hour and the yellow solid is collected, washed with water and subjected to flash chromatography on silica gel, eluting with a mixture of cyclohexane and ethyl acetate (3:1 v/v), to give N-(2-chlorophenyl)-3-cyclopentyloxy-4-methoxy(thiobenzamide) (5.4 g), m.p. 129-131° C. [Elemental analysis: C, 62.6; H, 5.5; N, 3.9; S, 8.9%; Calculated: C, 63.1; H, 5.6; N, 3.9; S, 8.9%].

By proceeding in a manner similar, but using 3-cyclopentyloxy-6-fluoro-4-methoxybenzoyl chloride, instead of 3-cyclopentyloxy-4-methoxybenzoyl chloride, there is prepared N-(2-chlorophenyl)-3-cyclopentyloxy-6-fluoro-4-methoxy (thiobenzamide).

Example 6

Compounds BO-BR

A stirred solution of N-(3,5-dichloropyrid-4-yl)-3-cyclopentyloxy-4-methoxybenzamide (2.0 g) in toluene (50 mL) is treated with 2,4-bis(4-methoxyphenyl)-1,3-dithia-2,4-diphosphetane-2,4-disulfide (3.0 g), and the mixture is heated at 100° C. for 2 hours. After cooling to room temperature and filtration, the filtrate is concentrated in vacuo, to give a yellow oil. This oil is subjected to flash chromatography on silica gel, using a mixture of pentane and ethyl acetate (8:2 v/v) as eluent, to give N-(3,5-dichloropyrid-4-yl)3-cyclopentyloxy-4-methoxy(thiobenzamide) (0.64 g) m.p. 118-119° C. [Elemental analysis: C, 54.1; H, 4.6; Cl, 17.4; N, 6.8%; calculated: C, 54.4; H, 4.6; Cl, 17.85; N, 7.05%].

By proceeding in a manner similar, but replacing the N-(3, 5-dichloropyrid-4-yl)-3-cyclopentyloxy-4-methoxybenzamide by the appropriate quantity of N-(3,5-dichloropyrid-4-yl)-3-cyclopentyloxy-6-fluoro-4-methoxybenzamide, which is prepared as described hereinafter in Example 1, there is prepared N-(3,5-dichloropyrid-4yl)-3-cyclopentyloxy-6-fluoro-4-methoxy(thiobenzamide).

Example 75

Compounds BS-BT

A solution of N-(2,6-dichloro-4-nitrophenyl)-3-cyclopentyloxy-4-methoxybenzamide (1.5 g) in glacial acetic acid (22 mL) is treated with iron pin dust (1.3 g) and the mixture is heated with stirring at 90° C. for 1 hour. The reaction mixture is cooled, basified to pH 8 by treatment with saturated aqueous sodium carbonate solution, and extracted with ethyl acetate (2×150 mL). The combined organic extract is dried over magnesium sulfate and concentrated in vacuo, to give a white solid. This solid is subjected to flash chromatography, eluting with a mixture of ethyl acetate and pentane (1:1 v/v), to give N-(2,6-dichloro-4-aminophenyl)-3-cyclopentyloxy-4-methoxybenzamide (0.8 g), m.p. 170-172° C. [Elemental analysis: C, 54.8; H, 5.04; N, 6.5; Cl, 17.4%; calculated: C, 57.7; H, 5.1; N, 7.1; Cl, 17.9%].

By proceeding in a manner similar, but replacing the N-(2, 6-dichloro-4-nitrophenyl)-3-cyclopentyloxy-4-methoxybenzamide by the appropriate quantity of N-(2,6-dichloro-4-nitrophenyl)-3-cyclopentyloxy-6-fluoro-4-methoxybenzamide, which is prepared as described hereinafter in Example 1, there is prepared N-(2,6-dichloro-4-aminophenyl)-3-cyclopentyloxy-6-fluoro-4-methoxybenzamide.

Example 8

Compounds BU-BV

Acetic anhydride (10 mL) is treated with N-(2,6-dichloro-4-aminophenyl)-3-cyclopentyloxy-4-methoxybenzamide (0.8 g), and the reaction mixture is stirred for 2 hours and left to stand overnight. It is then poured into water (100 mL), and extracted with ethyl acetate (100 mL) and then with dichloromethane (100 mL). The organic extracts are combined, dried over magnesium sulfate, and evaporated, to give N-(4-acetylamino-2,6-dichlorophenyl)-3-cyclopentyloxy-4-methoxybenzamide (0.4 g), m.p. 250-252° C. [Elemental analysis: C, 57.6; H, 5.05; N, 6.3; Cl, 16.1%; calculated: C, 57.5; H, 5.1; N, 6.4; Cl, 16.2%].

By proceeding in a manner similar, but replacing the N-(2, 6-dichloro-4-aminophenyl)-3-cyclopentyloxy-4-methoxybenzamide by the appropriate quantity of N-(2,6-dichloro-4-aminophenyl)-3-cyclopentyloxy-6-fluoro-4-methoxybenzamide, which is prepared as described hereinafter in Example 1, there is prepared N-(2,6-dichloro-4-acetylaminophenyl)-3-cyclopentyloxy-6-fluoro-4-methoxybenzamide.

Example 9

Compounds BW-BX

A stirred solution of N-(2,6-dichloro-4-ethoxycarbonylphenyl)-3-cyclopentyloxy-4-methoxybenzamide (6.1 g) in dry tetrahydrofuran (80 mL) at room temperature under argon is treated dropwise with a solution of lithium borohydride in tetrahydrofuran (115 mL; 2 M). The mixture is stirred overnight and then it is treated portionwise with saturated brine (200 mL) and stirred for 30 minutes. The organic layer is then washed with water, dried over magnesium sulfate and evaporated. The resulting residue is subjected to flash chromatography on silica gel, to give N-(2,6-dichloro-4-hydroxymethylphenyl)-3-cyclopentyloxy-4-methoxybenzamide (4.4 g), m.p. 174-176° C. [Elemental analysis: C, 57.1; H, 5.4; N, 2.9%; calculated $C_{20}H_{21}O_4NCl_2 \cdot 0.5H_2O$: C, 57.3; H, 5.3; N, 3.3%]

By proceeding in a similar manner, but using the appropriate quantity of N-(2,6-dichloro-4-ethoxycarbonylphenyl)-3-cyclopentyloxy-6-fluoro-4-methoxybenzamide (that is prepared as described in Example 1) instead of N-(2,6-dichloro-4-ethoxycarbonylphenyl)-3-cyclopentyloxy-4-methoxybenzamide, there is prepared N-(2,6-dichloro-4-hydroxymethylphenyl)-3-cyclopentyloxy-6-fluoro-4-methoxybenzamide.

Example 10

Compounds BY-BZ

A solution of N-(2,6-dichloro-4-hydroxymethylphenyl)-3-cyclopentyloxy-4-methoxybenzamide (4.4 g; that is prepared as described in Example 9) in dichloromethane (30 mL) is treated with activated manganese dioxide (6.2 g), and the mixture is stirred at reflux for 24 hours. The mixture is filtered, the filtrate is evaporated, and the resulting residue is subjected to flash chromatography on silica gel, eluting with ethyl acetate, to give N-(2,6-dichloro-4-formylphenyl)-3-cyclopentyloxy-4-methoxy-benzamide (2.4 g), m.p. 96-98° C. [Elemental analysis: C, 59.0; H, 5.1; N, 3.1%; calculated: C, 58.8; H, 4.7; N, 3.4%].

By proceeding in a similar manner, but using the appropriate quantity of N-(2,6-dichloro-4-hydroxymethylphenyl)-3-cyclopentyloxy-6-fluoro-4-methoxybenzamide (that is prepared as described in Example 9) instead of N-(2,6-dichloro-4-hydroxymethylphenyl)-3-cyclopentyloxy-4-methoxybenzamide, there is prepared N-(2,6-dichloro-4-formylphenyl)-3-cyclopentyloxy-6-fluoro-4-methoxybenzamide.

Example 11

Compounds CA-CB

A solution of N-(3,5-dichloropyrid-4-yl)-3-cyclopentyloxy-4-methoxybenzamide (3.8 g) in dry tetrahydrofuran (25 mL) is treated with a suspension of sodium hydride (60% dispersion in oil; 0.40 g), and the mixture is stirred until effervescence has ceased and a solution has formed. This solution is evaporated in vacuo and the resulting residue is triturated with t-butyl methyl ether (20 mL). The resulting off-white solid is filtered off, quickly washed with t-butyl methyl ether (2×20 mL) and dried, to give the sodium salt of N-(3,5-dichloropyrid-4-yl)-3-cyclopentyloxy-4-methoxybenzamide (3.5 g), m.p. 265-270° C. (with decomposition) [NMR (DMSO-$D_6$): 1.52-1.93 (m, 8H), 4.77 (s, 3H), 4.75-4.80 (m, 1H), 6.98 (d, 1H), 7.58 (dd, 1H), 7.60 (s, 1H), 8.20 (s, 2H); IR spectrum: strong peak at 1508 $cm^{-1}$, with no peaks at or near 1661 $cm^{-1}$ or 3244 $cm^{-1}$, which would have been characteristics of the starting material].

By proceeding in a similar manner, but using the appropriate quantity of N-(3,5-dichloropyrid-4-yl)-3-cyclopentyloxy-6-fluoro-4-methoxybenzamide (that is described as in Example 1) instead of N-(3,5-dichloropyrid-4-yl)-3-cyclopentyloxy-4-methoxybenzamide, there is prepared sodium salt of N-(3,5-dichloropyrid-4-yl)-3-cyclopentyloxy-6-fluoro-4-methoxybenzamide.

Example 12

Compounds CC-CG

By proceeding in a similar manner as in Example 1, but using the appropriate quantities of the appropriate benzoic acid instead of 3-cyclopentyloxy-6-fluoro-4-methoxybenzoic acid are prepared:

(±) N-(3,5-dichloropyrid-4-yl)-3-exonorbornyloxy-6-fluoro-4-methoxybenzamide, m.p. 139-140° C. [Elemental analysis: C, 56.6; H, 4.5; N, 6.6; Cl, 16.6%; calculated: C, 56.5; H, 4.5; N, 6.6; Cl, 16.7%].

N-(3,5-dichloropyrid-4-yl)-2-fluoro-5-isopropyloxy-4-methoxybenzamide, m.p. 154.5-156° C. [Elemental analysis: C, 51.8; H, 4.2; N, 7.4; Cl, 18.7%; calculated: C, 51.5; H, 4.05; N, 7.5; Cl, 19.0%].

(±)N-(3,5-dichloropyrid-4-yl)-2-fluoro-4-methoxy-5-(tricyclo[2.2.1.0]hept-2-yloxy)benzamide hemihydrate, m.p. 149-151° C. [Elemental analysis: C, 55.7; H, 4.0; N, 6.2%; calculated: C, 55.6; H, 4.2; N, 6.5%].

N-(3,5-dichloropyrid-4-yl)-3-cyclopentyloxy-4-difluoromethoxy-6-fluorobenzamide, m.p. 96-99° C. [Elemental analysis: C, 50.1; H, 3.8; N, 6.6; Cl, 16.6%; calculated: C, 49.7; H, 3.5; N, 6.4; Cl, 16.3%].

N-(3,5-dichloropyrid-4-yl)-4-difluoromethoxy-2-fluoro-5-isopropyloxybenzamide, m.p. 105-108° C. [Elemental analysis: C, 47.0; H, 3.2; N, 6.8; Cl, 17.4%; calculated: C, 47.0; H, 3.2; N, 6.85; Cl, 17.3%].

Example 13

Compound CH

A solution of oxalyl chloride (0.05 mL) in dichloromethane (3 mL) is cooled to −60° C. and dimethylsulfoxide (1 mL) added. After stirring at this temperature for 0.25 hours, a solution of 2-(3,5-dichloropyrid-4-yl)-1-(3-cyclopentyloxy-6-fluoro-4-methoxyphenyl)ethanol (0.2 g) in dichloromethane (5 mL) is added dropwise. After stirring at −60° C. for 0.25 hours, triethylamine (0.33 mL) is added dropwise and the solution stirred for 0.25 hour at −60° C. and then at room temperature overnight. The solution is then poured into water (30 mL), extracted with ethyl acetate (3×50 mL) and the combined organic extracts washed with brine (30 mL), dried (magnesium sulfate), and concentrated to give a yellow-brown oil. The oil is subjected to mplc on silica gel, using petroleum ether:ethyl acetate (3:1 v/v) as eluent to give 2-(3,5-dichloropyrid-4-yl)-1-(3-cyclopentyloxy-6-fluoro-4-methoxyphenyl)ethanone (0.14 g). m.p. 115-116.5° C. [Elemental analysis: C, 57.7; H, 4.7; N, 3.5%; calculated: C, 57.3; H, 4.6; N, 3.5%].

Example 14

Compounds CI-CN

A stirred solution of N-(3,5-dichloropyrid-4-yl)-2-fluoro-5-isopropyloxy-4-methoxybenzamide (0.5 g) in glacial acetic acid (10 mL) is treated dropwise with an aqueous solution of hydrogen peroxide (2 ml; 27.5%). The mixture is stirred for 3 hours at 70-80° C., treated with a further portion of aqueous hydrogen peroxide (2 mL), and the solution stirred for a further 12 hours. The solution is then cooled, basified by treatment with 2 N sodium hydroxide solution (50 mL) and extracted with ethyl acetate (3×150 mL). The combined organic extracts are washed with brine (50 mL), dried (magnesium sulfate) and concentrated to give a brown oil. The oil is subjected to mplc on silica gel using ether as eluent to give N-(3,5-dichloro-1-oxido-4-pyridinio)-2-fluoro-5-isopropyloxy-4-methoxybenzamide (0.25 g). m.p. 142-144° C. [Elemental analysis: C, 48.6; H, 3.9; N, 7.0; Cl, 17.6%. calculated: C, 48.3; H, 4.05; N, 7.0; Cl, 17.8%].

By proceeding in a similar manner, but using the appropriate quantities of the appropriate benzamide or ethanone there are prepared:

(±)N-(3,5-dichloro-1-oxido-4-pyridinio)-3-exonorbornyloxy-6-fluoro-4-methoxybenzamide, m.p. 101-106° C. [Elemental analysis: C, 53.9; H, 4.5; N, 6.3; Cl, 15.5%. calculated: C, 53.9; H, 4.4; N, 6.3; Cl, 15.9%].

N-(3,5-dichloro-1-oxido-4-pyridinio)-3-cyclopentyloxy-6-fluoro-4-methoxybenzamide, m.p. 143-144° C. [Elemental analysis: C, 52.9; H, 4.5; N, 6.4; Cl, 16.2%. calculated: C, 52.1; H, 4.1; N, 6.75; Cl, 17.1%].

N-(3,5-dichloro-1-oxido-4-pyridinio)-3-cyclopentyloxy-4-difluoromethoxy-6-fluorobenzamide, m.p. 129-130° C. [Elemental analysis: C, 47.6; H, 3.4; N, 6.0; Cl, 15.3%. calculated: C, 47.9; H, 3.35; N, 6.2; Cl, 15.7%].

N-(3,5-dichloro-1-oxido-4-pyridinio)-4-difluoromethoxy-2-fluoro-5-isopropyloxybenzamide, m.p. 196-198° C. [Elemental analysis: C, 45.2; H, 3.0; N, 6.5; Cl, 16.6%. calculated: C, 45.2; H, 3.1; N, 6.6; Cl, 16.7%].

2-(3,5-Dichloro-1-oxido-4-pyridinio)-1-(3-cyclopentyloxy-6-fluoro-4-methoxyphenyl)ethanone, m.p. 159-162° C. [Elemental analysis: C, 54.9; H, 4.4; N, 3.5; Cl, 16.9%. calculated: C, 55.1; H, 4.4; N, 3.4; Cl, 17.1%].

Example 15

Compound CO

Thionyl chloride (0.78 mL) is added to a solution of 5-cyclopentyloxy-6-methoxynicotinic acid (850 mg) and dimethylformamide (1 drop) in toluene (60 mL). The mixture is heated and stirred at reflux for 1 hour. The mixture is cooled and concentrated to give crude acid chloride.

Meanwhile, sodium hydride (320 mg of a 60% dispersion in oil) is added to a stirred solution of 4-amino-3,5-dichloropyridine (649 mg) in dry dimethylformamide (20 mL) under a nitrogen atmosphere. The mixture is stirred at room temperature for 30 minutes. The crude acid chloride is dissolved in dry dimethylformamide (10 mL) and the solution is added dropwise to the mixture. After 3 hours, the mixture is diluted with water and the mixture extracted with ethyl acetate. The ethyl acetate extracts are washed with water and dried (MgSO$_4$). Concentration of the extracts gave a buff solid which is triturated with methyl t.butyl ether to give 5-cyclopentyloxy-N-(3,5-dichloropyrid-4-yl)-6-methoxynicotinamide (500 mg) as a white solid, m.p. 182-183° C. [Elemental analysis: C, 53.4; H, 4.45; Cl, 18.6; N, 10.9% calculated: C, 53.4; H, 4.48; Cl, 18.55; N, 10.99%.]

Example 16

Compound CP

Thionyl chloride (0.46 mL) is added to a solution of 5-cyclopentyloxy-6-methoxynicotinic acid (500 mg) and dimethylformamide (1 drop) in toluene (10 mL). The mixture is heated and stirred at reflux for 1 hour. The mixture is cooled and concentrated to give crude acid chloride as a yellow oil which slowly crystallized.

Meanwhile, sodium hydride (128 mg of a 60% dispersion in oil) is added to a stirred solution of 2,6-dichloroaniline (263 mg) in dry tetrahydrofuran (10 mL) under a nitrogen atmosphere. The mixture is stirred at room temperature for 45 minutes. The crude acid chloride is dissolved in dry tetrahydrofuran (5 mL) and the resulting solution added dropwise to the mixture. After 3 hours the mixture is concentrated, treated with water, and extracted with ethyl acetate. The extracts are dried (MgSO$_4$) and concentrated to give a brown oil. Trituration of the oil with methyl t.butyl ether gave N-(2,6-dichlorophenyl)-5-cyclopentyloxy-6-methoxynicotinamide (250 mg) as a white solid, m.p. 145-6° C. [Elemental analysis: C, 56.7; H, 4.79; Cl, 18.5; N, 7.4% calculated: C, 56.7; H, 4.76; Cl, 18.6; N, 7.35%.]

Example 17

Compound CQ

Thionyl chloride (0.46 mL) is added to a solution of 5-cyclopentyloxy-6-methoxynicotinic acid (500 mg) and dimethylformamide (1 drop) in toluene (10 mL). The mixture is heated and stirred at reflux for 1 hour. The mixture is cooled, concentrated, and the residue dissolved in dichloromethane (5 mL). This solution is added dropwise to a solution of 4-amino-3,5-dimethylisoxazole (168 mg) and triethylamine (0.21 mL) in dichloromethane (20 mL). The resulting mixture is stirred at room temperature for 2 hours then at reflux for 1 hour. The cooled mixture is washed with water, 2 M aqueous hydrochloric acid, water, then dried (MgSO$_4$). After concentration the yellow oily residue is triturated with a mixture of n-pentane and methyl t.butyl ether to give 5-cyclopentyloxy-N-(3,5-dimethylisoxazol-4-yl)-6-methoxynicotinamide (240 mg) as a buff solid, m.p. 139-40° C. [Elemental analysis: C, 61.3; H, 6.40; N, 12.4% calculated: C, 61.6; H, 6.39; N, 12.68%.]

Example 18

Compound CR

Thionyl chloride (0.46 mL) is added to a solution of 5-cyclopentyloxy-6-methoxynicotinic acid (500 mg) and dimethylformamide (1 drop) in toluene (10 mL). The mixture is heated and stirred at reflux for 1 hour. The mixture is cooled and concentrated to give crude acid chloride.

Meanwhile, sodium hydride (128 mg of a 60% dispersion in oil) is added to a stirred solution of 4-amino-3,5-difluoropyridine (208 mg) in dry tetrahydrofuran (10 mL) under a nitrogen atmosphere. The mixture is stirred at room temperature for 60 minutes. The crude acid chloride is dissolved in dry tetrahydrofuran (5 mL) and the resulting solution added dropwise to the mixture. After 3 hours the mixture is treated with water and concentrated. The residue is diluted with water and the mixture extracted with ethyl acetate. The extracts are dried (MgSO$_4$) and concentrated to give a white solid. The solid is triturated with n-pentane and methyl t-butyl ether to give 5-cyclopentyloxy-N-(3,5-difluoropyrid-4-yl)-6-methoxynicotinamide (230 mg), as a white solid, m.p. 210-11° C. [Elemental analysis: C, 58.4; H, 4.93; N, 11.8% calculated: C, 58.45; H, 4.91; N, 12.03%.]

Example 19

Compound CS

Thionyl chloride (0.45 mL) is added to a solution of 6-cyclopentyloxy-5-methoxypyridine-2-carboxylic acid (510 mg) and dimethylformamide (1 drop) in toluene (6 mL). The mixture is heated and stirred at reflux for 2.5 hours. The mixture is cooled and concentrated to give crude acid chloride.

Meanwhile, sodium hydride (51 mg of a 60% dispersion in oil) is added to a stirred solution of 4-amino-3,5-dichloropyridine (350 mg) in dry tetrahydrofuran (10 mL) under a nitrogen atmosphere. The mixture is stirred at room temperature for 30 minutes. The crude acid chloride is dissolved in dry tetrahydrofuran (6 mL) and the resulting solution added dropwise to the mixture. The mixture is stirred for 4.5 hours and then allowed to stand at room temperature for 72 hours. The mixture is treated with water, concentrated and the residue extracted with ethyl acetate. After washing with water the extracts are dried ($MgSO_4$) and concentrated. The residue is purified by flash chromatography (alumina, pentane/ethyl acetate 9:1 v/v as eluent) to give 6-cyclopentyloxy-N-(3,5-dichloropyrid-4-yl)-5-methoxypyridine-2-carboxamide (750 mg) as a white solid, m.p. 164-6° C. [Elemental analysis: C, 53.6; H, 4.56; Cl, 18.4; N, 11.2% calculated: C, 53.4; H, 4.48; Cl, 18.55; N, 10.99%.]

Example 20

Compound CT n-Butyl lithium (4.9 mL of a 2.5M solution in hexanes) is added dropwise to a stirred solution of diisopropylamine (1.7 mL) in dry tetrahydrofuran (20 mL) at −78° C. under a nitrogen atmosphere. After 30 minutes. a solution of 3,5-dichloro-4-methylpyridine (1.95 g) in dry tetrahydrofuran (10 mL) is added dropwise and the solution stirred at −78° C. for a further 30 minutes. A solution of methyl 5-cyclopentyloxy-6-methoxynicotinoate (1.5 g) in dry tetrahydrofuran (15 mL) is added and the red mixture stirred and allowed to warm to room temperature during 4 hours. After stirring overnight at room temperature the mixture is treated with saturated aqueous ammonium chloride. The tetrahydrofuran layer is separated and the aqueous phase is extracted with ethyl acetate. The combined organic layers are washed with saline and dried over anhydrous magnesium sulphate. Concentration gives a light brown oil which is triturated with a mixture of n-pentane and methyl t-butyl ether to give 1-(5-cyclopentyloxy-6-methoxypyridin-3-yl)-2-(3,5-dichloropyrid-4-yl)ethanone (1 g) in the form of a beige solid, m.p. 118-9° C. [Elemental analysis: C, 56.8; H, 4.82; Cl, 18.5; N, 7.40% calculated: C, 56.7; H, 4.76; Cl, 18.6; N, 7.35%.]

Example 21

Compound CU

Thionyl chloride (0.55 mL) is added to a solution of 5-cyclopentyloxy-6-methylthionicotinic acid (0.6 g) in dry toluene (10 mL) containing dimethylformamide (1 drop) and the mixture stirred at reflux for 1.5 hours. The solution is evaporated in vacuo, redissolved in toluene and evaporated again to give the crude acid chloride.
Meanwhile sodium hydride (220 mg of a 60% dispersion in mineral oil) is added to a stirred solution of 4-amino-3,5-dichloropyridine (445 mg) in dry tetrahydrofuran (10 mL) under an atmosphere of nitrogen, and the mixture is stirred at room temperature for 1 hour. The crude acid chloride is dissolved in tetrahydrofuran (10 mL) and added to the mixture and the mixture stirred at room temperature for 3 hours. The mixture is evaporated, the residue diluted with water and the product extracted into ethyl acetate. The extracts are dried ($MgSO_4$), evaporated, and triturated with a mixture of n-pentane and t-butyl methyl ether to give 5-cyclopentyloxy-N-(3,5-dichloro-4-pyridyl)-6-methylthionicotinamide (500 mg) as a cream solid, m.p. 144-5° C. [Elemental analysis: C, 51.50; H, 4.42; Cl, 17.7; N, 10.5; S, 8.1% calculated: C, 51.26; H, 4.30; Cl, 17.8; N, 10.55; S, 8.05%].

Example 22

Compound CV

By proceeding in a similar manner to example 21 but replacing the 5-cyclopentyloxy-6-methylthionicotinic acid by the appropriate quantity of 5-isopropyloxy-6-methylthionicotinic acid there is obtained:
N-(3,5-dichloro-4-pyridyl)-5-isopropyloxy-6-methylthionicotinamide as a white solid, m.p. 167-8° C. [Elemental analysis: C, 48.20; H, 4.02; Cl, 19.30; N, 11.30% calculated: C, 48.40; H, 4.06; Cl, 19.05; N, 11.29%].

Example 23

Compound CW n-Butyl lithium (3.73 mL of a 2.5 M solution in hexanes) is added dropwise to a stirred solution of diisopropylamine (1.29 mL) in dry tetrahydrofuran (15 mL) at −75° C. under a nitrogen atmosphere. After stirring for 30 minutes, a solution of 3,5-dichloro-4-methylpyridine (1.48 g) in dry tetrahydrofuran (8 mL) is added dropwise and the mixture stirred for a further 30 minutes. A solution of methyl 5-isopropyloxy-6-methylthionicotinoate (1.1 g) in dry tetrahydrofuran (10 mL) is added dropwise at −75° C. and the mixture allowed to warm to room temperature during 4 hours. The reaction is quenched by the addition of saturated aqueous ammonium chloride and then the solvent is removed in vacuo. The aqueous residue is extracted with ethyl acetate, the extracts washed with water and dried ($MgSO_4$). After treating with decolourizing charcoal and removing the solvent, a dark yellow oil is obtained. The oil is dissolved in a minimum amount of n-pentane/methyl t-butylether and allowed to crystallize. 2-(3,5-dichloro-4-pyridyl)-1-(5-isopropyloxy-6-methylthio-3-pyridyl)ethanone (450 mg) is obtained as a white solid, m.p. 124-5° C. [Elemental analysis: C, 51.8; H, 4.34; Cl, 19.10; N, 7.50% calculated: C, 51.76; H, 4.34; Cl, 19.10; N, 7.55%].

Example 24

Compound CX

Hydrogen peroxide (3 mL of strength 27.5%) is added to a stirred suspension of 1-(5-cyclopentyloxy-6-methoxypyrid-3-yl)-2-(3,5-dichloropyrid-4-yl)ethanone (470 mg) in glacial acetic acid (5 mL) and the mixture heated at 75±5° C. for 3 hours. More hydrogen peroxide (1 mL of strength 27.5%) is added and the mixture heated for a further 2 hours. After cooling, the mixture is basified with 6 M aqueous sodium hydroxide and extracted with ethyl acetate. The extracts are washed with water, dried ($MgSO_4$) and evaporated. The residue is triturated with diethyl ether to afford 1-(5-cyclopentyloxy-6-methoxypyrid-3-yl)-2-(3,5-dichloro-1-oxido-4-pyridinio)ethanone hemihydrate (100 mg) as a white solid, m.p. 171-2° C. [Elemental analysis: C, 53.5; H, 4.51; N, 7.0% calculated: C, 53.20; H, 4.71; N, 6.90%].

Example 25

Compounds CY-CZ

Diisopropyl azodicarboxylate (1.67 mL) is added to a stirred solution of triphenylphosphine (2.22 g) in dry tetrahydrofuran (20 mL) at 0-5° C. under a nitrogen atmosphere. After 30 minutes, methyl 5-hydroxy-6-methoxynicotinoate (1.55 g) and a solution of a mixture of (±)-endo- and (±)-exo-(8,9,10-trinorborn-5-en-2-ol) (0.94 g) in dry tetrahydrofuran (5 mL) are added successively and the mixture refluxed for 24 hours. After cooling to room temperature the mixture is diluted with water and extracted with ethyl acetate. The extracts are washed with water, dried ($MgSO_4$) and evaporated.

Purification by Flash Chromatography (n-pentane/ethyl acetate 9:1 v/v on silica) affords a mixture of methyl (±)-6-methoxy-5-exo-(8,9,10-trinorborn-5-en-2-yloxy)nicotinoate and methyl (±)-6-methoxy-5-(tricyclo[2.2.1.0.$^{2.6.}$]hept-2-yloxy)nicotinoate, (950 mg) [Elemental analysis: C, 65.50; H, 6.35; N, 5.14% calculated: C, 65.44; H, 6.22; N, 5.09%].

The mixture of methyl (±)-6-methoxy-5-exo-(8,9,10-trinorborn-5-en-2-yloxy)nicotinoate and methyl (±)-6-methoxy-5-(tricyclo[2.2.1.0.$^{2.6.}$]hept-2-yloxy)nicotinoate, (900 mg), dissolved in methanol (20 mL) is treated with a solution of potassium hydroxide (380 mg) in water (5 mL) and stirred at 45° C. for 3 hours. After cooling the bulk of the solvent is removed in vacuo, the residue dissolved in water and the solution acidified to pH 2 with concentrated aqueous hydrochloric acid. The products are extracted into ethyl acetate, the extracts dried (MgSO$_4$) and evaporated to give a mixture of (±)-6-methoxy-5-exo-(8,9,10-trinorborn-5-en-2-yloxy)nicotinic acid and (±)-6-methoxy-5-(tricyclo[2.2.1.0.$^{2.6.}$]-hept-2-yloxy)nicotinic acid, (670 mg), as a white solid. [Elemental analysis: C, 64.50; H, 5.76; N, 5.53% calculated: C, 64.36; H, 5.79; N, 5.36%].

The mixture of (±)-6-methoxy-5-exo-(8,9,10-trinorborn-5-en-2-yloxy)nicotinic acid and (±)-6-methoxy-5-(tricyclo[2.2.1.0.$^{2.6.}$]hept-2-yloxy)nicotinic acid, (670 mg), is stirred in a mixture of dichloromethane (10 mL) and dimethylformamide (1 drop) and oxalyl chloride (487 mg) is added and the resulting mixture stirred at room temperature for 30 minutes. The mixture is concentrated in vacuo to give a mixture of the acid chlorides.

Meanwhile sodium hydride (160 mg of a 60% dispersion in mineral oil) is added to a solution of 4-amino-3,5-dichloropyridine (445 mg) in dry tetrahydrofuran (10 mL) under a nitrogen atmosphere. The mixture is stirred for 30 minutes at room temperature and then a solution of the foregoing mixture of acid chlorides in dry tetrahydrofuran (5 mL) is added and stirring is continued for a further 3 hours. The reaction mixture is evaporated, the residue diluted with water and extracted into ethyl acetate. The extracts are dried (MgSO$_4$) and evaporated to give a pale yellow oil. The oil is partially purified by flash chromatography (n-pentane/ethyl acetate 4:1 v/v as eluent on silica) to give a mixture of (±)-N-(3,5-dichloropyrid-4-yl)-6-methoxy-5-exo-(8,9,10-trinorborn-5-en-2-yloxy)nicotinamide and (±)-N-(3,5-dichloropyrid-4-yl)-6-methoxy-5-(tricyclo[2.2.1.0.$^{2.6.}$]hept-2-yloxy)nicotinamide, (340 mg), as a white solid. This mixture is purified into the individual constituents by reversed phase high pressure liquid chromatography to give (±)-N-(3,5-dichloropyrid-4-yl)-6-methoxy-5-exo-(8,9,10-trinorborn-5-en-2-yloxy)nicotinamide (195 mg) as a white solid, m.p. 191-3° C., [$^1$Hnmr in D$_6$-DMSO shifts relative to Me$_4$Si: 1.42, 1H, m; 1.56, 1H, m; 1.75, 1H, m; 1.81, 1H, m; 2.91, 1H, m; 3.03, 1H, m; 3.96, 3H, s; 6.07, 1H, m; 6.35, 1H, m; 7.70, 1H, d; 8.42, 1H, d; 8.77, 2H, s; 10.61, 1H, br. s.]. [Elemental analysis: C, 55.9; H, 4.24; N, 10.2% calculated: C, 56.17; H, 4.22; N, 10.34%], and (±)-N-(3,5-dichloropyrid-4-yl)-6-methoxy-5-(tricyclo[2.2.1.0.$^{2.6.}$]hept-2-yloxy)nicotinamide monohydrate (74 mg) as a white crystalline solid, m.p. 213-4° C. [$^1$Hnmr in D$_6$-DMSO shifts relative to Me$_4$Si: 1.30, 2H, m; 1.36, 3H, m; 1.55, 1H, m; 1.83, 1H, m; 2.16, 1H, m; 3.96, 3H, s; 4.49, 1H, m; 7.78, 1H, d; 8.42, 1H, d; 8.77, 2H, s; 10.62, 1H, br. s.]. [Elemental analysis: C, 53.5; H, 4.01; N, 9.70% calculated: C, 53.79; H, 4.51; N, 9.90%]

Example 26

Compounds DA-FE

Thionyl chloride (0.5 mL) is added to a stirred mixture of 4-cyclopentyloxy-5-methoxypyridine-2-carboxylic acid (500 mg) in dry toluene (10 mL) containing dimethylformamide (1 drop). The mixture is stirred at gentle reflux for 1 hour, cooled and concentrated in vacuo to give the acid chloride, which is dissolved in dimethylformamide (10 mL).

Meanwhile sodium hydride (160 mg of a 60% dispersion in mineral oil) is added to a solution of 4-amino-3,5-dichloropyridine (665 mg) in dry dimethylformamide (10 mL), the mixture stirred for 1 hour and then added to the solution of the acid chloride. The resulting mixture is stirred for 6 hours, concentrated in vacuo, the residue diluted with water and the product extracted into ethyl acetate. The dried (MgSO$_4$) extracts are concentrated to a yellow/brown solid which is purified by flash chromatography (dichloromethane/methanol 50:1 v/v as eluent on silica) to give N-(3,5-dichloropyrid-4-yl)-4-cyclopentyloxy-5-methoxypyridine-2-carboxamide, (220 mg) as a white solid, m.p. 129-30° C. [Elemental analysis: C, 53.1; H, 4.44; N, 11.1% calculated: C, 53.42; H, 4.48; N, 10.99%]

By proceeding in a similar manner, but replacing 4-amino-3,5-dichloropyridine by the appropriate quantities of the corresponding aniline or aminopyridine derivatives and acid chlorides there are prepared:

N-(2,6-difluorophenyl)-4-cyclopentyloxy-5-methoxypyridine-2-carboxamide;

N-(2-chloro-6-fluorophenyl)-4-cyclopentyloxy-5-methoxypyridine-2-carboxamide;

N-(2-trifluoromethylphenyl)-4-cyclopentyloxy-5-methoxypyridine-2-carboxamide;

N-(2,4,6-trichlorophenyl)-4-cyclopentyloxy-5-methoxypyridine-2-carboxamide;

N-(2,6-dibromophenyl)-4-cyclopentyloxy-5-methoxypyridine-2-carboxamide;

N-(2-chloro-6-methylphenyl)-4-cyclopentyloxy-5-methoxypyridine-2-carboxamide;

N-(2,6-dichlorophenyl)-4-cyclopentyloxy-5-methoxypyridine-2-carboxamide;

N-(2-fluorophenyl)-4-cyclopentyloxy-5-methoxypyridine-2-carboxamide;

N-phenyl-4-cyclopentyloxy-5-methoxypyridine-2-carboxamide;

N-(2-methoxyphenyl)-4-cyclopentyloxy-5-methoxypyridine-2-carboxamide;

N-(2-chlorophenyl)-4-cyclopentyloxy-5-methoxypyridine-2-carboxamide;

N-(3-chlorophenyl)-4-cyclopentyloxy-5-methoxypyridine-2-carboxamide;

N-(4-methoxyphenyl)-4-cyclopentyloxy-5-methoxypyridine-2-carboxamide;

N-(2,6-dimethylphenyl)-4-cyclopentyloxy-5-methoxypyridine-2-carboxamide;

N-(2-methylthiophenyl)-4-cyclopentyloxy-5-methoxypyridine-2-carboxamide;

N-(2-bromophenyl)-4-cyclopentyloxy-5-methoxypyridine-2-carboxamide;

N-(2-methoxycarbonylphenyl)-4-cyclopentyloxy-5-methoxypyridine-2-carboxamide;

N-(2-aminosulfonylphenyl)-4-cyclopentyloxy-5-methoxypyridine-2-carboxamide;

N-(2-benzoylphenyl)-4-cyclopentyloxy-5-methoxypyridine-2-carboxamide;

N-(2-cyanophenyl)-4-cyclopentyloxy-5-methoxypyridine-2-carboxamide;

N-(2,5-dichlorophenyl)-4-cyclopentyloxy-5-methoxypyridine-2-carboxamide;

N-(3-methylphenyl)-4-cyclopentyloxy-5-methoxypyridine-2-carboxamide;

N-(2-nitrophenyl)-4-cyclopentyloxy-5-methoxypyridine-2-carboxamide;
N-(2-dimethylaminophenyl)-4-cyclopentyloxy-5-methoxypyridine-2-carboxamide;
N-(2-acetylphenyl)-4-cyclopentyloxy-5-methoxypyridine-2-carboxamide;
N-(2-hydroxyphenyl)-4-cyclopentyloxy-5-methoxypyridine-2-carboxamide;
N-(4-chloropyrid-3-yl)-4-cyclopentyloxy-5-methoxypyridine-2-carboxamide;
N-pyrid-2-yl-4-cyclopentyloxy-5-methoxypyridine-2-carboxamide;
N-pyrazin-2-yl-4-cyclopentyloxy-5-methoxypyridine-2-carboxamide;
N-pyrimidin-2-yl-4-cyclopentyloxy-5-methoxypyridine-2-carboxamide;
N-(3-methylpyrid-2-yl)-4-cyclopentyloxy-5-methoxypyridine-2-carboxamide;
N-pyrid-3-yl-4-cyclopentyloxy-5-methoxypyridine-2-carboxamide;
N-(3-chloropyrid-2-yl)-4-cyclopentyloxy-5-methoxypyridine-2-carboxamide;
N-(3-chloropyrid-4-yl)-4-cyclopentyloxy-5-methoxypyridine-2-carboxamide;
N-pyrid-4-yl-4-cyclopentyloxy-5-methoxypyridine-2-carboxamide;
N-(3,5-dimethylisoxazol-4-yl)-4-cyclopentyloxy-5-methoxypyridine-2-carboxamide;
N-(3,5-dibromopyrid-4-yl)-4-cyclopentyloxy-5-methoxypyridine-2-carboxamide;
N-(3,5-dimethylpyrid-4-yl)-4-cyclopentyloxy-5-methoxypyridine-2-carboxamide;
N-(2,6-dichloro-4-cyanophenyl)-4-cyclopentyloxy-5-methoxypyridine-2-carboxamide;
N-(2,6-dichloro-4-methoxycarbonylphenyl)-4-cyclopentyloxy-5-methoxypyridine-2-carboxamide;
N-(2,3,5-trifluoropyrid-4-yl)-4-cyclopentyloxy-5-methoxypyridine-2-carboxamide;
N-(2,6-dichloro-4-ethoxycarbonylphenyl)-4-cyclopentyloxy-5-methoxypyridine-2-carboxamide;
N-(2,6-dichloro-4-nitrophenyl)-4-cyclopentyloxy-5-methoxypyridine-2-carboxamide;
N-(3,5-difluoropyrid-4-yl)-4-cyclopentyloxy-5-methoxypyridine-2-carboxamide;
N-(3-bromo-5-chloropyrid-4-yl)-4-cyclopentyloxy-5-methoxypyridine-2-carboxamide;
N-(2,4,6-trifluorophenyl)-4-cyclopentyloxy-5-methoxypyridine-2-carboxamide;
N-(2,6-dichloro-4-methoxyphenyl)-4-cyclopentyloxy-5-methoxypyridine-2-carboxamide;
N-(4,6-dichloropyrimid-5-yl)-4-cyclopentyloxy-5-methoxypyridine-2-carboxamide;
N-(2,3,5,6-tetrafluoropyrid-4-yl)-4-cyclopentyloxy-5-methoxypyridine-2-carboxamide;
N-(3,5-dichloro-2,6-difluoropyrid-4-yl)-4-cyclopentyloxy-5-methoxypyridine-2-carboxamide;
N-(5-cyano-3-methylisothiazol-4-yl)-4-cyclopentyloxy-5-methoxypyridine-2-carboxamide;
N-(2,6-dichloro-4-carbamoylphenyl)-4-cyclopentyloxy-5-methoxypyridine-2-carboxamide;
N-(3-chloro-2,5,6-trifluoropyrid-4-yl)-4-cyclopentyloxy-5-methoxypyridine-2-carboxamide;
N-(4-nitrophenyl)-4-cyclopentyloxy-5-methoxypyridine-2-carboxamide;
N-(3-methyl-5-bromoisothiazol-4-yl)-4-cyclopentyloxy-5-methoxypyridine-2-carboxamide; and
N-(3,5-dimethylisothiazol-4-yl)-4-cyclopentyloxy-5-methoxypyridine-2-carboxamide.

Example 27

Compound FF

A mixture of N-(3,5-dichloropyrid-4-yl)-4-cyclopentyloxy-5-methoxypyridine-2-carboxamide (360 mg) and aqueous hydrogen peroxide (3 mL of strength 27.5%) in glacial acetic acid is heated at 75±5° C. for 3 hours. After cooling, the mixture is basified with 6 M aqueous sodium hydroxide and extracted with ethyl acetate. The extracts are washed with water, dried (MgSO$_4$) and evaporated to give a white solid. The solid is purified by flash chromatography (gradient elution with pentane/ethyl acetate 7:3 v/v changing to pentane/ethyl acetate 1:1 v/v on silica) to give N-(3,5-dichloro-1-oxido-4-pyridinio)-4-cyclopentyloxy-5-methoxypyridine-2-carboxamide as a white solid, m.p. 206-7° C. [Elemental analysis: C, 51.6; H, 4.37; N, 10.40% calculated: C, 51.27; H, 4.30; N, 10.55%].

Example 28

Compound FG

Oxalyl chloride (50 mL) in dry dichloromethane (1.5 mL) is cooled to −30° C. under a nitrogen atmosphere. Dimethyl sulphoxide (80 mL) is added, the mixture stirred for 10 minutes then a solution of (±)-1-(4-cyclopentyloxy-5-methoxypyridin-2-yl)-2-(3,5-dichloropyridin-4-yl)ethanol (210 mg) in dichloromethane (2.5 mL) is added and the mixture stirred for 3 hours. Triethylamine (0.2 mL) is added and the mixture is allowed to warm to room temperature. After pouring into water the organic phase is extracted into dichloromethane, the extracts washed sequentially with 1% aqueous sulphuric acid, water, saturated aqueous sodium bicarbonate and water. The extracts are dried (MgSO$_4$) and evaporated to give a solid. The solid is triturated with pentane, collected and dried to give 1-(4-cyclopentyloxy-5-methoxypyridin-2-yl)-2-(3,5-dichloropyridin-4-yl)ethanone (60 mg), as an off-white solid, m.p. 132° C. [Elemental analysis: C, 56.80; H, 4.92; N, 7.10% calculated: C, 56.71; H, 4.78; N, 7.35%].

Example 29

Compounds FH-FI

Thionyl chloride (0.4 mL) is added to a stirred solution of (±)-6-methoxy-5-exo-(8,9,10-trinorborn-2-yloxy)nicotinic acid (0.4 g) in toluene (10 mL) containing dimethylformamide (1 drop). The mixture is refluxed for 1 hour, cooled and evaporated to give the acid chloride which is dissolved in dimethylformamide (10 mL).

Meanwhile sodium hydride (80 mg of a 60% dispersion in mineral oil) is added to a solution of 4-amino-3,5-difluoropyridine (0.26 g) in dimethylformamide (10 mL) and the mixture stirred for 1 hour. The mixture is then added to the solution of the acid chloride and stirring continued for 6 hours. After evaporation of the solvent the residue is partitioned between ethyl acetate and water. The ethyl acetate phase is separated, washed with water, dried (MgSO$_4$) and evaporated to give an oil. The oil is purified by flash chromatography (n-pentane/ethylacetate 3:2 v/v as eluent on silica) to give an oil which upon triturating with n-pentane gave (±)-N-(3,5-difluoropyrid-4-yl)-6-methoxy-5-exo-(8,9,10-trinorborn-2-yloxy)nicotinamide, (0.19 g) as a solid, m.p. 120-1° C. [Elemental analysis: C, 61.3; H, 5.33; N, 11.3% calculated: C, 60.80; H, 5.10; N, 11.19%].

By proceeding in a similar manner, but replacing 4-amino-3,5-difluoropyridine with the appropriate quantity of 4-amino-3,5-dichloropyridine, there is prepared:

(±)-N-(3,5-dichloropyridin-4-yl)-6-methoxy-5-exo-(8,9,10-trinorborn-2-yloxy)nicotinamide, m.p. 169-170° C. [Elemental analysis: C, 55.90; H, 4.73; N, 10.30% calculated: C, 55.90; H, 4.69; N, 10.29%].

Example 30

Compounds FJ-FN

Thionyl chloride (0.65 mL) is added to a stirred solution of (±)-5-methoxy-4-(tricyclo[2.2.1.0.$^{2.6.}$]hept-2-yloxy)pyridine-2-carboxylic acid (0.4 g) in toluene (10 mL) containing dimethylformamide (1 drop). The mixture is refluxed for 2 hours, cooled and evaporated to give the acid chloride which is dissolved in dimethylformamide (5 mL).

Meanwhile sodium hydride (116 mg of a 60% dispersion in mineral oil) is added to a solution of N-(3,5-dichloropyridin-4-yl)acetamide (449 mg) in dimethylformamide (15 mL) and the mixture stirred for 2 hours. The mixture is then added to the solution of the acid chloride and stirring continued for 3 hours. After evaporation of the solvent the residue is partitioned between ethyl acetate and water. The ethyl acetate phase is separated, washed with water, dried (MgSO$_4$) and evaporated to give a brown oil. The oil is diluted with dimethylformamide (10 mL) and treated with piperidine (0.61 mL) for 18 hours. After concentrating the residue is partitioned between water and ethyl acetate. The ethyl acetate phase is washed with water, dried (MgSO$_4$) and evaporated. The residue is purified by flash chromatography (n-pentane/ethylacetate 7:3 v/v as eluent on silica) to give (±)-N-(3,5-dichloropyrid-4-yl)-5-methoxy-4-(tricyclo[2.2.1.0.$^{2.6.}$]hept-2-yloxy)pyridine-2-carboxamide, (0.35 g) as a white solid, m.p. 161-2° C. [Elemental analysis: C, 56.14; H, 4.29; Cl, 17.67; N, 10.13% calculated: C, 56.17; H, 4.22; Cl, 17.45; N, 10.34%].

By proceeding in a similar manner, but replacing 4-amino-3,5-dichlororopyridine with the appropriate quantity of 4-amino-3,5-difluoropyridine, there is prepared:

(±)-N-(3,5-difluoropyrid-4-yl)-5-methoxy-4-(tricyclo[2.2.1.0.$^{2.6.}$]hept-2-yloxy)pyridine-2-carboxamide hydrate, m.p. 64-5° C. [Elemental analysis: C, 60.34; H, 4.63; N, 11.18% calculated: C, 60.39; H, 4.67; N, 11.12%].

By proceeding in a similar manner, but replacing (t)-5-methoxy-4-(tricyclo[2.2.1.0.$^{2.6.}$]hept-2-yloxy)pyridine-2-carboxylic acid with the appropriate quantity of (±)-5-methoxy-4-(tetrahydrothiophen-3-yloxy)pyridine-2-carboxylic acid, there is prepared:

(±)-N-(3,5-dichloropyridin-4-yl)-5-methoxy-4-(tetrahydrothiophen-3-yloxy)pyridine-2-carboxamide, m.p. 171-2° C. [Elemental analysis: C, 48.4; H, 3.88; N, 10.63% calculated: C, 48.01; H, 3.78; N, 10.50%].

By proceeding in a similar manner, but replacing (±)-5-methoxy-4-(tricyclo[2.2.1.0.$^{2.6.}$]hept-2-yloxy)pyridine-2-carboxylic acid with the appropriate quantity of 4-cyclopropylmethoxy-5-methoxypyridine-2-carboxylic acid, there is prepared:

N-(3,5-dichloropyridin-4-yl)-4-cyclopropylmethoxy-5-methoxypyridine-2-carboxamide, m.p. 132-132.5° C. [Elemental analysis: C, 52.12; H, 4.12; Cl, 19.03; N, 11.40% calculated: C, 52.19; H, 4.11; Cl, 19.26; N, 11.41%].

By proceeding in a similar manner, but replacing (±)-5-methoxy-4-(tricyclo[2.2.1.0.$^{2.6.}$]hept-2-yloxy)pyridine-2-carboxylic acid with the appropriate quantity of 4-isopropyloxy-5-methoxypyridine-2-carboxylic acid, there is prepared:

N-(3,5-dichloropyridin-4-yl)-4-isopropyloxy-5-methoxypyridine-2-carboxamide, m.p. 142-3° C. [Elemental analysis: C, 50.3; H, 4.20; Cl, 20.10; N, 11.85% calculated: C, 50.58; H, 4.25; Cl, 19.91; N, 11.80%].

Example 31

Compounds FO-FS

Thionyl chloride (0.84 mL) is added to a stirred solution of (±)-5-methoxy-4-(tricyclo[2.2.1.0.$^{2.6.}$]hept-2-yloxy)pyridine-2-carboxylic acid (0.7 g) in toluene (10 mL) containing dimethylformamide (1 drop). The mixture is refluxed for 2 hours, cooled and evaporated to give the acid chloride which is dissolved in dimethylformamide (5 mL).

Meanwhile sodium hydride (150 mg of a 60% dispersion in mineral oil) is added to a solution of N-(3,5-dichloro-1-oxido-4-pyridinio)acetamide (663 mg) in dimethylformamide (20 mL) and the mixture stirred for 2 hours. The mixture is then added to the solution of the acid chloride and stirring continued for 3 hours. Piperidine (0.26 mL) is added and stirring continued for a further 4 hours. After concentrating in vacuo the residue is dissolved in dichloromethane, the mixture filtered, the filtrate treated with decolourizing charcoal and refiltered. Evaporation in vacuo gives a brown oil which is purified by reverse phase high pressure liquid chromatography (methanol/water 4:1 v/v) to give (±)-N-(3,5-dichloro-1-oxido-4-pyridinio)-5-methoxy-4-(tricyclo[2.2.1.0.$^{2.6}$]hept-2-yloxy)pyridine-2-carboxamide (60 mg) as a solid, m.p. 235-6° C. [Elemental analysis: C, 54.16; H, 4.21; N, 10.58% calculated: C, 56.04; H, 4.06; N, 9.95%].

By proceeding in a similar manner, but replacing N-(3,5-dichloro-1-oxido-4-pyridinio)acetamide with the appropriate quantity of N-(3,5-difluoro-1-oxido-4-pyridinio)acetamide, there is prepared:

(±)-N-(3,5-difluoro-1-oxido-4-pyridinio)-5-methoxy-4-(tricyclo[2.2.1.0.$^{2.6.}$]hept-2-yloxy)pyridine-2-carboxamide, m.p. 290° C. [Elemental analysis: C, 58.27; H, 4.57; N, 10.58% calculated: C, 58.61; H, 4.40; N, 10.79%].

By proceeding in a similar manner, but replacing (±)-5-methoxy-4-(tricyclo[2.2.1.0.$^{2.6.}$]hept-2-yloxy)pyridine-2-carboxylic acid with the appropriate quantity of 4-isopropyloxy-5-methoxypyridine-2-carboxylic acid, there is prepared:

N-(3,5-dichloro-1-oxido-4-pyridinio)-4-isopropyloxy-5-methoxypyridine-2-carboxamide, m.p. 220-1° C. [Elemental analysis: C, 48.65; H, 4.10; Cl, 19.24; N, 11.40% calculated: C, 48.40; H, 4.06; Cl, 19.05; N, 11.29%].

By proceeding in a similar manner, but replacing (±)-5-methoxy-4-(tricyclo[2.2.1.0.$^{2.6.}$]hept-2-yloxy)pyridine-2-carboxylic acid with the appropriate quantity of 4-cyclopropylmethoxy-5-methoxypyridine-2-carboxylic acid, there is prepared:

N-(3,5-dichloro-1-oxido-4-pyridinio)-4-cyclopropylmethoxy-5-methoxypyridine-2-carboxamide hemihydrate, m.p. 206-8° C. [Elemental analysis: C, 49.12; H, 3.94; Cl, 18.04; N, 10.61% calculated: C, 48.87; H, 4.11; Cl, 18.03; N, 10.69%].

By proceeding in a similar manner, but replacing (±)-5-methoxy-4-(tricyclo[2.2.1.0.$^{2.6.}$]hept-2-yloxy)pyridine-2-carboxylic acid with the appropriate quantity of (±)-5-methoxy-4-(tetrahydrothiophen-3-yloxy)pyridine-2-carboxylic acid, there is prepared:

(±)-N-(3,5-dichloro-1-oxido-4-pyridinio)-5-methoxy-4-(tetrahydrothiophen-3-yloxy)pyridine-2-carboxamide, m.p. 223-5° C. [Elemental analysis: C, 45.90; H, 3.61; Cl, 17.23; N, 10.07% calculated: C, 46.16; H, 3.63; Cl, 17.03; N, 10.09%].

Example 32

Compounds FT-FV

3-Chloroperoxybenzoic acid (2.16 g, of 50-60% grade peracid) is added to a solution of N-(3,5-dichloropyridin-4-yl)-4-cyclopentyloxy-5-methoxypyridine-2-carboxamide (0.8 g) in dichloromethane (80 mL) and the mixture refluxed for 8 hours. Another quantity of 3-chloroperoxybenzoic acid (0.5 g, of 50-60% grade peracid) is added and refluxing continued for 1 hour. After cooling the mixture is washed with saturated aqueous sodium bicarbonate, dried ($MgSO_4$) and evaporated. The residue is purified by flash chromatography (ethyl acetate/methanol 19:1 v/v as eluent on silica) to give N-(3,5-dichloro-1-oxido-4-pyridinio)-4-cyclopentyloxy-5-methoxy-1-oxidopyridinium-2-carboxamide, (740 mg), as an off-white solid, m.p. 154.5-155.5° C. [Elemental analysis: C, 49.44; H, 4.17; Cl, 17.04; N, 10.07% calculated: C, 49.29; H, 4.14; Cl, 17.12; N, 10.14%].

By proceeding in a similar manner, but replacing N-(3,5-dichloropyridin-4-yl)-4-cyclopentyloxy-5-methoxypyridine-2-carboxamide with the appropriate quantity of N-(3,5-dichloropyridin-4-yl)-4-cyclopropylmethoxy-5-methoxypyridine-2-carboxamide, there is prepared:
N-(3,5-dichloro-1-oxido-4-pyridinio)-4-cyclopropylmethoxy-5-methoxy-1-oxidopyridinium-2-carboxamide, m.p. 239-40° C. [Elemental analysis: C, 48.2; H, 3.93; N, 10.13% calculated: C, 48.01; H, 3.78; N, 10.53%].

By proceeding in a similar manner, but replacing N-(3,5-dichloropyridin-4-yl)-4-cyclopentyloxy-5-methoxypyridine-2-carboxamide with the appropriate quantity of N-(3,5-dichloropyridin-4-yl)-4-isopropyloxy-5-methoxypyridine-2-carboxamide, there is prepared:
N-(3,5-dichloro-1-oxido-4-pyridinio)-4-isopropyloxy-5-methoxy-1-oxidopyridinium-2-carboxamide, m.p. 236-8° C. [Elemental analysis: C, 46.38; H, 3.91; N, 10.48% calculated: C, 46.41; H, 3.89; N, 10.82%].

Example 33

Compounds FW-FX n-Butyllithium (10.6 mL of a 1.6 M solution in hexane) is added dropwise to a stirred solution of diisopropylamine (2.55 mL) in tetrahydrofuran (30 mL) at −78° C. under a nitrogen atmosphere. After stirring for 30 minutes a solution of 3,3-dichloro-4-methylpyridine (2.93 g) in tetrahydrofuran (15 mL) is added. After a further 30 minutes the resulting yellow suspension is treated with a solution of (±)-methyl 5-methoxy-4-(tricyclo[2.2.1.0.$^{2,6}$]hept-2-yloxy)pyridine-2-carboxylate (2.32 g) in tetrahydrofuran (25 mL), stirred for 30 minutes at −78° C. then allowed to warm to room temperature during 4 hours. After standing overnight the mixture is treated with aqueous ammonium chloride and the bulk of the tetrahydrofuran removed in vacuo. The residue is diluted with water and extracted with ethyl acetate. The extracts are washed with saline, dried ($MgSO_4$) and evaporated to give an oil. The oil is purified by flash chromatography (n-pentane/ethyl acetate 4:1v/v eluent on silica) to give 1-(5-methoxy-4-(tricyclo[2.2.1.0.$^{2,6}$]hept-2-yloxy)pyridin-2-yl)-2-(3,5-dichloropyridin-4-yl)ethanone (1.0 g), as a white solid, m.p. 156-7° C. [Elemental analysis: C, 59.10; H, 4.34; Cl, 17.37; N, 7.04% calculated: C, 59.27; H, 4.48; Cl, 17.50; N, 6.91%].

By proceeding in a similar manner, but replacing (±)-methyl 5-methoxy-4-(tricyclo[2.2.1.0.$^{2,6}$]hept-2-yloxy)pyridine-2-carboxylate with the appropriate quantity of (±)-methyl 5-methoxy-4-(tetrahydrothiophen-3-yloxy)pyridine-2-carboxylate, there is prepared:
(±)-1-(5-methoxy-4-(tetrahydrothiophen-3-yloxy)pyridin-2-yl)-2-(3,5-dichloropyridin-4-yl)ethanone as a white solid, m.p. 168-70° C. [Elemental analysis: C, 51.16; H, 4.06; Cl, 17.68; N, 7.04% calculated: C, 51.14; H, 4.04; Cl, 17.76; N, 7.02%].

Example 34

Compound FY

A solution of (±)-1-(4-(tricyclo[2.2.1.0.$^{2,6}$]hept-2-yloxy)-5-methoxypyridin-2-yl)-2-(3,5-dichloropyridin-4-yl)ethanone (340 mg) in dichloromethane (20 mL) is treated with 3.63 mL of a solution of 50% m-chloroperbenzoic acid (2 g) in dichloromethane (25 mL). The mixture is stirred at room temperature for 2 hours then refluxed for 6 hours. After cooling to room temperature the mixture is washed with saturated aqueous sodium bicarbonate, dried ($MgSO_4$) and evaporated to give a yellow solid. The solid is purified by flash chromatography (gradient elution pentane/ethyl acetate 7:3 v/v to neat ethyl acetate on silica) to give 1-(4-(tricyclo[2.2.1.0.$^{2,6}$]hept-2-yloxy)-5-methoxypyridin-2-yl)-2-(3,5-dichloro-1-oxido-4-pyridinio)ethanone (160 mg) as a white solid, m.p. 196-8° C. [Elemental analysis: C, 57.15; H, 4.47; N, 6.59% calculated: C, 57.02; H, 4.31; N, 6.65%].

Example 35

Compounds FZ-GA

Diphosphorus tetraiodide (53 mg) is added to a stirred solution of N-(3,5-dichloro-1-oxido-4-pyridinio)-4-cyclopropylmethoxy-5-methoxy-1-oxidopyridinium-2-carboxamide (150 mg) in dichloromethane (3 mL) under a nitrogen atmosphere. The brown solution is stirred for 10 minutes and the inorganic decomposed by the addition of aqueous sodium sulphite. The mixture is made alkaline by the addition of 30% aqueous sodium hydroxide. The dichloromethane layer is separated and the aqueous phase extracted with dichloromethane. The combined dichloromethane phases are dried ($MgSO_4$) and evaporated to give a white solid. The solid is purified by flash chromatography (ethyl acetate as eluent on silica) to afford N-(3,5-dichloropyridin-4-yl)-4-cyclopropylmethoxy-5-methoxy-1-oxidopyridinium-2-carboxamide (80 mg) as a white solid, m.p. 178-80° C. [Elemental analysis: C, 49.97; H, 3.94; N, 10.94% calculated: C, 50.01; H, 3.94; N, 10.94%].

By proceeding in a similar manner, but replacing N-(3,5-dichloro-1-oxido-4-pyridinio)-4-cyclopropylmethoxy-5-methoxy-1-oxidopyridinium-2-carboxamide with the appropriate quantity of N-(3,5-dichloro-1-oxido-4-pyridinio)-4-isopropyloxy-5-methoxy-1-oxidopyridinium-2-carboxamide, there is prepared:
N-(3,5-dichloropyridin-4-yl)-4-isopropyloxy-5-methoxy-1-oxidopyridinium-2-carboxamide, m.p. 174-6° C. [Elemental analysis: C, 53.17; H, 4.14; N, 7.27% calculated: C, 53.28; H, 4.21; N, 7.31%].

Example 36

Compound GB

A solution of chlorotrimethylsilane (0.18 mL) in acetonitrile (6 mL) is added dropwise to a stirred mixture of sodium iodide (648 mg), zinc dust (157 mg) and N-(3,5-dichloro-1-oxido-4-pyridinio)-4-cyclopentyloxy-5-methoxy-1-oxidopyridinium-2-carboxamide (600 mg) in acetonitrile with cooling to 0-5° C. The mixture is stirred for 3 hours at 0-5° C., diluted with diethyl ether, filtered and concentrated to give a yellow solid. The solid is purified by flash chromatography (ethyl acetate/n-pentane 7:3 v/v as eluent on silica) to give a white solid (200 mg), m.p. 259-60° C. which is an iodine adduct. The solid is dissolved in ethyl acetate containing a few drops of methanol and the solution stirred with 10% aqueous sodium thiosulphate (1.5 mL). After 3 hours the organic phase is separated, dried ($MgSO_4$) and evaporated to give N-(3,5-dichloropyridin-4-yl)-4-cyclopentyloxy-5-methoxy-1-oxidopyridinium-2-carboxamide hemihydrate (100 mg), as a white solid, m.p. 204-5° C. [Elemental analysis: C, 49.95; H, 4.19; N, 10.10% calculated: C, 50.13; H, 4.46; N, 10.3%].

Example 37

Compound GC-GE

A solution of 3-cyclopentyloxy-4-methoxybenzaldehyde (5 g) and 2-chloroaniline (2.5 mL) in toluene (60 mL) is heated at reflux under a Dean and Stark water trap for 3 hours. After concentration, the residue is dissolved in methanol (60 mL) and the stirred solution is treated at 0° C. with sodium cyanoborohydride (2.1 g). The temperature is allowed to rise to room temperature, and the stirring is continued for 2 hours, before dilution with ethyl acetate (100 mL) and washing with saline (100 mL). The organic layer is dried and concentrated, to give a brown oil. This oil is subjected to flash chromatography on silica gel, eluting with a mixture of ethyl acetate and hexane (1:4 v/v), to give N-(2-chlorophenyl)-3-cyclopentyloxy-4-methoxybenzylamine (0.64 g), in the form of an oil. [Elemental analysis: C, 69.5; H, 6.8; N, 4.1; Cl, 10.6%; calculated: C, 68.8; H, 6.7; N, 3.2; Cl, 10.7%].

By proceeding in a similar manner, but using 3-cyclopentyloxy-6-fluoro-4-methoxybenzaldehyde instead of 3-cyclopentyloxy-4-methoxybenzaldehyde, there is prepared N-(2-chlorophenyl)-3-cyclopentyloxy-6-fluoro-4-methoxybenzylamine.

By proceeding in a similar manner, but using 4-cyclopentyloxy-5-methoxypyridine-2-carboxaldehyde instead of 3-cyclopentyloxy-4-methoxybenzaldehyde, there is prepared N-(2-chlorophenyl)-4-cyclopentyloxy-5-methoxy-2-aminomethylpyridine.

Example 38

Compound GF-GJ

A stirred suspension of 2,6-dichlorobenzyltriphenylphosphonium bromide (2.5 g) in dry tetrahydrofuran (30 mL) is treated dropwise with a solution of potassium t-butoxide (0.56 g) in dry tetrahydrofuran (32 mL) at 0° C. After stirring at this temperature for 1 hour, it is treated with a solution of 3-cyclopentyloxy-4-methoxybenzaldehyde (1.1 g) in dry tetrahydrofuran (15 mL). The reaction mixture is stirred from 0° C. to 5° C. for 1.5 hours, and then allowed to warm to room temperature. After stirring overnight, the mixture is concentrated and the resulting residue is treated with ethyl acetate (200 mL). The resulting organic solution is filtered. The filtrate is concentrated and the resulting residue is subjected to flash chromatography, eluting with dichloromethane, to give trans-1-(3-cyclopentyloxy-4-methoxyphenyl)-2-(2,6-dichlorophenyl)ethene (1.16 g), m.p. 47-49° C. [Elemental analysis: C, 66.4; H, 5.6; Cl, 19.4%, calculated: C, 66.1; H, 5.55; Cl, 19.5%].

By proceeding in a similar manner, but using 3-cyclopentyloxy-6-fluoro-4-methoxybenzaldehyde instead of 3-cyclopentyloxy-4-methoxybenzaldehyde, there is prepared trans-2-(2,6-dichlorophenyl)-1-(3-cyclopentyloxy-6-fluoro-4-methoxy)phenylethene.

By proceeding in a manner similar, but using 3-cyclopentyloxy-6-fluoro-4-methoxybenzaldehyde and 2,6-difluorobenzyltriphenylphosphonium bromide, there is prepared trans-1-(3-cyclopentyloxy-6-fluoro-4-methoxyphenyl)-2-(2,6-difluorophenyl)ethene.

By proceeding in a similar manner, but using 4-cyclopentyloxy-5-methoxypyridine-2-carboxaldehyde instead of 3-cyclopentyloxy-4-methoxybenzaldehyde, there is prepared trans-2-(2,6-dichlorophenyl)-1-(4-cyclopentyloxy-5-methoxypyrid-2-yl)ethene.

By proceeding in a manner similar, but using 4-cyclopentyloxy-5-methoxypyridine-2-carboxaldehyde and 2,6-difluorobenzyltriphenyl-phosphonium bromide, there is prepared trans-1-(4-cyclopentyloxy-5-methoxypyrid-2-yl)-2-(2,6-difluorophenyl)ethene.

Example 39

Compound GK-GM

Pyridinium dichromate (3.6 g) in dry dichloromethane (40 mL) under nitrogen is treated with (±)-1-(3-cyclopentyloxy-4-methoxyphenyl)-2-(pyrid-4-yl)ethanol (2.0 g), in one portion. The resulting mixture is stirred for 1.5 hours, and then filtered through a pad of diatomaceous earth, and the pad is washed with diethyl ether. The combined filtrate and ethereal washings are washed with saturated aqueous cupric sulfate solution (2×30 mL), followed by water (30 mL), and then dried over magnesium sulfate. The solvent is removed under reduced pressure, and the resulting oily residue is subjected to flash chromatography on silica gel, eluting with ethyl acetate, to give 1-(3-cyclopentyloxy-4-methoxyphenyl)-2-(pyrid-4-yl)ethane-1,2-dione (0.4 g), in the form of a yellow solid, m.p. 117-119° C. [Elemental analysis: C, 70.1; H, 6.0; N, 4.1%; calculated: C, 70.1; H, 5.9; N, 4.3%].

By proceeding in a similar manner, but using (±)-1-(3-cyclopentyloxy-6-fluoro-4-methoxy)phenyl)-2-(pyrid-4-yl)ethanol instead of (±)-1-(3-cyclopentyloxy-4-methoxyphenyl)-2-(pyrid-4-yl)ethanol, there is prepared 1-[(3-cyclopentyloxy-6-fluoro-4-methoxy)phenyl]-2-(pyrid-4-yl)ethane-1,2-dione.

By proceeding in a similar manner, but using (±)-1-(4-cyclopentyloxy-5-methoxypyrid-2-yl)-2-(pyrid-4-yl)ethanol instead of (±)-1-(3-cyclopentyloxy-4-methoxyphenyl)-2-(pyrid-4-yl)ethanol, there is prepared 1-(4-cyclopentyloxy-5-methoxypyrid-2-yl)-2-(pyrid-4-yl)ethane-1,2-dione.

Example 40

Compound GN

By proceeding in a similar manner as in Example 26, but replacing 4-cyclopentyloxy-5-methoxypyridine-2-carboxylic acid by the appropriate quantity of 5-cyclopentyl-6-methoxypyridazine-3-carboxylic acid chloride there is prepared: N-(3,5-dichloropyrid-4-yl)-5-cyclopentyloxy-6-methoxypyridazine-3-carboxamide.

Example 41

Compound GO

Thionyl chloride (0.25 mL) is added to a stirred suspension of 4-cyclopentyloxy-5-difluoromethoxypyridine-2-carboxylic acid (0.23 g) in toulene (5 mL) containing dry dimethylformamide (1 drop). The mixture is refluxed for 1 hour under a nitrogen atmosphere, cooled and evaporated to give the acid chloride which is dissolved in dimethylformamide (5 mL).

Meanwhile sodium hydride (44 mg of a 60% dispersion in mineral oil) is added to stirred solution of N-(3,5-dichloropyridin-4-yl)acetamide (172 mg) in dimethylformamide (10 mL) and the mixture stirred for 1 hour. The mixture is then added to the solution of the acid chloride and the stirring continued for 1.5 hours at room temperature under a nitrogen atmosphere. Piperidine (0.23 mL) is added and the stirring continued for a further 1.5 hours. After evaporating the solvent, the residue, a brown oil, is purified by flash chromatography (n-pentane/ethyl acetate 7:3 v/v as eleunt on silica) to give N-(3,5-dichloropyridin-4-yl)-4-cyclopentyloxy-5-difluoromethoxypyridine-2-carboxamide, (0.14 g) as a white solid, m.p. 131-2° C. [Elemental analysis: C, 48.85, H, 3.57; N, 9.91%, calculated: C, 48.82; H, 3.62; N, 10.05%], [$^1$Hnmr in $CDCl_3$ with $Me_4Si$ as standard: 1.71, 2H, m: 1.83, 2H, m; 1.93, 2H, m; 2.03, 2H, m; 5.03, 1H, m; 6.64, 1H, t, J=74 Hz; 7.90, 1H, s; 8.37, 1H, s; 8.58, 2H, s: 9.88, 1H, br s.].

Reference Example 1

A mixture of 3,4-dimethoxy-6-fluorobenzaldehyde (3.7 g) and concentrated sulphuric acid (30 mL) is heated on a steam bath for 19 hours. The mixture is cooled, treated with ice-water (100 g) and stirred at 0° C. for 30 minutes. The mixture is extracted with chloroform (5×100 mL). The combined organic extracts are extracted with aqueous sodium hydroxide solution (2×200 mL; 2 N). These aqueous extracts are acidified, by treatment with concentrated hydrochloric acid, with cooling, and the rust coloured solid formed is subjected to flash chromatography [using a solvent gradient of 3:1 to 2:1 v/v petroleum ether (b.p. 60-80° C.) and ethyl acetate as eluent on a silica gel column], to give 6-fluoro-3-hydroxy-4-methoxybenzaldehyde (1.67 g) in the form of a white solid, m.p. 153-154° C. [NMR (DMSO): 9.56 (s, 1H), 7.12 (d, 1H, J=8 Hz), 7.01 (d, 1H, J=12 Hz), 3.88 (s, 3H)].

By proceeding in a similar manner, but using 5,6-dimethoxypyridazine-3-carboxaldehyde instead of 3,4-dimethoxy-6-fluorobenzaldehyde, there is prepared 5-hydroxy-6-methoxypyridazine-3-carboxaldehyde.

Reference Example 2

A mixture of 6-fluoro-3-hydroxy-4-methoxybenzaldehyde (2 g), potassium carbonate (1.66 g) and anhydrous dimethylformamide (20 mL) is treated with cyclopentyl bromide (1.62 mL) and heated on a steam bath for 43 hours. The mixture is cooled, poured into water (200 mL) and extracted with diethyl ether (3×100 mL). The combined ethereal extracts are washed with sodium hydroxide solution (2×50 mL; 2 N), and brine (2×50 mL), dried over magnesium sulphate and concentrated. The residual brown oil is subjected to flash chromatography [a solvent gradient of 9:1 to 4:1 v/v petroleum ether (b.p. 60-80° C.) and ethyl acetate is used as eluent on a silica gel column] to give 3-cyclopentyloxy-6-fluoro-4-methoxybenzaldehyde (1.42 g) in the form of a yellow oil. [NMR ($CDCl_3$): 10.22 (s, 1H), 7.27 (d, 1H, J=8 Hz), 6.63 (d, 1H, J=16 Hz), 4.81-4.76 (m, 1H), 3.91 (s, 3H), 2.01-1.57 (m, 8H)].

By proceeding in a similar manner but using the appropriate quantities of the appropriate alkyl halides there are prepared:
2-Fluoro-5-isopropoxy-4-methoxybenzaldehyde, [NMR ($CDCl_3$): 10.21 (s, 1H), 7.30 (d, 1H, J=8 Hz), 6.64 (d, 1H, J=12 Hz), 4.55 (m, 1H), 3.92 (s, 3H), 1.36 (d, 6H, J=7 Hz)];
3-cyclohexyloxy-6-fluoro-4-methoxybenzaldehyde;
3-butoxy-6-fluoro-4-methoxybenzaldehyde; and
3-propoxy-6-fluoro-4-methoxybenzaldehyde.

By proceeding in a similar manner, but using the appropriate quantity of 5-hydroxy-6-methoxypyridazine-3-carboxaldehyde instead of 6-fluoro-3-hydroxy-4-methoxybenzaldehyde, there is prepared 5-cyclopentyl-6-methoxypyridazine-3-carboxaldehyde.

Reference Example 3

A solution of 3-cyclopentyloxy-6-fluoro-4-methoxybenzaldehyde (1.4 g) in glacial acetic acid (20 mL) is treated with sulfamic acid (0.82 g) at room temperature and stirred for 10 minutes. The resulting yellow solution is cooled to 0° C. and treated with a solution of sodium chlorite (0.69 g of an 80% pure sample) in water (20 mL) during 10 minutes. The resulting yellow suspension is stirred at room temperature for 3 hours, poured into water (100 mL) and filtered to give 3-cyclopentyloxy-6-fluoro-4-methoxybenzoic acid (0.88 g), in the form of a white solid. [NMR ($CDCl_3$): 7.46 (d, 1H, J=8 Hz), 6.65 (d, 1H, J=12 Hz), 4.80-0.76 (m, 1H), 3.90 (s, 3H), 2.01-1.58 (m, 8H)].

By proceeding in a similar manner but using the appropriate quantities of the appropriate benzaldehydes there are prepared:
2-Fluoro-5-isopropoxy-4-methoxybenzoic acid;
3-cyclohexyloxy-6-fluoro-4-methoxybenzoic acid;
3-butoxy-6-fluoro-4-methoxybenzoic acid;
3-propoxy-6-fluoro-4-methoxybenzoic acid; and
5-cyclopentyl-6-methoxypyridazine-3-carboxylic acid.

Reference Example 4

A solution of 3-hydroxy-4-methoxybenzaldehyde (14.20 g) in dry dimethylformamide (300 mL) is treated portionwise with sodium hydride (60% dispersion in oil; 3.70 g) at room temperature under nitrogen. 3-Chlorocyclo-pentene (9.6 mL) is added and the resulting mixture is stirred overnight. The solvent is then removed under reduced pressure and the residue is partitioned between water (500 mL) and dichloromethane (500 mL) and the aqueous layer is further extracted with dichloromethane (500 mL). The combined organic extracts are dried and evaporated under reduced pressure and the residue is subjected to flash chromatography on silica gel, eluting with a mixture of ethyl acetate and pentane (1:1 v/v), to give 3-cyclopent-2-enyloxy-4-methoxybenzaldehyde, in the form of a pale brown oil (11.2 g).

By proceeding in a similar manner, but using the appropriate quantity of 6-fluoro-3-hydroxy-4-methoxybenzaldehyde, there is prepared 3-cyclopent-2-enyloxy-6-fluoro-4-methoxybenzaldehyde.

Reference Example 5

A solution of 3-cyclopent-2-enyloxy-4-methoxybenzaldehyde (7.70 g) in t-butanol (160 mL) and 2-methyl-2-butene (40 mL) is treated dropwise with an aqueous solution (150 mL) containing sodium chlorite (80% technical grade; 4.39 g) and sodium dihydrogen phosphate (38.49 g), and left to stand overnight. The resulting mixture is extracted with dichloromethane (2×250 mL), and the combined organic layers are dried over sodium sulfate, the solvent is removed under reduced pressure, and the resulting residue is recrystallized from ethyl acetate, to give 3-cyclopent-2-enyloxy-4-methoxybenzoic acid (5.89 g), in the form of a colorless solid. m.p. 160-163° C. [Elemental analysis: C, 66.4; H, 6.0%; calculated: C, 66.7; H, 6.0%].

By proceeding in a similar manner, but using the appropriate quantity of 3-cyclopent-2-enyloxy-6-fluoro-4-methoxybenzaldehyde, there is prepared 3-cyclopent-2-enyloxy-6-fluoro-4-methoxybenzoic acid.

Reference Example 6

A solution of 3-cyclopent-2-enyloxy-4-methoxybenzoic acid. (5.89 g) in dry dichloromethane (50 mL) under nitrogen at room temperature is treated with triethylamine (10.50 mL), followed by oxalyl chloride (2.40 mL). The resulting mixture is stirred for 2.5 hours, then most of the solvent is removed under reduced pressure, and the resulting residue is taken up in dry tetrahydrofuran (50 mL) and filtered through a pad of diatomaceous earth. The resulting solution, containing 3-cyclopent-2-enyloxy-4-methoxybenzoyl chloride, is used immediately without further purification.

By proceeding in a similar manner, but using the appropriate quantity of 3-cyclopent-2-enyloxy-6-fluoro-4-methoxybenzoic acid, there is prepared 3-cyclopent-2-enyloxy-6-fluoro-4-methoxybenzoyl chloride.

Reference Example 7

A stirred suspension of sodium hydride (60% in oil, 0.88 g) in dry dimethylformamide (44 mL) under nitrogen at between 5-10° C. is treated with a solution of 3-hydroxy-4-methoxy benzaldehyde (3.35 g) in dry dimethylformamide (6.3 mL). The resulting mixture is allowed to warm to room temperature and stirred for 40 minutes before recooling to between 5-10° C. A solution of 4-(p-toluenesulfonoxy)cyclopentene (5.24 g) in dry dimethylformamide (12.6 mL) is added dropwise maintaining the temperature below 10° C. The resulting mixture is allowed to warm to room temperature, left to stand for 46 hours, and then poured into 5% aqueous potassium carbonate (305 mL). t-Butyl methyl ether is added (150 mL), and the layers are thoroughly stirred and separated. The aqueous layer is further extracted with t-butyl methyl ether (2×75 mL), the combined organic extracts are washed with water (3×30 mL) and dried over magnesium sulfate. The solvent is removed under reduced pressure and the resulting residue is subjected to flash chromatography on silica gel, eluting with mixtures of ethyl acetate and pentane (1:10 to 3:10), to give 3-cyclopent-3-enyloxy-4-methoxybenzaldehyde as a pale amber viscous oil that slowly crystallizes on standing (1.75 g). Recrystallization of a portion (0.5 g) from cyclohexane gives an analytically pure sample (0.4 g), m.p. 60-62° C. [Elemental analysis: C, 71.8; H, 6.5%; calculated: C, 71.5; H, 6.8%].

By proceeding in a similar manner, but using the appropriate quantity of 6-fluoro-3-hydroxy-4-methoxybenzaldehyde, there is prepared 3-cyclopent-3-enyloxy-6-fluoro-4-methoxybenzaldehyde.

Reference Example 8

A stirred solution of 3-cyclopent-3-enyloxy-4-methoxybenzaldehyde (1.75 g) in t-butanol (36.5 mL) and 2-methyl-2-butene (9.0 mL) is treated dropwise with an aqueous solution (34 mL) containing sodium chlorite (80% technical grade; 1.0 g) and sodium dihydrogen phosphate (8.75 g). The resulting mixture is further stirred for 5 hours, the layers are separated and the aqueous layer is extracted with t-butyl methyl ether (3×30 mL). The combined organic layers are washed with water (2×15 mL), dried over sodium sulfate and the solvent removed under reduced pressure. The resulting residue is recrystallized from ethyl acetate to give 3-cyclopent-3-enyloxy-4-methoxybenzoic acid (1.31 g), in the form of a colorless solid, m.p. 171-173° C. [Elemental analysis: C, 66.6; H, 6.0%; calculated: C, 66.7; H, 6.0%].

By proceeding in a similar manner, but using the appropriate quantity of 3-cyclopent-3-enyloxy-6-fluoro-4-methoxybenzaldehyde, there is prepared 3-cyclopent-3-enyloxy-6-fluoro-4-methoxybenzoic acid.

Reference Example 9

A solution of 3-cyclopent-3-enyloxy-4-methoxybenzoic acid (1.33 g) in dry tetrahydrofuran (20 mL) under nitrogen at room temperature is treated with triethylamine (2.36 mL), followed by oxalyl chloride (0.70 mL). The resulting mixture is stirred for 1 hour and then filtered through a pad of diatomaceous earth. The solid collected is washed with dry tetrahydrofuran (10 mL). The resulting combined filtrates, containing 3-cyclopent-3-enyloxy-4-methoxybenzoyl chloride, is used immediately without further purification.

By proceeding in a similar manner, but using the appropriate quantity of 3-cyclopent-3-enyloxy-6-fluoro-4-methoxybenzoic acid, there is prepared 3-cyclopent-3-enyloxy-6-fluoro-4-methoxybenzoyl chloride.

Reference Example 10

A mixture of 2-fluoro-5-hydroxy-4-methoxybenzaldehyde (3 g), endonorborneol (1.33 g) and triphenylphosphine (4.62 g) are dissolved in dry tetrahydrofuran (3.5 mL) and treated with diisopropylazodicarboxylate (3.6 g). The mixture is heated with stirring at reflux for 24 hours, cooled and treated with water (75 mL). The mixture is extracted with dichloromethane (3×100 mL) and the combined organic extracts washed with 2 N sodium hydroxide (2×75 mL), brine (75 mL), dried (magnesium sulfate) and concentrated to give 3-exonorbornyloxy-6-fluoro-4-methoxybenzaldehyde as a brown oil (2.1 g). [NMR (CDCl$_3$): 10.24 (s, 1H), 7.23 (d, 1H, J=7 Hz), 6.64 (d, 1H, J=12 Hz), 4.22 (d, 1H, J=8 Hz), 3.92 (s, 3H), 2.5 (d, 1H, J=5 Hz), 2.33 (bs, 1H), 1.86-1.1 (m, 10H)].

Reference Example 11

To a solution of diisopropylamine (0.16 g) in tetrahydrofuran (2 mL) at −78° C. is added a 2.5 N solution of n-butyl lithium in hexanes (0.62 mL). The solution is allowed to warm to −10° C. and cooled back to −78° C. A solution of 3,5-dichloro-4-methylpyridine (0.25 g) in dry tetrahydrofuran (4 mL) is added, stirred for 0.5 hours at −60° C. and treated with 3-cyclopentyloxy-6-fluoro-4-methoxybenzaldehyde (0.25 g) in dry tetrahydrofuran (4 mL). The reaction mixture is allowed to warm to room temperature over 1 hour and stirred overnight. The mixture is treated with 2N ammonium chloride (50 mL) and extracted with ethyl acetate (3×50 mL). The combined organic extracts are washed with brine (50 mL), dried (magnesium sulfate) and evaporated to give 2-(3,5-dichloropyrid-4-yl)-1-(3-cyclopentyloxy-6-fluoro-4-methoxyphenyl)ethanol (0.22 g). [NMR (CDCl$_3$): 8.44 (s, 2H), 6.97 (d, 1H, J=7 Hz), 6.56 (d, 1H, J=12 Hz), 5.34 (m, 1H), 4.74 (m, 1H), 3.83 (s, 3H), 3.5 (dd, 1H, J=8 Hz, 8 Hz), 3.32 (dd, 1H, J=5 Hz, 6 Hz), 2.07 (d, 1H, J=6 Hz), 1.93-1.55 (m, 8H)].

Reference Example 12

A mixture of 2-fluoro-5-isopropoxy-4-methoxybenzoic acid (7.2 g) and lithium iodide (24 g) in collidine (120 mL) is heated at 150° C. overnight, cooled and dissolved in 2 N sodium hydroxide (200 mL) and washed with ethyl acetate (3×150 mL). The aqueous solution is acidified to pH 1 with concentrated hydrochloric acid and extracted with ethyl acetate (3×100 mL). The combined organic layers are dried (magnesium sulfate) and concentrated to give an oil. The oil is subjected to mplc on silica gel using petroleum ether:ethyl acetate (2:1 v/v) as eluent to give 2-fluoro-4-hydroxy-5-isopropylbenzoic acid (5.7 g). [NMR (DMSO): 7.32 (d, 1H, J=8 Hz), 6.67 (d, 1H, J=12 Hz), 4.47 (m, 1H), 1.24 (d, 6H, J=6 Hz)].

By proceeding in a similar manner, but using the appropriate quantities of the appropriate acid, is prepared 3-cyclopentyloxy-6-fluoro-4-hydroxybenzoic acid, [NMR (CDCl$_3$): 7.44 (d, 1H, J=8 Hz), 6.73 (d, 1H, J=12 Hz), 4.86 (m, 1H), 2.05-1.63 (m, 8H)].

Reference Example 13

2-Fluoro-4-hydroxy-5-isopropyloxybenzoic acid (5.7 g) is dissolved in methanol (200 mL) and concentrated sulfuric acid (1 mL) and heated at 70° C. for 5 hours. The solution is concentrated and the resultant oil subjected to mplc on silica gel using petroleum ether:ethyl acetate (4:1 v/v) as eluent to give methyl-2-fluoro-4-hydroxy-5-isopropyloxybenzoate (5.7 g). [NMR (CDCl$_3$) 7.38 (d, 1H, J=7 Hz), 6.67 (d, 1H, J=12 Hz), 4.85 (m, 1H), 3.9 (s, 3H), 1.3 (d, 6H, J=7 Hz)].

By proceeding in a similar manner, but using the appropriate quantities of the appropriate acid, is prepared:
Methyl-3-cyclopentyloxy-4-hydroxy-6-fluorobenzoate,
[NM R (CDCl$_3$): 7.38 (d, 1H, J=6 Hz), 6.68 (d, 1H, J=12 Hz), 4.87 (m, 1H), 3.91 (s, 3H), 2.03-1.62 (m, 8H)].

Reference Example 14

Methyl-2-fluoro-4-hydroxy-5-isopropyloxybenzoate (5.7 g) is dissolved in dimethylformamide (150 mL) and treated with potassium carbonate (5.1 g) and potassium iodide (2 g). Chlorodifluoromethane is slowly bubbled through the stirred solution which is slowly heated to 70° C. After 7 hours the reaction is terminated by cooling and quenching with water (100 mL). The solution is extracted with ethyl acetate (4×100 mL) and the combined organic extracts washed with brine (200 mL) and dried (magnesium sulfate). The organic solution is evaporated to give an oil, which is subjected to mplc on silica gel using petroleum ether:ethyl acetate (9:1 v/v) as eluent to give methyl-4-difluoromethoxy-2-fluoro-5-isopropyloxybenzoic acid (5.8 g). [NMR (CDCl$_3$): 7.52 (d, 1H, J=8 Hz), 6.97 (d, 1H, J=12 Hz), 6.67 (t, 1H, J=72 Hz), 4.56 (m, 1H), 3.93 (s, 3H), 1.36 (d, 6H, J=6 Hz)].

By proceeding in a similar manner, but using the appropriate quantity of the appropriate ester is prepared:
Methyl-3-cyclopentyloxy-4-difluoromethoxy-6-fluorobenzoate. [NMR (CDCl$_3$): 7.50 (d, 1H, J=7 Hz), 6.97 (d, 1H, J=12 Hz), 6.65 (t, 1H, J=72 Hz), 4.83 (m, 1H), 3.94 (s, 3H), 1.98-1.62 (m, 8H)].

Reference Example 15

Methyl-2-fluoro-4-difluoromethoxy-5-isopropyloxybenzoate (5.8 g) is dissolved in methanol (100 mL) and water (30 mL) with potassium carbonate (3.9 g) and stirred at 70° C. for 4 hours. After concentration the residue is dissolved in water (150 mL) and washed with ether (150 mL). The aqueous solution is acidified with 2 M hydrochloric acid and the precipitate collected as 2-fluoro-4-difluoromethoxy-5-isopropyloxybenzoic acid (5.2 g). [NMR (CDCl$_3$): 7.60 (d, 1H, J=7 Hz), 7.02 (d, 1H, J=12 Hz), 6.70 (t, 1H, J=72 Hz), 4.57 (m, 1H), 1.38 (d, 6H, J=7 Hz)].

By proceeding in a similar manner, but using the appropriate quantities of the appropriate ester is prepared 3-cyclopentyloxy-4-difluoromethoxy-6-fluorobenzoic acid. [NMR (CDCl$_3$): 7.57 (d, 1H, J=8 Hz), 7.02 (d, 1H, J=12 Hz), 6.68 (t, 1H, J=72 Hz), 4.84 (m, 1H), 2.0-1.6 (m, 8H)].

Reference Example 16

A stirred solution of diisopropylamine (14 mL) in dry tetrahydrofuran (150 mL), is treated dropwise with a solution of butyl lithium in hexanes (40 mL; 2.5 M), under nitrogen, while keeping the temperature at below −70° C. The resulting mixture is then stirred for a further period of 30 minutes at below −70° C. The stirred mixture, while it is still maintained at below −70° C., is then treated dropwise with a solution of 4-picoline (9.3 g) in dry tetrahydrofuran (20 mL). The stirred mixture is maintained at below −70° C. for a further 45 minutes. The stirred mixture, while it is still maintained at below −70° C., is then treated with a solution of 3-cyclopentyloxy-4-methoxybenzaldehyde (22.0 g) in dry tetrahydrofuran (100 mL), and it is stirred at below −70° C. for a further 30 minutes. The resulting mixture is then allowed to warm to room temperature overnight, and then treated with saturated aqueous ammonium chloride solution (200 mL). The layers are separated and the aqueous layer is further extracted with ethyl acetate (3×300 mL). The combined organic extracts are dried over magnesium sulfate and evaporated to dryness. The resulting residue is recrystallized from ethyl acetate, to give (±)-1-(3-cyclopentyloxy-4-methoxyphenyl)-2-(pyrid-4-yl) ethanol (28.5 g), in the form of a cream solid, m.p. 102-103° C.

By proceeding in a similar manner using 3-cyclopentyloxy-6-fluoro-4-methoxybenzaldehyde (that is prepared as in Reference Example 2) instead of 3-cyclopentyloxy-4-methoxybenzaldehyde, there is prepared (±)-1-(3-cyclopentyloxy-6-fluoro-4-methoxy)phenyl)-2-(pyrid-4-yl)ethanol.

Reference Example 17

Sodium methoxide in methanol (82.65 mL of a 1 M solution) is added slowly to a stirred solution of methyl 6-chloro-5-nitronicotinate (17 g) in anhydrous methanol (250 mL) and the mixture stirred for 8 hours. The mixture is concentrated, the residue treated with water and then extracted into ethyl acetate. The extracts are washed with water, treated with decolourising charcoal and dried (MgSO$_4$). Concentration afforded methyl 6-methoxy-5-nitronicotinate (9.8 g) as an orange solid. Recrystallisation from cyclohexane afforded white needles, m.p. 118-9° C.

Reference Example 18

A solution of methyl 6-methoxy-5-nitronicotinate (5.4 g) in ethyl acetate (120 mL) is hydrogenated using 5% palladium on carbon (1 g) as catalyst. When hydrogen uptake ceased the mixture is filtered through a pad of diatomaceous earth and the filtrate evaporated. The residue is triturated with n-pentane and methyl t-butyl ether to give methyl 5-amino-6-methoxynicotinoate (4.3 g) as a light-brown solid, m.p. 108-9° C. [Elemental analysis: C, 52.99; H, 5.49; N, 15.25%. calculated: C, 52.74; H, 5.53; N, 15.38%.]

Reference Example 19

Concentrated hydrochloric acid (9.06 mL of strength 36%) is added to a stirred suspension of methyl 5-amino-6-methoxynicotinoate (3.3 g) in water (20 mL). The mixture is cooled to 0° C. and treated dropwise with a solution of sodium nitrite (1.37 g) in water (5 mL). After 30 minutes at 0° C. a solution of sodium tetrafluoroborate (2.84 g) in water (10 mL) is added. After a further 30 minutes the precipitated diazonium salt is collected, washed with a little ice-cold water then with diethyl ether and sucked dry. Potassium carbonate (1.0 g) is added to trifluoroacetic acid (32 mL) at 0° C. followed by the addition of the diazonium salt in one portion. The mixture is stirred at reflux for 18 hours, cooled then poured into iced water and stirred for 1 hour. The aqueous mixture is neutralised with solid sodium bicarbonate and extracted with ethyl acetate. The extracts are washed with water and dried (MgSO$_4$). Concentration afforded methyl 5-hydroxy-6-methoxynicotinoate (2.86 g) as a beige solid. This material is used without further purification.

Reference Example 20

A mixture of methyl 5-hydroxy-6-methoxynicotinoate (250 mg), anhydrous potassium carbonate (600 mg) and cyclopentyl bromide (0.26 mL) in dry dimethylformamide (5 mL) is stirred and heated at 60±5° C. for 24 hours. The mixture is cooled to room temperature, diluted with water and extracted with ethyl acetate. The extracts are washed with water and dried (MgSO$_4$). Concentration gave methyl 5-cyclopentyloxy-6-methoxynicotinoate (290 mg) as an oil.

Reference Example 21

A solution of potassium hydroxide (168 mg) in water (1 mL) is added to a solution of methyl 5-cyclopentyloxy-6-methoxynicotinoate (250 mg) in methanol (3 mL) and the mixture stirred for 4 hours then allowed to stand at room temperature overnight. The mixture is concentrated, the residue dissolved in water and the mixture adjusted to pH 6 by the addition of concentrated hydrochloric acid. The mixture is extracted with ethyl acetate, the extracts dried (MgSO$_4$) and concentrated to give a cream solid. The solid is dried at 100° C. to give 5-cyclopentyloxy-6-methoxynicotinic acid (140 mg), m.p. 191-2° C. [Elemental analysis: C, 60.7; H, 6.43; N, 5.78%. calculated: C, 60.75; H, 6.37; N, 5.90%.].

Reference Example 22

6-Chloro-5-methoxypyridine-2-carbonyl chloride (5.8 g) is added to dry cyclopentanol (50 mL) and the mixture refluxed for 4 hours. The mixture is concentrated, the residue dissolved in ethyl acetate (400 mL) and the ethyl acetate solution is washed with water (3×250 mL). After drying (MgSO$_4$) the solution is evaporated to dryness to give cyclopentyl 6-chloro-5-methoxypyridine-2-carboxylate (6.3 g) as a buff solid, m.p. 90-92° C. [Elemental analysis: C, 55.9; H, 5.47; Cl, 13.9; N, 5.48%. calculated: C, 56.36; H, 5.52; Cl, 13.8; N, 5.48%.].

Reference Example 23

Sodium hydride (887 mg of a 60% dispersion in oil) is added to a solution of cyclopentanol (3.35 mL) in dry tetrahydrofuran (127 mL) and the mixture stirred for 1.5 hours. Cyclopentyl 6-chloro-5-methoxypyridine-2-carboxylate (6.3 g) is added and the mixture is stirred at room temperature for 21 hours. The mixture is poured into saturated aqueous ammonium chloride (500 mL) and the resulting mixture extracted with ethyl acetate (2×500 mL). The combined extracts are washed with saturated aqueous sodium bicarbonate (500 mL) and water (500 mL). After drying (MgSO$_4$) the solution is evaporated to dryness to give a yellow oil which is purified by flash chromatography (silica with pentane/ethyl acetate 9:1 v/v as eluent) affording cyclopentyl 6-cyclopentyloxy-5-methoxypyridine-2-carboxylate (3.6 g) as an oil.

Reference Example 24

Potassium hydroxide (1.98 g) in water (12 mL) is added to a solution of cyclopentyl 6-cyclopentyloxy-5-methoxypyridine-2-carboxylate (3.6 g) in methanol (35 mL) and the mixture stirred at room temperature for 2.5 hours. The solution is concentrated to half of the original volume and diluted with water. The solution is acidified to pH 4 with concentrated hydrochloric acid and the product extracted with ethyl acetate. The extracts are dried (MgSO$_4$) and concentrated to give 6-cyclopentyloxy-5-methoxypyridine-2-carboxylic acid (1.38 g) as a yellow solid, m.p. 96-99° C.

Reference Example 25

Sodium thiomethoxide (9.1 g) in dry methanol (50 mL) is added dropwise to a stirred solution of methyl 6-chloro-5-nitronicotinate (25.1 g) in dry methanol (400 mL) and the mixture stirred for 4 hours. The pasty mixture is evaporated to low volume, diluted with water and the product extracted into ethyl acetate. The extracts are washed with water and brine, and finally dried (MgSO$_4$). Evaporation gave methyl 6-methylthio-5-nitronicotinate (16.8 g) as a yellow solid. The solid can be recrystallised from cyclohexane to give a yellow solid m.p. 115-6° C.

Reference Example 26

Iron powder (22.4 g) is added portionwise to a solution of methyl 6-methylthio-5-nitronicotinate (16.8 g) in a mixture of glacial acetic acid (175 mL) and water (30 mL) whilst heating at 95±5° C. After the addition is complete the mixture is heated for a further 1.5 hours. The cooled mixture is diluted with water and extracted with ethyl acetate. The extracts are dried (MgSO$_4$), treated with decolourising charcoal and evaporated to give methyl 5-amino-6-methylthionicotinoate as a dark yellow solid (12.5 g).

Reference Example 27

Concentrated hydrochloric acid (31.2 mL) is added to a stirred suspension of methyl 5-amino-6-methylthionicotinoate (12.5 g) in water (70 mL). The stirred mixture is cooled to 0-5° C. and treated dropwise with a solution of sodium nitrite (4.75 g) in water (35 mL), then stirred for a further 30 minutes at 0-5° C. A solution of sodium tetrafluoroborate (9.84 g) in water (35 mL) is added and the mixture stirred for 1 hours. The water is removed in vacuo, the solid residue triturated with diethyl ether, collected and pumped dry. The solid is added portionwise to a mixture of anhydrous potassium carbonate (3.5 g) and trifluoroacetic acid (100 mL) and the resulting mixture stirred at room temperature for 72 hours. The mixture is evaporated to low volume, diluted with water and the product extracted into ethyl acetate. The extracts are washed with water, dried (MgSO$_4$) and evaporated to afford a dark oil. The oil is triturated with n-pentane then methyl t.butyl ether to give methyl 5-hydroxy-6-methylthionicotinoate (8.9 g) as a light brown solid, mp. 152-3° C.

Reference Example 28

Cyclopentyl bromide (0.78 mL) is added to a stirred mixture of methyl 5-hydroxy-6-methylthionicotinoate (810 mg) and anhydrous potassium carbonate (1.8 g) in dry dimethylformamide (15 mL). The mixture is heated at 60±5° C. for 8 hours. After cooling the mixture is concentrated in vacuo and the residue partitioned between water and ethyl acetate. The ethyl acetate phase is isolated, washed with water and dried (MgSO$_4$). The solvent is removed in vacuo to give methyl 5-cyclopentyloxy-6-methylthionicotinoate (920 mg) as a light brown oil. [Elemental analysis: C, 58.41; H, 6.41; N, 5.24%. calculated: C, 58.2; H, 6.44; N, 5.33%.].

Reference Example 29

A solution of potassium hydroxide (582 mg) in water (6 mL) is added to a stirred solution of methyl 5-cyclopentyloxy-6methylthionicotinoate (920 mg) in methanol at room temperature and the mixture stirred for 6 hours. After concentrating in vacuo the mixture is diluted with water and acidified to pH 1 with aqueous 2 M hydrochloric acid. The product is extracted into ethyl acetate, the extracts treated with decolourising charcoal, dried (MgSO$_4$) and evaporated. The residue is triturated with n-pentane to give 5-cyclopentyloxy-6-methylthionicotinic acid (640 mg) as a white solid, m.p. 177-8° C. [Elemental analysis: C, 56.90; H, 6.02; N, 5.52%. calculated: C, 56.90; H, 5.97; N, 5.53%.].

Reference Example 30

A mixture of methyl 5-hydroxy-6-methylthionicotinoate (3 g), isopropyl bromide (2.1 mL) and anhydrous potassium carbonate (3 g) in dry dimethylformamide (35 mL) is stirred and heated at 60±5° C. for 18 hours. After cooling the solvent is removed in vacuo and the residue partitioned between ethyl acetate and water. The organic phase is washed with brine and dried (MgSO$_4$). Evaporation gives a brown oil which is purified by flash chromatography (pentane/ethyl acetate 4:1 v/v as eluent on silica) to give methyl 5-isopropyloxy-6-methylthionicotinoate (2.36 g) as a pale yellow oil. [Elemental analysis: C, 54.40; H, 6.24; N, 5.88%. calculated: C, 54.75; H, 6.27; N, 5.81%.].

Reference Example 31

Potassium hydroxide (770 mg) in water (8 mL) is added to a solution of methyl 5-isopropyloxy-6-methylthionicotinoate (1.1 g) in methanol (15 mL) and the mixture stirred at room temperature for 6 hours. After concentrating in vacuo the residue is dissolved in water and acidified to pH 1 with concentrated aqueous hydrochloric acid. The mixture is extracted with ethyl acetate, the extracts washed with water and dried (MgSO$_4$). The solvent is removed in vacuo to give 5-isopropyloxy-6-methylthionicotinic acid as a white solid, m.p. 154-5° C.

Reference Example 32

Trityl chloride (9.43 g) is added in one portion to a solution of 2-hydroxymethyl-5-methoxy-4-pyridone (5 g) and 4-dimethylaminopyridine (4.2 g) in dry dimethylformamide (80 mL) and the solution stirred at room temperature for 12 hours. The mixture is then heated on a steam bath for 3 hours and diluted with iced water (300 mL) to give a light brown solid. The solid is collected, washed with water and sucked dry. The solid is dissolved in hot ethyl acetate to give a clear solution which immediately deposits a granular off-white solid. The solid does not redissolve on further heating. After cooling the solid is collected, washed with ethyl acetate and diethyl ether and dried to give 5-methoxy-2-trityloxymethyl-4-pyridone (7.5 g) as an off-white solid, m.p. 185-7° C.

Reference Example 33

Diisopropyl azodicarboxylate (1.47 mL) is added to a solution of triphenylphosphine (1.96 g) in dry tetrahydrofuran (20 mL) with cooling to 0-5° C. under a nitrogen atmosphere. The pasty mixture is stirred for a further 30 minutes and then a solution of 5-methoxy-2-trityloxymethyl-4-pyridone (2.0 g) in dry tetrahydrofuran (25 mL) is added followed by the addition of cyclopentanol (0.68 mL). The mixture is stirred at reflux for 8 hours, cooled and the solvent removed in vacuo. The residue is diluted with water and extracted with ethyl acetate. The extracts are dried (MgSO$_4$) and evaporated to give a brown oil. The oil is purified by flash chromatography (n-pentane/ethyl acetate 9:1 v/v as eluent on neutral alumina) to give 4-cyclopentyloxy-5-methoxy-2-trityloxypyridine (1.24 g) as a white solid, m.p. 132-3° C. [Elemental analysis: C, 80.00; H, 6.70; N, 2.70%. calculated: C, 79.97; H, 6.71; N, 3.00%.].

Reference Example 34

90% Formic acid (5.5 mL) is added to a suspension of 4-cyclopentyloxy-5-methoxy-2-trityloxypyridine (1.2 g) in ethyl acetate (8.5 mL) and the mixture stirred at room temperature for 1 hours. The mixture is diluted with ethyl acetate and washed with brine then aqueous sodium bicarbonate until the washings are neutral. The brine washings are neutralised with solid sodium bicarbonate and extracted with ethyl acetate. After drying (MgSO$_4$) the extracts are evaporated to give 4-cyclopentyloxy-2-hydroxymethyl-5-methoxypyridine (360 mg) as a white solid, m.p. 93-94.5° C. [Elemental analysis: C, 64.7; H, 7.80; N, 6.11%. calculated: C, 64.55; H, 7.68; N, 6.27%.].

Reference Example 35

Solid potassium permanganate (5.87 g) is added portionwise during 30 minutes to a suspension of 4-cyclopentyloxy-2-hydroxymethyl-5-methoxypyridine (4.0 g) in water (100 mL) at 50±5° C. When the addition is complete the mixture is heated at 70±5° C. for 45 min and then cooled to room temperature. A solution of potassium hydroxide (1.95 g) in water (50 mL) is added followed by sufficient isopropanol to react with excess potassium permanganate. After stirring for 10 minutes the mixture is filtered through diatomaceous earth and the filtrate concentrated to ~70 mL. The solution is acidified to pH 2 with concentrated aqueous hydrochloric acid and extracted with chloroform. After drying (MgSO$_4$) the extracts are evaporated to give 4-cyclopentyloxy-5-methoxypyridine-2-carboxylic acid (2.5 g) as a white solid, m.p. 184-5° C. [$^1$Hnmr in D$_6$-DMSO shifts relative to Me$_4$Si: 1.55-1.79, 6H, m; 1.95, 2H, m; 3.92, 3H, s; 5.00, 1H, m; 7.59, 1H, s; 8.24, 1H, s.].

Reference Example 36

Hydrogen chloride gas is passed into a suspension of 5-methoxy-4-pyridone-2-carboxylic acid (60.89 g) in methanol (800 mL) with ice bath cooling to 0-5° C. After 2 hours the passage of hydrogen chloride is stopped and then the mixture is refluxed gently for 5 hours. After cooling the solution is allowed to stand overnight. The precipitate is collected, and the filtrate evaporated to dryness. The collected solid and the residue are combined, dissolved in the minimum amount of water and then basified to pH 8 with sodium bicarbonate. The solution is extracted with n-butanol and the extracts evaporated in vacuo to give methyl 5-methoxy-4-pyridone-2-carboxylate (38.3 g) as a pale yellow solid, m.p 185-6° C.

Reference Example 37

Diisopropyl diazodicarboxylate (6.13 mL) is added to a solution of triphenylphosphine (8.16 g), methyl 5-methoxy-4-pyridone-2-carboxylate (3.8 g) and cyclopentanol (2.82 mL) in dry tetrahydrofuran (200 mL) with cooling to 10-15° C. under a nitrogen atmosphere. The mixture is stirred at room temperature for 30 minutes then at reflux for 48 hours. After concentrating, the residue is diluted with water and extracted with ethyl acetate and the extracts washed with water, dried (MgSO$_4$) and evaporated to give a yellow oil. The oil is purified by flash chromatography (pentane/ethyl acetate 3:2 v/v as eluent on silica) to give methyl 4-cyclopentyloxy-5-methoxypyridine-2-carboxylate (4.1 g) as a golden oil.

By proceeding in a similar manner, but replacing cyclopentanol with the appropriate quantity of (±)-tetrahydrothiophen-3-ol, there is prepared: (±)-methyl 5-methoxy-4-(tetrahydrothiophen-3-yloxy)pyridine-2-carboxylate as a solid. [$^1$Hnmr in D$_6$-DMSO shifts relative to Me$_4$Si: 2.04, 1H, m; 2.32, 1H, m; 2.91, 3H, m; 3.20, 1H, dd; 3.85, 3H, s; 3.94, 3H, s; 5.44, 1H m; 7.68, 1H, s; 8.31, 1H, s.].

By proceeding in a similar manner, but replacing cyclopentanol with the appropriate quantity of cyclopropylmethanol, there is prepared:
methyl 4-cyclopropylmethoxy-5-methoxypyridine-2-carboxylate as a white solid, m.p. 93-4° C.

By proceeding in a similar manner, but replacing cyclopentanol with the appropriate quantity of isopropanol, there is prepared:
A 2:1 mixture of ethyl 4-isopropyloxy-5-methoxypyridine-2-carboxylate and methyl 4-isopropyloxy-5-methoxypyridine-2-carboxylate as an oil.

By proceeding in a similar manner, but replacing cyclopentanol with the appropriate quantity of (±)-tricyclo[2.2.1.0.$^{2.6}$]heptan-2-ol, there is prepared:
A 1:1 mixture of (±)-ethyl 5-methoxy-4-(tricyclo[2.2.1.0.$^{2.6}$]hept-2-yloxy)pyridine-2-carboxylate and (±)-methyl 5-methoxy-4-(tricyclo[2.2.1.0.$^{2.6}$]hept-2-yloxy)pyridine-2-carboxylate.

Reference Example 38

A solution of potassium hydroxide (4.71 g) in water (32 mL) is added to a solution of methyl 4-cyclopentyloxy-5-methoxypyridine-2-carboxylate (7.03 g) in methanol (188 mL) and the mixture allowed to stand for 45 hours. After concentrating in vacuo the residue is dissolved in water, washed with ethyl acetate and basified to pH 5 with concentrated aqueous hydrochloric acid. The mixture is extracted with dichloromethane, the extracts dried (MgSO$_4$) and evaporated to give 4-cyclopentyloxy-5-methoxypyridine-2-carboxylic acid (2.4 g) as a white solid.

By proceeding in a similar manner, but replacing methyl 4-cyclopentyloxy-5-methoxypyridine-2-carboxylate with the appropriate quantity of (±)-methyl 5-methoxy-4-(tetrahydrothiophen-3-yloxy)pyridine-2-carboxylate, there is prepared:
(±)-5-methoxy-4-(tetrahydrothiophen-3-yloxy)pyridine-2-carboxylic acid, as a white solid, m.p. 190-1° C. [Elemental analysis: C, 51.3; H, 5.17; N, 5.53%. calculated: C, 57.7; H, 5.13; N, 5.49%.]

By proceeding in a similar manner, but replacing methyl 4-cyclopentyloxy-5-methoxypyridine-2-carboxylate with the appropriate quantity of methyl 4-cyclopropylmethoxy-5-methoxypyridine-2-carboxylate there is prepared:
4-cyclopropylmethoxy-5-methoxypyridine-2-carboxylic acid as a white solid, m.p. 146-7° C. [$^1$Hnmr in D$_6$-DMSO shifts relative to Me$_4$Si: 0.37, 2H, m; 0.60, 2H, m; 1.24, 1H, m; 3.94, 3H, s; 3.98, 2H, d; 7.58, 1H, s; 8.25, 1H, s.].

By proceeding in a similar manner, but replacing methyl 4-cyclopentyloxy-5-methoxypyridine-2-carboxylate with the appropriate quantity of a 2:1 mixture of ethyl 4-isopropyloxy-5-methoxypyridine-2-carboxylate and methyl 4-isopropyloxy-5-methoxypyridine-2-carboxylate, there is prepared:
4-isopropyloxy-5-methoxypyridine-2-carboxylic acid, m.p. 172-3° C. [Elemental analysis: C, 56.77; H, 6.21; N, 6.74%. calculated: C, 56.87; H, 6.20; N, 6.63%.]

By proceeding in a similar manner, but replacing methyl 4-cyclopentyloxy-5-methoxypyridine-2-carboxylate with the appropriate quantity of a 1:1 mixture of (±)-ethyl 5-methoxy-4-(tricyclo[2.2.1.0.$^{2.6}$]hept-2-yloxy)pyridine-2-carboxylate and (±)-methyl 5-methoxy-4-(tricyclo[2.2.1.0.$^{2.6}$]hept-2-yloxy)pyridine-2-carboxylate, there is prepared:
(±)-5-methoxy-4-(tricyclo[2.2.1.0.$^{2.6}$]hept-2-yloxy)pyridine-2-carboxylic acid, as a white solid m.p. 188-9° C. [$^1$Hnmr in D$_6$-DMSO shifts relative to Me$_4$Si: 1.28, 2H, br. d; 1.36, 3H, br. s; 1.59, 1H, d; 1.78, 1H, d; 1.13, 1H, br. s; 2.94, 3H, s; 4.58, 1H, br. s; 7.66, 1H, s; 8.24, 1H, s.].

Reference Example 39

Manganese dioxide (6.0 g) is added to a solution of 4-cyclopentyloxy-2-hydroxymethyl-5-methoxypyridine (2.0 g) in diethyl ether (80 mL) and dichloromethane (10 mL) and the mixture stirred at room temperature for 90 hours. After filtering the filter pad is washed with dichloromethane and the combined filtrate and washings are evaporated to give a white solid. The solid is dried under high vacuum to give 4-cyclopentyloxy-5-methoxypyridine-2-carboxaldehyde (1.65 g). [$^1$Hnmr in D$_6$-DMSO shifts relative to Me$_4$Si: 1.55-1.79, 6H, m; 1.97, 2H, m; 3.96, 3H, s; 5.03, 1H, m; 7.45, 1H, s; 8.41, 1H, s; 9.83, 1H, s.].

Reference Example 40 n-Butyllithium (3.21 mL of 2.5 M solution) is added to a solution of diisopropylamine (1.15 mL) in dry tetrahydrofuran (25 mL) with the temperature being maintained below −60° C. After 30 min a solution of 3,5-dichloro-4-methylpyridine (1.21 g) in tetrahydrofuran (7 mL) is added dropwise and the mixture stirred for a further 30 min. A solution of 4-cyclopentyloxy-5-methoxypyridine-2-carboxaldehyde (1.65 g) in tetrahydrofuran (7 mL) is added and the mixture stirred for 4 hours whilst being allowed to warm to room temperature. After a further 18 hours at room temperature the mixture is diluted with saturated aqueous ammonium chloride (50 mL) and extracted with ethyl acetate. The extracts are washed with water, dried (MgSO$_4$) and evaporated to give a yellow oil. The oil is triturated with n-pentane to give (±)-1-(4-cyclopentyloxy-5-methoxypyridin-2-yl)-2-(3,5-dichloropyridin-4-yl)ethanol (1.4 g) as an off-white solid, m.p. 110-

112° C. [$^1$Hnmr in D$_6$-DMSO shifts relative to Me$_4$Si: 1.55-1.78, 6H, m; 1.95, 2H, m; 3.27, 2H, m; 3.79, 3H, s; 4.89, 2H, m; 5.64, 1H, d; 7.07, 1H, s; 7.98, 1H s; 8.54, 2H, s.].

Reference Example 41

Diisopropyl azodicarboxylate (0.97 mL) is added to a solution of triphenylphosphine (1.29 g) in tetrahydrofuran (10 mL) while cooling to 0-5° C. After stirring for 45 minutes methyl 5-hydroxy-6-methoxynicotinoate (0.9 g) followed by a solution of (±)-endo-(8,9,10-trinorbornan-2-ol) (0.552 g) in tetrahydrofuran (5 mL) are added and the mixture refluxed for 18 hours. Water is added and the mixture is extracted with ethyl acetate, the extracts dried (MgSO$_4$) and evaporated to give a yellow oil. The oil is purified by flash chromatography (n-pentane/ethyl acetate 9:1 v/v on silica) to give methyl (±)-6-methoxy-5-endo-(8,9,10-trinorbornan-2-yloxy)nicotinoate, (1.1 g) as a white solid, m.p. 65-7° C. [Elemental analysis: C, 64.90; H, 7.00; N, 4.95%. calculated: C, 64.97; H, 6.91; N, 5.05%.]

Reference Example 42

Potassium hydroxide (380 mg) in water (5 mL) is added to a solution of methyl (±)-6-methoxy-5-endo-(8,9,10-trinorbornan-2-yloxy)nicotinoate (1.1 g) in methanol (30 mL) and the mixture stirred for 4 hours. After concentrating, the residue is dissolved in water and the solution acidified with concentrated aqueous hydrochloric acid. The product is extracted into ethyl acetate, the extracts dried (MgSO$_4$) and evaporated to give (±)-6-methoxy-5-endo-(8,9,10-trinorbornan-2-yloxy)nicotinic acid (0.95 g) as a white solid, m.p. 192-3° C. [Elemental analysis: C, 63.5; H, 6.36; N, 5.34%. calculated: C, 63.86; H, 6.51; N, 5.32%.]

Reference Example 43

Diisopropyl azodicarboxylate (3.14 mL) is added to a mixture of triphenylphosphine (4.19 g), 5-methoxy-2-trityloxymethyl-4-pyridone (5 g) and (±)-tricyclo[2.2.1.0.$^{2.6}$]heptan-2-ol (1.43 g) in dry toluene (60 mL) at 10-15° C. under a nitrogen atmosphere. The mixture is stirred for 30 minutes then heated at 60±5° C. for 24 hours. After cooling the solvent is evaporated and the residue partitioned between water and ethyl acetate. The ethyl acetate phase is washed with water then brine and dried (MgSO$_4$). Evaporation gives a brown oil which is purified by flash chromatography (n-pentane/ethylacetate 9:1 v/v as eluent on neutral alumina) to give (±)-5-methoxy-4-(tricyclo[2.2.1.0.$^{2.6}$]hept-2-yloxy)-2-trityloxymethylpyridine, (2.74 g), as a white solid, m.p. 140-2° C. [Elemental analysis: C, 80.70; H, 6.41; N, 2.54%. calculated: C, 80.95; H, 6.38; N, 2.86%.]

Reference Example 44

A solution of (±)-5-methoxy-4-(tricyclo[2.2.1.0.$^{2.6}$]hept-2-yloxy)-2-trityloxymethylpyridine (17 g) in glacial acetic acid is stirred at 65±5° C. for 24 hours. After cooling the solvent is removed in vacuo, the residue treated with water and the resulting mixture extracted with ethyl acetate. The ethyl acetate extracts are washed with 1 M aqueous hydrochloric acid, the aqueous washings basified to pH 8 with 6 M aqueous sodium hydroxide and extracted with ethyl acetate. These extracts are dried (MgSO$_4$) and evaporated to give (±)-2-hydroxymethyl-5-methoxy-4-(tricyclo[2.2.1.0.$^{2.6}$]hept-2-yloxy)pyridine as a colourless oil.

Reference Example 45

Sodium hydroxide (1.1 g) is added to a suspension of (±)-2-hydroxymethyl-5-methoxy-4-(tricyclo[2.2.1.0.$^{2.6}$]hept-2-yloxy)pyridine (4.54 g) in water (70 mL). Activated manganese dioxide (9 g) is added portionwise during 45 minutes and the resulting mixture heated at 65±5° C. for 6 hours. The mixture is filtered hot through diatomaceous earth and the filtrate concentrated to low volume in vacuo. The mixture is acidified with glacial acetic acid and extracted with dichloromethane. The extracts are dried (MgSO$_4$) and evaporated. The residue is purified by flash chromatography (ethyl acetate/methanol 19:1 v/v as eluent on silica) to give (±)-5-methoxy-4-(tricyclo[2.2.1.0.$^{2.6}$]hept-2-yloxy)pyridine-2-carboxylic acid as a solid, m.p. 182-3° C.

Reference Example 46

A mixture of (±)-5-methoxy-4-(tricyclo[2.2.1.0.$^{2.6}$]hept-2-yloxy)pyridine-2-carboxylic acid (4.3 g) and concentrated hydrochloric acid (5 mL) in methanol (50 mL) is refluxed for 8 hours. After cooling the mixture is concentrated to a low volume, diluted with water and neutralised with solid sodium bicarbonate. The mixture is filtered and extracted with dichloromethane. The combined extracts are washed with saline, dried (MgSO$_4$) and evaporated to give (±)-methyl 5-methoxy-4-(tricyclo[2.2.1.0.$^{2.6}$]hept-2-yloxy)pyridine-2-carboxylate (2.3 g). [$^1$Hnmr in D$_6$-DMSO shifts relative to Me$_4$Si: 1.29, 2H, m; 1.47, 3H, m; 1.60, 1H, d; 1.78, 1H, d; 2.14, 1H, br. s; 3.84, 3H, s; 3.94, 3H, s; 4.59, 1H, br. s; 7.67, 1H, s; 8.28, 1H, s.]

Reference Example 47

4-Dimethylaminopyridine (17.55 g) and trityl chloride (40.5 g) are added to a solution of 5-benzyloxy-2-hydroxymethyl-4-pyridone (30.2 g) in dry dimethylformamide and the mixture stirred and heated at 95° C. for 2 hours. After cooling the mixture is poured into iced-water (800 mL) and the precipitate collected, washed with water (2×500 mL) and sucked dry. The solid is boiled with methanol (500 mL) and after cooling the solid is collected, washed with methanol (200 mL) and diethyl ether (2×100 mL) and dried at 80° C. to give 5-benzyloxy-2-trityloxymethyl-4-pyridone (26.5 g) as a white solid, m.p. 233-5° C.

Reference Example 48

Diisopropyl azodicarboxylate (13.5 mL) is added to a mixture of triphenylphosphine (18.15 g), 5-benzyloxy-2-trityloxymethyl-4-pyridone (21.1 g) and cyclopentanol (6.25 mL) in dry tetrahydrofuran (600 mL) at 10-15° C. under a nitrogen atmosphere. The mixture is stirred for 30 minutes then heated at reflux for 24 hours. After cooling the solvent is evaporated to give a brown oil which is purified by flash chromatography (n-pentane/ethyl acetate 4:1 v/v as eluent on silica) to give 5-benzyloxy-4-cyclopentyloxy-2-trityloxymethylpyridine as a colourless oil.

Reference Example 49

5% Palladium on charcoal catalyst (2 g) is added to a solution of 5-benzyloxy-4-cyclopentyloxy-2-trityloxmethylpyridine (24.2 g) in ethanol (500 mL) and the mixture stirred at room temperature under a hydrogen atmosphere for 3 hours. After filtering the filtrate is concentrated in vacuo to give a colourless oil which is purified by flash chromatography (n-pentane/ethyl acetate 7:3 v/v as eluent on silica) to give 4-cyclopentyloxy-5-hydroxy-2-trityloxymethylpyridine (18.8 g) as a colourless foam. [$^1$Hnmr in deuterochloroform with Me$_4$Si as standard: 1.70, 2H, m; 1.82, 2H, m; 1.90-2.08, 4H, m; 4.25, 2H, s; 4.93, 1H, m; 7.19, 1H, s; 7.24, 7.30, 7.49, 15H, Ar; 8.04, 1H, s.].

Reference Example 50

Chlorodifluoromethane is bubbled through a suspension of potassium carbonate (2.13 g) and potassium iodide (584 mg) in a solution of 4-cyclopentyloxy-5-hydroxy-2-trityloxymethylpyridine (5 g) in dimethylformamide (40 mL) while heating at 70±5° C. and using a cardice/acetone condenser to recycle the condensate. After 4 hours the addition of chlorodifluoromethane is stopped and the mixture heated for a further 16 hours. After cooling the mixture is concentrated in vacuo, the residue diluted with water, acidified to pH 4 with glacial acetic acid and extracted with dichloromethane. The extracts are dried (MgSO$_4$) and evaporated. The residue is purified by flash chromatography (gradient elution using n-pentane/ethyl acetate 9:1 v/v to 7:3 v/v on silica) to give 4-cyclopentyloxy-5-difluoromethoxy-2-trityloxymethylpyridine (240 mg) as an oil. [$^1$Hnmr in deuterochloroform with Me$_4$Si as standard: 1.72, 2H, m; 1.85, 2H, m; 2.00, 4H, m; 4.31, 2H, s; 4.95, 1H, m; 6.51, 1H, t, J=74 Hz; 7.22-7.55, 16H, m; 8.19, 1H, s.].

Reference Example 51

A mixture of 5,6-dimethoxy-3-methylpyridazine-2-oxide (0.5 g) in acetic anhydride (2 mL) is refluxed for 2 hours. After cooling the mixture is diluted with water and extracted with ethyl acetate (2×20 mL): The extracts are dried (MgSO$_4$) and evaporated to give a brown oil which is purified by flash chromatography (ethyl acetate as eluent on silica) to give 6-acetoxymethyl-3,4-dimethoxypyridazine (0.27 g) as a colourless oil.

Reference Example 52

A solution of potassium carbonate (0.2 g) in water 2 mL) is added to a solution of 6-acetoxymethyl-3,4-dimethoxypyridazine (0.27 g) in methanol (6 mL) and the mixture stirred at 60-70° C. for 2 hours. After evaporating to dryness the residue is partitioned between ethyl acetate (10 mL) and brine (10 mL). The ethyl acetate phase is evaporated to dryness and the residue purified by flash chromatography (ethyl acetate as eluent on silica) to give 3,4-dimethoxy-6-hydroxymethylpyridazine as a white solid, m.p. 151-3° C.

Reference Example 53

A solution of oxalyl chloride (0.61 mL) in dichloromethane (11 mL) is cooled to −60° C. and dimethylsulphoxide (0.98 g) is added dropwise maintaining the reaction mixture at −60° C. After 15 minutes a solution of 3,4-dimethoxy-6-hydroxymethylpyridazine (1.0 g) in dichloromethane (42 mL) is added dropwise during 45 minutes maintaining the reaction mixture at −60° C. After a further 15 minutes triethylamine (3.96 mL) is added, the mixture stirred at −60° C. for 15 minutes then cooling is discontinued. When the reaction mixture attains room temperature stirring is continued for 1 hour. The reaction mixture is diluted with water (100 mL) and dichloromethane (100 mL) and the organic phase separated. The aqueous phase is re-extracted with dichloromethane (100 mL) and the combined extracts are dried (MgSO$_4$). Evaporation gave 5,6-dimethoxypyridazine-3-carboxaldehyde (0.95 g) as a white solid, m.p. 179-81° C.

Reference Example 54 n-Butyllithium (1.51 mL of a 1.6 M solution in hexane) is added to a solution of diisopropylamine (0.34 mL) in tetrahydrofuran (29 mL) at −10° C. under a nitrogen atmosphere. After 30 minutes the mixture is cooled to −70° C. and a solution of 3,5-dichloro-4-methylpyridine (0.39 g) in tetrahydrofuran (4 mL) is added dropwise. After 30 minutes a solution of 5,6-dimethoxy-pyridazine-3-carboxaldehyde (0.35 g) in tetrahydrofuran (15 mL) is added at −70 to −60° C. and stirring continued at this temperature for 1 hour before cooling is discontinued. After 24 hours the yellow solution is quenched by the addition of aqueous ammonium chloride and the mixture extracted with ethyl acetate. The dried extracts (MgSO$_4$) are evaporated and the residue purified by flash chromatography (ethyl acetate as eluent on silica) to give (±)-2-(3,5-dimethylpyrid-4-yl)-1-(5,6-dimethoxypyridazin-3-yl)ethanol (0.17 g), as a white solid, m.p. 217-8° C.

Reference Example 55

Water (4 drops is added to a solution of 4-cyclopentyloxy-5-difluoromethoxy-2-trityloxypyridine (900 mg) in glacial acetic acid (20 mL) and the mixture heated at 60° C. for 18 hours. After cooling the mixture is evaporated to dryness and the residue partitioned between water and ethyl acetate. The organic phase is dried over magnesium sulphate and evaporated to give a pale yellow solid which is purified by flash chromatography (gradient elution using n-pentane/ethyl acetate 7:3 v/v to n-pentane/ethyl acetate 2:3 v/v on silica) to give 4-cyclopentyloxy-5-difluoromethoxy-2-hydroxymethylpyridine (250 mg) as a white solid, m.p. 85-6° C.

Reference Example 56

Solid potassium permanganate (306 mg) is added portionwise to a stirred suspension of 4-cyclopentyloxy-5-difluoromethoxy-2-hydroxymethylpyridine (250 mg) in water (10 mL) while heating at 50±5° C. The resulting mixture is heated for 1.5 hours at this temperature, then at 70° C. for minutes. A solution of potassium hydroxide (150 mg) in water (1 mL) is added followed by the addition of isopropanol until the excess potassium permanganate is consumed. After 15 minutes, the mixture is cooled and filtered through a pad of diatomaceous earth and the filtrate adjusted to pH 5 with glacial acetic acid. The white precipitate is collected, washed with water and dried in vacuo to give 4-cyclopentyloxy-5-difluoromethoxypyridine-2-carboxylic acid (240 mg) as a white solid, m.p. 215-6° C. decomp. [Elemental analysis: C, 52.57; H, 4.67; N, 5.18%, calculated: 52.75; H, 4.80; N, 5.13%].

The compounds of formula I exhibit useful pharmacological activity and accordingly are incorporated into pharmaceutical compositions and used in the treatment of patients suffering from certain medical disorders. More especially, they are cyclic AMP phosphodiesterase inhibitors, in particular type IV cyclic AMP phosphodiesterase inhibitors. The present invention provides compounds of formula I, and compositions containing compounds of formula I, which are of use in a method for the treatment of a patient suffering from, or subject to, conditions which can be ameliorated by the administration of an inhibitor of cyclic AMP phosphodiesterase. For example, compounds within the present invention are useful as bronchodilators and asthma-prophylactic agents and agents for the inhibition of eosinophil accumulation and of the function of eosinophils, such as for the treatment of inflammatory airways disease, especially reversible airway obstruction or asthma, and for the treatment of other diseases and conditions characterized by, or having an etiology involving, morbid eosinophil accumulation. As further examples of conditions which can be ameliorated by the administration of inhibitors of cyclic AMP phosphodiesterase such as compounds of formula I there may be mentioned inflammatory diseases, such as atopic dermatitis, urticaria, allergic rhinitis, psoriasis, rheumatic arthritis, ulcerative colitis, Crohn's disease, adult respiratory distress syndrome and diabetes insipidus, other proliferative skin diseases such as keratosis and various types of dermatitis, conditions associated with cerebral metabolic inhibition, such as cerebral senility, multi-infarct dementia, senile dementia (Alzheimer's disease), and memory impairment associated with Parkinson's disease, and conditions ameliorated by neuroprotectant activity, such as cardiac arrest, stroke, and intermittent claudication. A special embodiment of the therapeutic methods of the present invention is the treating of asthma.

The compounds are also inhibitors of tumor necrosis factor, especially a-TNF. Thus, the present invention provides compounds of formula I, and compositions containing compounds of formula I, which are of use in a method for treating a patient suffering from, or subject to, conditions which can be ameliorated by the administration of an inhibitor of a-TNF. For example compounds of the present invention are useful in joint inflammation, arthritis, rheumatoid arthritis and other arthritic conditions such as rheumatoid spondylitis and osteoarthritis. Additionally, the compounds are useful in treatment of sepsis, septic shock, gram negative sepsis, toxic shock syndrome, acute respiratory distress syndrome, asthma and other chronic pulmonary diseases, bone resorption diseases, reperfusion injury, graft vs. host reaction and allograft rejection. Furthermore, the compounds are useful in the treatment of infections such as viral infections and parasitic infections, for example malaria such as cerebral malaria, fever and myalgias due to infection, HIV, AIDS, cachexia such as cachexia secondary to AIDS or to cancer. Other disease states that may be treated with the compounds of the present invention include Crohn's disease, ulcerative colitis, pyresis, systemic lupus erythematosus, multiple sclerosis, type I diabetes mellitus, psoriasis, Bechet's disease, anaphylactoid purpura nephritis, chronic glomerulonephritis, inflammatory bowel disease and leukemia. A special embodiment of the therapeutic methods of the present invention is the treating of joint inflammation.

According to a further feature of the invention there is provided a method for the treatment of a human or animal patient suffering from, or subject to, conditions which can be ameliorated by the administration of an inhibitor of cyclic AMP phosphodiesterase or of TNF, especially a-TNF, for example conditions as hereinbefore described, which comprises the administration to the patient of an effective amount of compound of formula I or a composition containing a compound of formula I. "Effective amount" is meant to describe an amount of compound of the present invention effective in inhibiting cyclic AMP phosphodiesterase and/or TNF and thus producing the desired therapeutic effect.

The present invention also includes within its scope pharmaceutical formulations which comprise at least one of the compounds of formula I in association with a pharmaceutically acceptable carrier or coating.

In practice compounds of the present invention may generally be administered parenterally, rectally or orally, but they are preferably administered by inhalation.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

Compounds within the scope of the present invention exhibit marked pharmacological activities according to tests described in the literature which tests results are believed to correlate to pharmacological activity in humans and other mammals. The following pharmacological test results are typical characteristics of compounds of the present invention.

1. Inhibitory Effects of Compounds on PDE Activity.
1.1 Preparation of PDE Isozymes from Pig Aorta.

The method is described fully by Souness and Scott (*Biochem. J.*, 291, 389-395, 1993). Briefly, aortas of freshly slaughtered pigs are placed in Hepes buffered krebs solution, extraneous tissue on the outside of the aorta is trimmed off and the endothelial layer on the intimal surface is removed by rubbing with a cotton swab. Smooth muscle strips are plucked from the aorta and 25 g are homogenized using a Waring Blender in homogenization buffer (20 mM Tris/HCl, pH 7.5, 2 mM $MgCl_2$, 1 mM dithiothreitol, 5 mM EDTA and 1 mg/ml aprotinin). The homogenate is further homogenized with an Ultra-Turrax and then centrifuged (3000 g, 5 minutes). The supernatant is removed, and the pellet is sonicated in a small volume (25-50 mL) of homogenization buffer. The sonicate is centrifuged (3000 g, 5 minutes), the pellet discarded and the supernatant is pooled with that from the first centrifugation step. The pooled supernatants are centrifuged (100,000 g, 1 hour), the resulting high-speed supernatant is filtered (0.45 µm) and then applied to a DEAE-trisacryl (IBF) column (50×2.44 cm) preequilibrated in column buffer (20 mM Tris/HCl, pH 7.5, 2 mM $MgCl_2$, 1 mM dithiothreitol, 20 µM TLCK). The column is washed with 500-700 mL of column buffer and PDE activities are eluted with 2 successive linear gradients of NaCl (0-200 mM, 400 mL and 200-300 mM, 200 mL) in column buffer. The fractions in the separated peaks of activity corresponding to the different PDE isozymes are pooled and stored at −20° C. in 30% (v/v) ethylene glycol.

1.2 Measurement of PDE Activity.

PDE activity is determined by the two-step radioisotopic method of Thompson et al., *Adv. Cyclic Nucl. Res.*, 10, 69-92 (1979). The reaction mixture contains 20 mM Tris/HCl (pH 8.0), 10 mM $MgCl_2$, 4 mM 2-mercaptoethanol, 0.2 mM EGTA and 0.05 mg of BSA/mL. The concentration of substrate is 1 µM.

The $IC_{50}$ values for the compounds examined are determined from concentration-response curves in which concentrations range from 0.1 nM- to 40 µM.

1.3 Results.

Compounds within the scope of the invention produce up to about 50% inhibition of porcine aortic cyclic AMP-specific phosphodiesterase (PDE IV) at concentrations from about $10^{-9}$ M up to about $10^{-5}$ M, preferably from about $10^{-9}$ up to about $10^{-8}$ M. The compounds of the invention are from about 10,000-fold to about 50-fold more selective for cyclic AMP phosphodiesterase IV than cyclic nucleotide phosphodiesterase types I, III or V.

2. Inhibitory Effects of Compounds on Eosinophil Superoxide Generation.
2.1 Preparation of Guinea-Pig Eosinophils.

The method is described fully in Souness et al (*Biochem. Pharmacol.* 42, 937-945, 1991).

2.2 Measurement of Superoxide Generation.

Superoxide anion generation is determined as the superoxide dismutase inhibitable reduction of p-iodonitrotetrazolium violet (INTV) (Souness et al, *Biochem. Pharmacol.* 42, 937-945, 1991). Briefly, cells are incubated in 96 well microtitre plates in 0.25 mL of Hanks buffered salt solution (HBSS) containing INTV (0.5 mg/mL) plus other additions for 45 minutes at 37° C. The cells are then centrifuged at 500 g for 5 minutes and the supernatant is aspirated. The pellet is solubilized by incubation overnight at room temperature in DMSO containing 0.6 M HCl and the absorbance of the reduced dye is measured at 492 nm. The results are expressed in absorbance units.

2.3 Results.

Compounds within the scope of the invention produce up to about 50% inhibition of superoxide generation from eosinophils harvested from the peritoneal cavities of guinea-pigs at concentrations from about $10^{-8}$ M to about $10^{-8}$ M, preferably from about $10^{-8}$ M up to about $10^{-7}$ M.

3. Effects of Compounds on Tracheal Smooth Muscle Contractility.
3.1 Preparation of Guinea-Pig Tracheal Strips and Contractility Studies.

Organ bath studies are performed essentially according to Tomkinson et al (*Br. J. Pharmacol.* 108 57-61, 1993). Briefly, tracheas are removed from male, Dunkin-Hartley guinea-pigs (400-500 g) are placed in Krebs Ringer Bicarbonate (KRB) solution and fat and connective tissue are dissected away. Epithelium is removed by mechanical abrasion and the tracheal strips are suspended under an applied load, such that they are at their optimal length, derived from preliminary experiments, and equilibrated for 90 minutes, washing at 15 minute intervals.

Cumulative concentration-response curves to spasmogens are constructed and the concentration producing 30% of maximum contraction ($EC_{30}$) is determined by computerized linear regression analysis. For relaxant studies, tissues are contracted with spasmogens (such as methacholine, histamine, leukotriene $D_4$) ($EC_{30}$) and when the response plateaus, PDE inhibitors (10 nM-100 µM) or vehicle control (DMSO) are added cumulatively. The concentration of relaxant producing 50% inhibition ($IC_{50}$) of the agonist response is calculated by linear regression. Alternatively, PDE inhibitors, as above, may be added to tissues under basal tone and the concentration producing 50% relaxation ($EC_{50}$) calculated as above.

3.2 Results.

Compounds within the scope of the invention produce about 50% relaxation of guinea-pig tracheal strips (under basal tone or which had been contracted by treatment with spasmogens) at concentrations from about $5 \times 10^{-9}$ M to about $10^{-5}$ M, preferably from about $5 \times 10^{-9}$ M to about $10^{-7}$ M.

4. In Vivo Bronchodilator Actions of Compounds.
4.1 Measurement of Bronchodilatation.

Bronchorelaxant activity is measured in in vivo tests in the anaesthetized guinea-pig or rat according to the method described in Underwood et al., *Pulm. Pharmacol.* 5, 203-212, (1992) in which the effects on bronchospasm induced by histamine (or other spasmogens such as methacholine or leukotriene $D_4$) is determined. Nebulized aerosols generated from aqueous solutions of compounds of the invention are each administered for one minute to the anaesthetized animals. Alternatively, dry powder formulations made up from compounds of the invention and lactose are blown into the airways of the anaesthetized guinea-pigs or rats by the method described in Underwood et al., *J. Pharm. Methods*, 26, 203-210, 1991.

4.2 Results.

Compounds within the scope of the invention produce from about 30% up to about 90% decrease in bronchospasm when administered at effective doses of about 4 to about 1000 μg/kg, preferably about 4 to about 50 μg/kg, without any significant effect on blood pressure.

5. In Vivo Actions of Compounds on Antigen (Ovalbamin)-Induced Eosinophilia in Guinea-Pigs.

5.1 Treatment of Animals and Measurement of Eosinophil Numbers.

Male Dunkin-Hartley guinea-pigs weighing 200-250 g are sensitized using 10 μg ovalbumin in 1 mL of a 100 mg/mL suspension of aluminium hydroxide, i.p.

Sensitized guinea-pigs are anaesthetised and dry powder formulations of PDE inhibitors or lactose are administered (i.t.) into the airways. In some cases PDE inhibitors are administered orally. 23 hours later the procedure is repeated and 60 minutes later the guinea-pigs are challenged with nebulized saline or ovalbumin (1% in saline) for 15 seconds. 24 hours after challenge the guinea-pigs are killed and the lungs are lavaged with warm saline. Total and differential cell counts are made.

5.2 Results.

Compounds within the scope of the invention, administered one hour before challenge, inhibit by at least 50% ovalbumin-induced eosinophilia in guinea-pigs which is measured 24 hours after challenge, at oral doses of about 1 to about 50 mg/kg, preferably about 1 to 10 mg/kg and inhaled doses of about 4 to 1000 μg/kg, preferably. 4 to 50 μg/kg.

6 In Vitro Inhibitory Effects on TNF-Alpha Release by Human Monocytes.

The effects of compounds on TNF-alpha production by human peripheral blood monocytes (PBMs) are examined as follows:

6.1. Preparation of Blood Leukocytes.

Blood is drawn from normal donors, mixed with dextran, and the erythrocytes allowed to sediment for 35 minutes at 37° C. Leukocytes are fractionated by centrifugation through a discontinuous (18, 20 and 22%) metrizamide gradient. The mononuclear cell fraction comprising 30-40% PBMs is suspended in HBSS and stored at 4° C. until use.

6.2. Measurement of TNF-Alpha.

Cells from the PBM-rich metrizamide fraction are spun down (200 g for 10 minutes at 20° C.), resuspended at $10^6$ PBMs/mL of medium; RPMI 1640 containing 1% v/v FCS, 50 U/mL penicillin and 50 mg/mL streptomycin (Gibco, U.K.), then plated out in 96 well plates at $2\times10^5$ cells/well. The medium (200 μL) is changed to remove any non-adherent cells and the remaining, adherent PBMs left in the incubator overnight (18 hours). One hour prior to challenge, the medium is changed to that containing compound for test or drug vehicle. Control treatments and compounds for test are assayed in quadruplicate wells. Compounds are tested within the concentration range of $3\times10^{-10}$ M to $3\times10^{-6}$ M. Medium (50 μL) with or without 10 ng/ml LPS (*E. Coli*, 055 B5 from Sigma, U.K.) is then added. The incubation is then continued for a further 4 hours. Cell supernatants are removed for storage at −20° C.

TNFa levels in cell supernatants are quantified using a standard sandwich ELISA technique. ELISA plates (Costar, U.K.) are coated overnight at 4° C. with 3 mg/mL polyclonal goat anti-human TNF-alpha antibody (British Biotechnology, U.K.) in pH 9.9 bicarbonate buffer. Rabbit polyclonal anti-human TNF-alpha antiserum (Janssen Biochimicha, Belgium) at 1/500 dilution is used as the second antibody and polyclonal goat anti-rabbit IgG horseradish peroxidase (Calbiochem, U.S.A.) at 1/8000 dilution is used as the detection antibody. Color development is measured by absorbance at 450 nm using a Titek plate reader.

TNF-alpha levels are calculated by interpolation from a standard curve using recombinant human TNF-alpha (British Biotechnology U.K.) (0.125-8 ng/mL). Data (log-conc. vs. log-resp) are fitted by linear regression (p>0.99) using a Multicalc (Wallac Pharmacia, U.K.) software program. Basal TNF-alpha levels are less than 100 pg/mL whilst LPS stimulation of the PBMs increases TNF-alpha levels to 3-10 ng/mL.

6.3 Results.

Compounds within the scope of the invention produce 50% inhibition of LPS-induced TNF-alpha release from human PBMs at concentrations within the range of about $10^{-9}$ M to about $10^{-6}$ M., preferably about $10^{-9}$ M to about $10^{-8}$ M.

7. Inhibitory Effects of Compounds on Antigen-Induced Bronchoconstriction in the Conscious Guinea-Pig.

7.1. Sensitisation of Guinea-Pigs and Measurement of Antigen—Induced Bronchoconstriction.

Male, Dunkin-Hartley guinea-pigs (550-700 g) are sensitized as above. Specific airways resistance (SRaw) is measured in conscious animals by whole body plethysmography using a variation of the method of Pennock et al., (*J. Appl. Physiol.*, 46, 399, 1979). Test compounds or vehicle (lactose carrier) are instilled into the airways as dry powders through a metal gavage needle. 30 minutes later, the animals are injected with mepyramine (30 mg/kg i.p.) to prevent anaphylactic collapse and placed into the plethysmography chambers where SRaw is determined at 1 minute intervals. Resting SRaw is then determined. Animals are challenged with an aerosol of ovalbumin and SRaw is determined every 5 minutes for 15 minutes.

7.2. Results.

Compounds within the scope of the invention inhibit antigen-induced bronchoconstriction by up to 80% at doses of between about 1 to about 1000 μg/kg (i.t.), preferably about 1 to about 20 μg/kg (i.t.).

8. Inhibitory Effects of Compounds on Serum TNF-Alpha Levels in LPS—Challenged Mice.

8.1. Treatment of Animals and Measurement of Murine TNF-Alpha.

Female Balb/c mice (age 6-8 weeks, weight 20-22 g from Charles River, U.K.) in groups of five or more animals are dosed p.o. with compounds suspended in 1.5% (w/v) carboxymethyl cellulose then challenged after a minimum period of 30 min with 30 mg of LPS i.p. After 90 min the animals are killed by $CO_2$ asphyxiation and bled by cardiac puncture. Blood is allowed to clot at 4° C., centrifuged (12,000 g for 5 minutes) and serum taken for TNF-alpha analysis.

TNF-alpha levels are measured using a commercially available murine TNF-alpha ELISA kit, purchased from Genzyme (Cat. no. 1509.00), as recommended by the manufacturer. Values for TNF-alpha are calculated from a recombinant murine TNF-alpha standard curve.

8.2 Results.

Compounds within the scope of the invention inhibit LPS-induced serum TNF-alpha at doses between about 10 and about 10,000 mg/kg, preferably about 10 to about 250 μg/kg.

The value of the compounds of the invention is enhanced by their very low mammalian toxicity levels.

The following Composition Examples illustrate pharmaceutical compositions according to the present invention.

Composition Example 1

N-(3,5-dichloropyrid-4-yl)-3-cyclopentyloxy-6-fluoro-4methoxy-benzamide (1.0 g) (mean particle size 3.5 microns) and lactose (99 g) (mean particle size 72 microns) are blended together for 30 minutes in a mechanical shaker/mixer. The resulting blend is filled, to a fill weight of 25 mg, into No. 3 hard gelatine capsules, to give a product suitable for use, for example, with a dry powder inhaler.

Composition Example 2

| No. 2 size gelatin capsules each containing:- | |
| --- | --- |
| N-(3,5-dichloropyrid-4-yl)-3-cyclopentyloxy-6-fluoro-4methoxybenzamide | 20 mg |
| lactose | 100 mg |
| starch | 60 mg |
| dextrin | 40 mg |
| magnesium stearate | 1 mg |
| are prepared in accordance with the usual procedure. | |

Composition Example 3

5-Cyclopentyloxy-N-(3,5-dichloropyrid-4-yl)-6-methoxynicotinamide (1.0 g) (mean particle size 3.5 microns) and lactose (99 g) (mean particle size 72 microns) are blended together for 30 minutes in a mechanical shaker/mixer. The resulting blend is filled, to a fill weight of 25 mg, into No. 3 hard gelatine capsules, to give a product suitable for use, for example, with a dry powder inhaler.

Composition Example 4

| No. 2 size gelatin capsules each containing:- | |
| --- | --- |
| 5-cyclopentyloxy-N-(3,5-dichloro-pyrid-4-yl)-6-methoxynicotinamide | 20 mg |
| lactose | 100 mg |
| starch | 60 mg |
| dextrin | 40 mg |
| magnesium stearate | 1 mg |
| are prepared in accordance with the usual procedure. | |

Compositions similar to those above are prepared from other compounds of formula I.

What is claimed is:

1. A compound of formula I

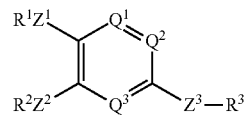

wherein
R$^1$ is lower alkyl optionally substituted by one or more of halo, cycloalkyl or cycloalkenyl;
R$^2$ is alkyl, alkenyl or alkynyl each optionally substituted by one or more of halo, cycloalkyl or cycloalkenyl; or cycloalkyl or cycloalkenyl each optionally substituted by one or more of halo, methylidene or alkyl; or optionally substituted cyclothioalkyl consisting of a non-aromatic monocyclic or multicyclic ring system of 3 to about 10 ring atoms wherein at least one of the ring atoms is sulphur and the other ring atoms are carbon and the substituted cyclothioalkyl is substituted by one or more halo, or any ring sulphur atom is optionally oxidised to the corresponding S-oxide or S,S-dioxide; or optionally substituted cyclothioalkenyl consisting of a non-aromatic monocyclic or multicyclic ring system of 3 to about 10 ring atoms wherein at least one of the ring atoms is sulphur, the other ring atoms are carbon and the ring system contains a carbon-carbon double bond and the substituted cyclothioalkenyl is substituted by one or more halo or any ring sulphur atoms is optionally oxidised to the corresponding S-oxide or S,S-dioxide;
R$^3$ is optionally substituted aryl or heteroaryl, wherein the substituted aryl or substituted heteroaryl group is substituted by one or more substituents which may be the same or different and are selected from alkyl, aryl, aralkyl, hydroxy, hydroxyalkyl, alkoxy, aryloxy, aralkyloxy, carboxy, acyl, aroyl, halo, nitro, cyano, carboxy, alkoxycarboxyl, aryloxycarbonyl, aralkyloxycarbonyl, acylamino, aroylamino, alkylsulfonyl, arylsulfonyl, alkylsulfinyl, arylsulfinyl, alkylthio, arylthio, aralkylthio, Y$^1$Y$^2$N—, Y$^1$Y$^2$NCO— or Y$^1$Y$^2$NSO$_2$—, where Y$^1$ and Y$^2$ are independently hydrogen, alkyl, aryl, and aralkyl;
one of Q$^1$, Q$^2$ and Q$^3$ is nitrogen and the others of Q$^1$, Q$^2$ and Q$^3$ are independently CX or CH;
Z$^1$ and Z$^2$ are independently oxygen or sulfur;
Z$^3$ is —CSCH$_2$—, —CS—CS—, —CH$_2$—S—, or —CH$_2$—SO$_2$—, —CSNH$_2$; and
X is halo;
or N-oxide thereof or a pharmaceutically acceptable salt thereof; with the proviso that R$^1$Z$^1$ and R$^2$Z$^2$ cannot both represent methoxy.

2. The compound according to claim 1 wherein
R$^2$ is alkyl optionally substituted by one or more halo, cycloalkyl or cycloalkenyl; cycloalkyl or cycloalkenyl each optionally substituted by one or more of halo, methylidene or alkyl; or optionally substituted cyclothioalkyl consisting of a non-aromatic monocyclic or multicyclic ring system of 3 to about 10 ring atoms wherein at least one of the ring atoms is sulphur and the other ring atoms are carbon and the substituted cyclothioalkyl is substituted by one or more halo, or any ring sulphur atom is optionally oxidised to the corresponding S-oxide or S,S-dioxide;

$R^3$ is phenyl, substituted phenyl or azaheteroaryl;
one of $Q^1$ and $Q^2$ is nitrogen and the other is CX or CH
$Q^3$ is CH; and
$Z^3$ is —CSCH$_2$ or CSNH—.

3. The compound according to claim 2 wherein
$R^1$ is methyl or difluoromethyl;
$R^2$ is isopropyl, cyclopropylmethyl, cyclopentyl, trinorbornyl, trinorbornenyl, tricyclo[2.2.1.0$^{2.6}$]heptanyl and tetrahydrothiophenyl;
$Z^1$ is oxygen or sulphur;
$Z^2$ is oxygen; and
$Z^3$ is —CSCH$_2$ or —CSNH—.

4. The compound according to claim 1 wherein one of $Q^1$ and $Q^2$ is nitrogen, and the other is CX or CH.

5. The compound according to claim 4 wherein CX is CF.

6. The compound according to claim 1 wherein $Q^1$ is N, and $Q^2$ and $Q^3$ are CH; $Q^2$ is N, and $Q^1$ and $Q^3$ are CH; or $Q^1$ or $Q^2$ are N, is $Q^3$ is CH.

7. The compound according to claim 6 wherein CX is CF.

8. The compound according to claim 1 wherein $Q^2$ is nitrogen or CF.

9. The compound according to claim 1 wherein independently one of $Q^1$, $Q^2$ or $Q^3$ is N-oxide or $R^3$ is azaheterocyclyl having an imine moiety thereof as an N-oxide.

10. The compound according to claim 1 wherein $Q^1$ and $Q^3$ are CH, and $Q^2$ is an N-oxide.

11. The compound according to claim 1 wherein $R^3$ is phenyl substituted on the 2-position or on both the 2- and 6-positions.

12. The compound according to claim 1 wherein $R^3$ is heteroaryl substituted on one or both of the positions adjacent to the position of $R^3$ that is attached to $Z^3$.

13. The compound according to claim 1 wherein $R^3$ is azaheteroaryl substituted on one or both, more preferably on both, of the positions adjacent to a position of $R^3$ that is attached to $Z^3$.

14. The compound according to claim 13 wherein $R^3$ is a 3,5-dihalo-pyrid-4-yl.

15. The compound according to claim 14 wherein $R^3$ is 3,5-dihalo-1-oxido-4-pyridinium.

16. The compound according to claim 1 wherein $Z^2$ is —CZNH— or —CZCH$_2$—.

17. The compound according to claim 16 wherein Z is oxygen.

18. The compound according to claim 1 wherein $Z^1$ and $Z^2$ are oxygen, or $Z^1$ is sulfur and $Z^2$ is oxygen.

19. The compound according to claim 18 wherein $Z^1$ and $Z^2$ are oxygen.

20. The compound according to claim 1 wherein $Z^1$ is oxygen.

21. The compound according to claim 1 wherein $R^1$ is lower alkyl optionally substituted by one or more halo.

22. The compound according to claim 21 wherein the substitution is on a position of $R^1$ that is attached to $Z^1$.

23. The compound according to claim 1 wherein $R^2$ is lower alkyl, cycloalkyl or cyclothioalkyl optionally substituted by one or more halo.

24. The compound according to claim 23 wherein the substitution is on a position of $R^2$ that is attached to $Z^1$.

25. The compound according to claim 23 wherein $R^2$ is cyclothioalkyl substituted on a position of $R^2$ that is attached to $Z^1$ or on a position adjacent to the thio moiety of the cyclothioalkyl.

26. The compound according to claim 1 wherein $R^2$ is isopropyl, cyclopropylmethyl, cyclopentyl, trinorbornyl, trinorbornenyl, tricyclo[2.2.1.0$^{2.6}$]heptanyl and tetrahydrothiophenyl.

27. The compound according to claim 1 wherein $R^2$ is cyclothioalkyl oxidized to the corresponding S-oxide or S,S-dioxide.

28. The compound according to claim 1 wherein $R^1$ is lower alkyl optionally substituted by halo; and $R^2$ is isopropyl, cyclopropylmethyl, cyclopentyl, trinorbornyl, trinorbornenyl, tricyclo[2.2.1.0$^{2.6}$]heptanyl and tetrahydrothiophenyl.

29. A pharmaceutical composition comprising a pharmaceutically acceptable amount of the compound of claim 1 and a pharmaceutically acceptable carrier.

30. A method for treating asthma comprising administering to a patient suffering from said disease state an effective amount of the compound of claim 1.

* * * * *

UNITED STATES PATENT AND TRADEMARK OFFICE
CERTIFICATE OF CORRECTION

PATENT NO. : 8,129,537 B2  
APPLICATION NO. : 12/693791  
DATED : March 6, 2012  
INVENTOR(S) : Garry Fenton, Tahir Nadeem Majid and Malcolm Norman Palfreyman Page 1 of 1

It is certified that error appears in the above-identified patent and that said Letters Patent is hereby corrected as shown below:

Title page, Item (73) Assignee should read:

--AVENTIS PHARMA LIMITED--

Signed and Sealed this
Tenth Day of July, 2012

David J. Kappos
*Director of the United States Patent and Trademark Office*